(12) United States Patent
Knudsen

(10) Patent No.: US 10,900,089 B2
(45) Date of Patent: Jan. 26, 2021

(54) METHODS FOR PREDICTING DRUG RESPONSIVENESS IN CANCER PATIENTS

(71) Applicant: Oncology Venture ApS, Hørsholm (DK)

(72) Inventor: Steen Knudsen, Scottsdale, AZ (US)

(73) Assignee: Oncology Venture ApS, Hørsholm (DK)

( * ) Notice: Subject to any disclaimer, the term of this patent is extended or adjusted under 35 U.S.C. 154(b) by 74 days.

(21) Appl. No.: 15/978,655

(22) Filed: May 14, 2018

(65) Prior Publication Data

US 2018/0334724 A1   Nov. 22, 2018

Related U.S. Application Data

(60) Provisional application No. 62/507,106, filed on May 16, 2017.

(51) Int. Cl.
| | | |
|---|---|---|
| *C12Q 1/6886* | (2018.01) | |
| *A61P 35/02* | (2006.01) | |
| *A61K 31/351* | (2006.01) | |
| *A61K 45/06* | (2006.01) | |
| *G16H 50/30* | (2018.01) | |
| *G16H 50/20* | (2018.01) | |
| *G16H 20/10* | (2018.01) | |

(52) U.S. Cl.
CPC .......... *C12Q 1/6886* (2013.01); *G16H 20/10* (2018.01); *G16H 50/20* (2018.01); *G16H 50/30* (2018.01); *A61K 31/351* (2013.01); *A61K 45/06* (2013.01); *A61P 35/02* (2018.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 8,445,198 B2 | 5/2013 | Knudsen |
| 9,598,734 B2 | 3/2017 | Knudsen |
| 9,725,769 B1 | 8/2017 | Knudsen |
| 10,392,667 B2 | 8/2019 | Knudsen |
| 2009/0023149 A1* | 1/2009 | Knudsen .............. C12Q 1/6886 435/6.14 |
| 2014/0106986 A1 | 4/2014 | Knudsen et al. |
| 2016/0199399 A1 | 7/2016 | Knudsen |
| 2017/0283884 A1 | 10/2017 | Knudsen |
| 2018/0087113 A1 | 3/2018 | Knudsen |
| 2018/0100197 A1 | 4/2018 | Knudsen |
| 2018/0202004 A1 | 7/2018 | Knudsen |

FOREIGN PATENT DOCUMENTS

| | | |
|---|---|---|
| RU | 2528247 C2 | 9/2014 |
| WO | WO-2007/072225 A2 | 6/2007 |
| WO | WO-2011/135459 A2 | 11/2011 |
| WO | WO-2012/024543 A1 | 2/2012 |
| WO | WO-2014/195032 A1 | 12/2014 |

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Extended European Search Report for European Application No. 18172585.4, dated Oct. 9, 2018 (7 pages).

* cited by examiner

*Primary Examiner* — Katherine D Salmon
(74) *Attorney, Agent, or Firm* — Clark & Elbing LLP

(57) ABSTRACT

The present invention features methods, devices, and kits for detecting a level of one or more biomarkers in a patient with cancer or determining the responsiveness of a patient with cancer to a treatment, such as treatment with an anthracycline. The invention further includes methods of treating a patient with cancer by administering, e.g., the anthracycline.

30 Claims, 2 Drawing Sheets

Specification includes a Sequence Listing.

METHODS FOR PREDICTING DRUG RESPONSIVENESS IN CANCER PATIENTS

BACKGROUND

DNA microarrays can be used to measure gene expression in tumor samples from patients and to facilitate diagnosis. Gene expression can reveal the presence of cancer in a patient in addition to the type, stage, and origin. Gene expression may even have a role in predicting the efficacy of cancer therapies. In recent decades, the National Cancer Institute (NCI) has tested cancer therapeutics for their effect in limiting the growth of 60 human cancer cell lines. The NCI has also measured gene expression in those 60 cancer cell lines using DNA microarrays. Various studies have explored the relationship between gene expression and therapeutic effect using the NCI datasets.

During cancer treatment, critical time is often lost due to a trial and error approach to finding an effective therapy. In addition, cancer cells often develop resistance to a previously effective therapy. In such situations, patient outcome would be greatly improved by early detection of such resistance to therapy.

Thus, there exists a need in the art for methods, devices, and kits that can predict the responsiveness of cancer patients to a medical treatment for cancer.

SUMMARY OF THE INVENTION

The invention features methods for testing a tumor sample of a patient (e.g., a human) with cancer (e.g., a patient having a known cancer type, such as a solid tumor or hematological cancer) by detecting a level of one or more biomarkers (e.g., one, two, three, four, five, ten, twenty, or all of the biomarkers shown in Tables 1-4, such as HSLS1 (SEQ ID NO: 1)). In particular, the patient is resistant to one or more cancer therapies and/or has an unknown responsiveness to an anthracycline (e.g., doxorubicin, epirubicin, daunorubicin, or idarubicin, or an anthracycline-containing liposome, such as a doxorubicin-containing liposome (e.g., 2B3-101)). The methods can be used to determine responsiveness of a cancer patient to treatment with an anthracycline, such as doxorubicin (e.g., a doxorubicin-containing liposome), epirubicin (e.g., an epirubicin-containing liposome), daunorubicin (e.g., a daunorubicin-containing liposome), or idarubicin (e.g., an idarubicin-containing liposome). The invention also features methods of treating cancer in a patient that include administering an anthracycline to the patient, in which the patient is or has been determined to be responsive to an anthracycline according to the diagnostic methods described herein.

A first aspect of the invention features a method for testing a tumor sample of a patient with cancer (e.g., a patient having a known cancer type), such as a patient that is resistant to one or more cancer therapies and has an unknown responsiveness to an anthracycline (e.g., a patient with a solid tumor or hematological cancer that is resistant to one or more cancer therapies other than the anthracycline). The method includes: (a) contacting the sample from the patient including one or more nucleic acid molecules with a device including: i) one or more single-stranded nucleic acid molecules capable of specifically hybridizing with nucleotides of one or more biomarkers of sensitivity selected from those listed in Tables 1 and/or 3 or a complement thereof (e.g., one, two, three, four, five, ten, twenty, or all of the biomarkers shown in Tables 1 and/or 3, such as HSLS1 (SEQ ID NO: 1)); and/or ii) one or more single-stranded nucleic acid molecules capable of specifically hybridizing with nucleotides of one or more biomarkers of resistance selected from those listed in Tables 2 and/or 4 or a complement thereof (e.g., one, two, three, four, five, ten, twenty, or all of the biomarkers shown in Tables 2 and/or 4, such as SFN (SEQ ID NO: 105, 106, 108, 475, 480, or 491)); and (b) detecting a level of the one or more biomarkers of sensitivity or the complement thereof and/or the one or more biomarkers of resistance or the complement thereof in the sample by detecting hybridization between the one or more single-stranded nucleic acid molecules of the device and the one or more nucleic acid molecules of the sample (e.g., by performing microarray analysis or quantitative reverse transcriptase polymerase chain reaction (qRT-PCR)). The level of the biomarker(s) may be detected by determining the level of a messenger RNA (mRNA) corresponding to the biomarker(s) (e.g., an mRNA expressed from HSLS1 (SEQ ID NO: 1)) or a complementary DNA (cDNA) thereof.

In particular, the one or more of the cancer therapies to which the patient is resistant include surgery, radiation, or a therapeutic agent, such as irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

A second aspect of the invention features a method of determining responsiveness of a patient with cancer (e.g., one of the cancers described herein, such as breast cancer) to the anthracycline. In particular, the patient may have a cancer (e.g., breast cancer) that is resistant to one or more cancer therapies other than the anthracycline, such as irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab. The method includes a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with nucleotides of one or more biomarkers of sensitivity selected from those listed in Tables 1 and/or 3 or a complement thereof (e.g., one, two, three, four, five, ten, twenty, or all of the biomarkers shown in Tables 1 and/or 3, such as HSLS1 (SEQ ID NO: 1)); and/or ii) one or more single-stranded nucleic acid molecules capable of specifically hybridizing with nucleotides of one or more biomarkers of resistance selected from those listed in Tables 2 and/or 4 or a complement thereof (e.g., one, two, three, four, five, ten, twenty, or all of the biomarkers shown in Tables 2 and/or 4, such as SFN (SEQ ID NO: 105, 106, 108, 475, 480, or 491)); and (b) detecting a level of the one or more biomarkers of sensitivity or the complement thereof and/or the one or more biomarkers of resistance or the complement thereof by detecting hybridization between the single-stranded nucleic acid molecules of the device and the one or more nucleic acid molecules of the sample. The level of the biomarker(s) may be detected by determining the level of a messenger RNA (mRNA) corresponding to the biomarker(s) (e.g., an mRNA expressed from HSLS1 (SEQ ID NO: 1)) or a complementary DNA (cDNA) thereof.

The patient is determined to be responsive to the anthracycline if or when i) the level of the biomarker(s) of sensitivity (e.g., HSLS1 (SEQ ID NO: 1)) or the complement thereof is substantially similar to the level of the biomarker(s) of sensitivity or the complement thereof in a cell or tissue known to be sensitive to the anthracycline; and/or ii) the level of the biomarker(s) of resistance or the complement thereof (e.g., SFN (SEQ ID NO: 105, 106, 108, 475, 480, or 491)) is substantially dissimilar to the level of the biomarker(s) of resistance or the complement thereof in a cell (e.g., a cancer cell) or tissue (e.g., a tumor tissue) known to be resistant to the anthracycline. In particular, the cell or tissue known to be sensitive to the anthracycline and/or the cell or tissue known to be resistant to the anthracycline is of the same type or is of the same type of cancer as a cell or tissue in the sample from the patient or from which the one or more nucleic acid molecules of the sample are derived.

The method of the first or second aspect can further include calculating a difference score for the patient by subtracting the mean expression levels of a plurality of the biomarkers of resistance (e.g., one, two, three, four, five, ten, twenty, or all of the biomarkers shown in Tables 2 and/or 4, such as SFN (SEQ ID NO: 105, 106, 108, 475, 480, or 491)) from the mean expression levels of a plurality of the biomarkers of sensitivity (e.g., one, two, three, four, five, ten, twenty, or all of the biomarkers shown in Tables 1 and/or 3, such as HSLS1 (SEQ ID NO: 1)). The method may further include administering the anthracycline (e.g., doxorubicin, epirubicin, daunorubicin, or idarubicin, or an anthracycline-containing liposome, such as a doxorubicin-containing liposome (e.g., 2B3-101)) to the patient if the difference score indicates that the patient is responsive to the anthracycline. Alternatively, the method further includes administering the anthracycline to the patient when the difference score indicates that the patient is responsive to the anthracycline, such as doxorubicin (e.g., a doxorubicin-containing liposome).

Moreover, the method of the first or second aspect can further include administering the anthracycline to the patient if or when: i) the level of the biomarker(s) of sensitivity or the complement thereof (e.g., HSLS1 (SEQ ID NO: 1)) is substantially similar to the level of the biomarker(s) of sensitivity or the complement thereof in a cell (e.g., a cancer cell) or tissue (e.g., a tumor tissue) known to be sensitive to the anthracycline; and/or ii) the level of the biomarker(s) of resistance or the complement thereof (e.g., SFN (SEQ ID NO: 105, 106, 108, 475, 480, or 491)) is substantially dissimilar to the level of the biomarker(s) of resistance or the complement thereof in a cell (e.g., a cancer cell) or tissue (e.g., a tumor tissue) known to be resistant to the anthracycline.

The method can include administering one or more cancer therapies other than the anthracycline to the patient if or when: i) the level of the biomarker(s) of sensitivity or the complement thereof (e.g., HSLS1 (SEQ ID NO: 1)) is substantially dissimilar to the level of the biomarker(s) of sensitivity or the complement thereof in a cell (e.g., a cancer cell) or tissue (e.g., a tumor tissue) known to be sensitive to the anthracycline; and/or ii) the level of the biomarker(s) of resistance or the complement thereof (e.g., SFN (SEQ ID NO: 105, 106, 108, 475, 480, or 491)) is substantially similar to the level of the biomarker(s) of resistance or the complement thereof in a cell (e.g., a cancer cell) or tissue (e.g., a tumor tissue) known to be resistant to the anthracycline. The method can further include administering one or more cancer therapies other than the anthracycline to the patient if or when: i) the level of the biomarker(s) of sensitivity or the complement thereof (e.g., HSLS1 (SEQ ID NO: 1)) is substantially dissimilar to the level of the biomarker(s) of sensitivity or the complement thereof in a cell (e.g., a cancer cell) or tissue (e.g., a tumor tissue) known to be sensitive to the anthracycline; and/or ii) the level of the biomarker(s) of resistance or the complement thereof (e.g., SFN (SEQ ID NO: 105, 106, 108, 475, 480, or 491)) is substantially similar to the level of the biomarker(s) of resistance or the complement thereof in a cell (e.g., a cancer cell) or tissue (e.g., a tumor tissue) known to be resistant to the anthracycline.

In particular, the one or more of the cancer therapies that can be administered to a patient determined not be sensitive to an anthracycline include surgery, radiation, or a therapeutic agent, such as irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, ZD1839, anastrozole, and rituximab.

The invention also features a method of treating cancer in a patient in need thereof (e.g., one of the cancers described herein, such as breast cancer) that includes administering an anthracycline to the patient, in which the patient has been determined to be responsive to the anthracycline according to the method of the first or second aspect of the invention. In particular, the patient may have a cancer that is resistant to one or more cancer therapies other than the anthracycline (e.g., a patient having a known cancer type, such as a solid tumor or hematological cancer).

A third aspect of the invention features a method of treating a patient with cancer (e.g., a cancer described herein, such as a solid tumor or hematological cancer). In particular, the cancer may be resistant to one or more cancer therapies other than the anthracycline. The patient may have brain cancer, a brain metastasis, or breast cancer that is resistant to one or more cancer therapies other than the anthracycline. The method includes (a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with nucleotides of one or more biomarkers of sensitivity selected from those listed in Tables 1 and/or 3 or a complement thereof (e.g., HSLS1 (SEQ ID NO: 1)); and/or ii) one or more single-stranded nucleic acid molecules capable of specifically hybridizing with nucleotides of one or more biomarkers of resistance selected from those listed in Tables 2 and/or 4 or a complement thereof (e.g., SFN (SEQ ID NO: 105, 106, 108, 475, 480, or 491)); (b) detecting a level of the one or more biomarkers of sensitivity or the complement thereof and/or the one or more biomarkers of resistance or the complement thereof by detecting hybridization between the one or more single-stranded nucleic acid molecules of the device and the one or more nucleic acid molecules of the sample; and (c) administering the anthracycline to the patient if or when: i) the level of the biomarker(s) of sensitivity or the complement thereof is substantially similar to the level of the biomarker(s) of sensitivity or the complement thereof in a cell (e.g., a cancer cell) or tissue (e.g., a tumor tissue) known to be sensitive to the anthracycline; and/or ii) the level of the biomarker(s) of resistance or the complement thereof is substantially dissimilar to the level of the biomarker(s) of resistance or the complement thereof in a cell (e.g., a cancer cell) or tissue (e.g., a tumor tissue) known to be resistant to the anthracycline. In particular, the cell or tissue known to be sensitive to the anthracycline and/or the cell or tissue known to be resistant to the anthracycline is of the same type or is of the same type of cancer as a cell or tissue in the sample from the patient or from which the one or more nucleic acid molecules of the sample are derived.

The method of the third aspect of the invention may further include administering one or more additional therapies (e.g., surgery, radiation, or a therapeutic agent) to the patient prior to, concurrently with, or after administration of the anthracycline. In particular, the therapeutic agent may be selected from the group consisting of irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methylgag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab. The therapeutic agent and/or the anthracycline can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically. Preferably, the anthracycline is administered by intravenous injection. The anthracycline may be administered to the patient at a dose of about 1 mg/kg to about 100 mg/kg of anthracycline. In particular, the anthracycline is administered to the patient at a dose of about 5 mg/kg, about 6 mg/kg, about 7 mg/kg, about 8 mg/kg, about 9 mg/kg, or about 10 mg/kg. The method may include administering the anthracycline to the patient in a treatment regimen daily, weekly, or monthly. The method may include administering the anthracycline to the patient in a treatment regimen at least once, twice, three, four, five, or six times weekly, in which the treatment regimen may optionally be repeated two to twenty times.

In the third aspect of the invention, the contacting step (a) and the detecting step (b) may occur prior to, concurrent, or after administration of the anthracycline to the patient. Additionally, the contacting step (a) and the detecting step (b) may occur two or more times, e.g., during treatment with the anthracycline. For example, the contacting step (a) and the measuring step (b) may occur two or more times to assess the continued sensitivity of the patient to the anthracycline.

In any of the above aspects of the invention, the anthracycline is selected from the group consisting of doxorubicin, epirubicin, daunorubicin, idarubicin, aclarubicin, nemorubicin, pixantrone, and valrubicin or a derivative thereof. The anthracycline or derivative thereof may be incorporated into a liposomal formulation. In particular, the liposomal formulation may contain doxorubicin or a derivative thereof, epirubicin or a derivative thereof, daunorubicin or a derivative thereof, idarubicin or a derivative thereof, aclarubicin or a derivative thereof, nemorubicin or a derivative thereof, pixantrone or a derivative thereof, or valrubicin or a derivative thereof.

In the second or third aspects of the invention, the patient may be resistant to one or more cancer therapies other than an anthracycline, such as surgery, radiation, or a therapeutic agent. In particular, the therapeutic agent may be irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methylgag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

In any of the above aspects of the invention, the cancer is selected from a solid tumor cancer and a hematological cancer. For example, the cancer is brain cancer, breast cancer, acute myelogenous leukemia (AML), acute lymphoblastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN). In particular, the cancer is breast cancer, such as an estrogen receptor-positive (ERpos) breast cancer and/or a metastatic form of breast cancer. Additionally, the cancer may be a brain metastasis (e.g., breast cancer that has metastasized to the brain).

In any of the above aspects of the invention, the patient may exhibit cancer relapse (e.g., relapse of breast cancer), such as relapse after a first cancer treatment and prior to treatment with a therapeutic agent other than the anthracycline. Alternatively, the patient may have not been administered a treatment for cancer. Additionally, the patient may not have been determined to be resistant to the anthracycline.

In any of the above aspects of the invention, the device can include at least two, at least three, at least four, at least five, at least six, at least seven, at least eight, at least nine, at least ten, or more single-stranded nucleic acid molecules capable of specifically hybridizing with the nucleotides of one or more biomarkers of sensitivity selected from the biomarkers of Tables 1 and 3 or a complement thereof (e.g., HSLS1 (SEQ ID NO: 1); and/or at least two, at least three, at least four, at least five, at least six, at least seven, at least eight, at least nine, at least ten, or more single-stranded nucleic acid molecules capable of specifically hybridizing with the nucleotides of one or more biomarkers of resistance selected from the biomarkers of Tables 2 and 4 or a complement thereof (e.g., SFN (SEQ ID NO: 105, 106, 108, 475, 480, or 491)). In particular, one or more of the single-stranded nucleic acid molecules of the device have a length in the range of 10 to 100 nucleotides in length (e.g., a length in the range of 20 to 60 nucleotides). For example, the one or more single-stranded nucleic acid molecules are labeled or immobilized on a solid substrate.

In any of the above aspects of the invention, the device can be a microarray, such as a deoxyribonucleic acid (DNA)-based platform. Alternatively, the device can be used to perform a qRT-PCR reaction (e.g., the device is used with a system for detecting the amplification product, for example, by fluorescence or by another method). The methods may also utilize both a microarray and a qRT-PCR. Thus, the level of the biomarker(s) of sensitivity (e.g., one, two, three, four, five, ten, twenty, or all of the biomarkers shown in Tables 1 and 3, such as HSLS1 (SEQ ID NO: 1)) and/or the biomarker(s) of resistance (e.g., one, two, three, four, five, ten, twenty, or all of the biomarkers shown in Tables 2 and 4, such as SFN (SEQ ID NO: 105, 106, 108, 475, 480, or 491)) can be measured using qRT-PCR. In particular, the level of the one or more biomarkers of sensitivity or the complement thereof (e.g., one, two, three, four, five, ten, twenty, or all of the biomarkers shown in Tables 1 and 3, such as HSLS1 (SEQ ID NO: 1)) and/or the one or more biomarkers of resistance or the complement thereof (e.g., one, two, three, four, five, ten, twenty, or all of the biomarkers shown in Tables 2 and 4, such as SFN (SEQ ID NO: 105, 106, 108, 475, 480, or 491)) are detected by performing microarray analysis or qRT-PCR. Additionally, the nucleic acid molecules of the sample may include mRNA or a cDNA thereof.

In any of the above aspects of the invention, the biomarker of sensitivity may be selected from one or more of HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ARHGAP15 (SEQ ID NO: 10), CD99 (SEQ ID NO: 12 or 31), SRSF7 (SEQ ID NO: 13), SELPLG (SEQ ID NO: 15), SFRS7 (SEQ ID NO: 19 or 54), and CAP350 (SEQ ID NO: 20 or 61). The biomarker of resistance may be selected from one or more of SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124).

For example, the biomarkers of sensitivity may include HSLS1 (SEQ ID NO: 1) and PTPRCAP (SEQ ID NO: 2). The biomarkers of sensitivity may include HSLS1 (SEQ ID NO: 1), PTPRCAP (SEQ ID NO: 2), and NEIL3 (SEQ ID NO: 3). The biomarkers of sensitivity may include HSLS1 (SEQ ID NO: 1), PTPRCAP (SEQ ID NO: 2), NEIL3 (SEQ ID NO: 3), and PTPRC (SEQ ID NO: 4, 20, or 27). The biomarkers of sensitivity may include HSLS1 (SEQ ID NO: 1), PTPRCAP (SEQ ID NO: 2), NEIL3 (SEQ ID NO: 3), PTPRC (SEQ ID NO: 4, 20, or 27), and IFI16 (SEQ ID NO: 5). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), and RHOH (SEQ ID NO: 6). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), and SSBP2 (SEQ ID NO: 7). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), and CD2 (SEQ ID NO 8). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), and ITGA4 (SEQ ID NO: 9). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), and ARHGAP15 (SEQ ID NO: 10). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), and SRPK2 (SEQ ID NO: 11). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2

(SEQ ID NO 8), ITGA4 (SEQ ID NO: 9), ARHGAP15 (SEQ ID NO: 10), SRPK2 (SEQ ID NO: 11), and CD99 (SEQ ID NO: 12 or 31). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), and SRSF7 (SEQ ID NO: 13). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), and CTCF (SEQ ID NO: 14). The biomarkers of sensitivity may include HSLS1 (SEQ ID NO: 1), TPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), and SELPLG (SEQ ID NO: 15).

For example, the biomarkers of resistance may include SFN (SEQ ID NO: 105, 106, 108, 475, 480, or 491) and ACTN1 (SEQ ID NO: 104 or 110). The biomarkers of resistance may include SFN (SEQ ID NO: 105, 106, 108, 475, 480, or 491), ACTN1 (SEQ ID NO: 104 or 110), and CTBP2 (SEQ ID NO: 107 or 119). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), and FHL2 (SEQ ID NO: 109). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), and CST6 (SEQ ID NO: 111). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), and NR2F2 (SEQ ID NO: 112 or 116). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), and REXO2 (SEQ ID NO: 113). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), and ANXA2 (SEQ ID NO: 114, 117, or 126). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), and TJP1 (SEQ ID NO: 115). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), and IGF2BP2 (SEQ ID NO: 118). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), and CCND1 (SEQ ID NO: 120). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), and COTL1 (SEQ ID NO: 121). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), and AMOTL2 (SEQ ID NO: 122). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), and SDC4 (SEQ ID NO: 123). The biomarkers of resistance may include SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124).

Definitions

As used herein, "a" and "an" means "at least one" and "one or more" unless otherwise indicated. In addition, the singular forms "a", "an", and "the" include plural referents unless the context clearly dictates otherwise.

As used herein, "about" refers to an amount±10% of the recited value.

The term "anthracycline" as used herein refers to a class of antitumor agents that are derived from *Streptomyces* sp. Anthracyclines have a tetracyclic quinoid structure, such has a tetracyclic quinoid structure in which the ring structure is coupled via a glycosidic linkage to a sugar. Exemplary anthracyclines include, but are not limited to, doxorubicin, epirubicin, daunorubicin, idarubicin, aclarubicin, nemorubicin, pixantrone, valrubicin, esorubicin, idarubicin, carminomycin, 4-demethoxy-4'-O-methyl doxorubicin, 4'-O-tetrahydropyranyl-doxorubicin, 3'-deamino-3'-(3"-cyano-4"-morpholinyl) doxorubicin, aclacinomycin, and derivatives thereof. Anthracyclines may be formulated in a liposome, such as a doxorubicin-containing liposome, epirubicin-containing liposome, daunorubicin-containing liposome, or idarubicin-containing liposome. For example, an anthracycline-containing liposome (e.g., a doxorubicin-containing liposome) may include about 40% to about 75% (mol/mol) of a neutral phospholipid, about 20% to about 45% (mol/mol) of cholesterol (Chol), and about 3% to about 6%

(mol/mol) of a polymer-conjugated lipid. In particular, a doxorubicin-containing liposome may be 2B3-101 (DOXIL®/CAELYX®), which includes hydrogenated soy phosphatidylcholine (HSPC) in an amount of about 55% (mol/mol), Chol in an amount of about 40% (mol/mol), and [poly(ethylene glycol)]-distearoyl phosphatidyl ethanolamine (DSPE-PEG) conjugated to glutiothionate (DSPE-PEG-GSH) in an amount of about 5% (mol/mol). For example, the composition of the 2B3-101 liposome in milligrams (mg) can be as follows: about 2 mg/mL doxorubicin, about 10 mg/mL HSPC, about 3 mg/mL of DSPE-PEG2000-mal-GSH, and about 3 mg/mL of cholesterol.

The anthracycline-containing liposome (e.g., 2B3-101 (DOXIL®/CAELYX®)) is formulated to release an encapsulated drug (e.g., an anthracycline, such as doxorubicin or epirubicin) from the core of a hydrophobic layer into tumor tissue. For example, a gluthathione-conjugated PEGylated liposomal formulation may facility the uptake of an anthracyclines (e.g., doxorubicin) into brain tissue, thereby treating brain tumors or brain metastasis, e.g., breast cancer that has metastasized to the brain. A doxorubicin-containing lipsome (e.g., 2B3-101 (DOXIL®/CAELYX®)) is described in, e.g., U.S. Patent Application Publication No. 2014/227185 and Birngruber et al. (J. Pharm. Sci. 103:1945-1948, 2014), each of which is hereby incorporated by reference.

By "biomarker" is meant a nucleic acid molecule (e.g., a mRNA or its complement, for example, a cDNA, or the nucleic acid sequence of all or a fragment of a gene) or a protein encoded by the nucleic acid molecule present in, or from, a cell or tissue. The level of the biomarker correlates to the responsiveness (e.g., sensitivity or resistance) of the cell or tissue (and thus, the patient in which the cell or tissue resides or the patient from which the cell or tissue was obtained) to a cancer treatment (e.g., anthracycline). In particular, biomarkers of sensitivity correspond to the nucleic acid molecules or the complements thereof (e.g., a mRNA or its complement or a cDNA thereof) shown in Tables 1 and 3, or the proteins encoded by the nucleic acid molecules, and biomarkers of resistance correspond to the nucleic acid molecules or the complements thereof (e.g., a mRNA or its complement or a cDNA thereof) shown in Tables 2 and 4, or the proteins encoded by the nucleic acid molecules.

The terms "cancer" and "cancerous" refer to or describe the physiological condition in mammals (e.g., humans) that is typically characterized by unregulated cell proliferation. Examples of cancer include, but are not limited to, brain cancer (e.g., astrocytoma, glioblastoma multiforme, and craniopharyngioma), metastatic cancer (e.g., breast cancer that has metastasized to the brain), breast cancer (e.g., an estrogen receptor-positive (ERpos) breast cancer or a metastatic form of breast cancer), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), stomach cancer, intra-epithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. The term cancer includes solid tumors (e.g., breast cancer or brain cancer) and hematological cancers (e.g., cancer of the blood, such as lymphoma (e.g., diffuse large B-cell lymphoma (DLBCL), cutaneous T-cell lymphoma (CTCL), peripheral T-cell lymphoma (PTCL), and Hodgkin's lymphoma)).

"Gene" as used herein indicates a coding or noncoding gene whose activity can be determined by measuring RNA (e.g., mRNA) transcribed from the gene, or its complement. Examples include protein coding genes, microRNAs, small nuclear RNAs and other RNAs with catalytic, regulatory or coding properties.

To "inhibit growth" as used herein means causing a reduction in cell growth (e.g., cancer cell growth, such as the NCI60 cancer cell lines) in vivo or in vitro by, e.g., 10%, 20%, 30%, 40%, 50%, 60%, 70%, 80%, 90%, 95%, or 99% or more, as evident by a reduction in the proliferation of cells exposed to an anthracycline (e.g., doxorubicin, epirubicin, daunorubicin, or idarubicin, or an anthracycline-containing liposome, such as a doxorubicin-containing liposome (e.g., 2B3-101 (DOXIL®/CAELYX®)) relative to the proliferation of cells in the absence of the anthracycline. Growth inhibition may be the result of treatment with an anthracycline that induces apoptosis in a cell, induces necrosis in a cell, slows cell cycle progression, disrupts cellular metabolism, induces cell lysis, or induces some other mechanism that reduces the proliferation of cells.

"Microarray" as used herein means a device employed by any method that quantifies one or more subject oligonucleotides, e.g., RNA, DNA, cDNA, or analogues thereof, at a time. For example, many DNA microarrays, including those made by Affymetrix (e.g., an Affymetrix HG-U133A or HG-U133_Plus_2 array), use several probes for determining the level of a single biomarker. The DNA microarray may contain oligonucleotide probes that may be, e.g., full-length cDNAs complementary to an RNA or cDNA fragments that hybridize to part of an RNA. The DNA microarray may also contain modified versions of DNA or RNA, such as locked nucleic acids or LNA. Exemplary RNAs include mRNA, miRNA, and miRNA precursors.

"NCI60" as used herein means a panel of 60 cancer cell lines from lung, colon, breast, ovarian, leukemia, renal, melanoma, prostate, and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COL0205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

The terms "patient" and "subject," as used interchangeably herein, refer to any animal (e.g., a mammal, such as a human). A patient to be treated or tested for responsiveness to a treatment (e.g., treatment with an anthracycline, such as 2B3-101) according to the methods described herein may be one who has been diagnosed with a cancer, such as those described herein, e.g., brain cancer, breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN). Diagnosis may be performed by any method or technique known in the art, such as x-ray, MRI, or biopsy, and may also be confirmed by a physician. To minimize exposure of a patient to drug treatments that may not be therapeutic, the patient may be determined to be either responsive or non-responsive to a cancer treatment, such as an anthracycline (e.g., 2B3-101), according to the methods described herein prior to treatment.

As used herein, the term "percent (%) sequence identity" refers to the percentage of nucleic acid residues of a candidate sequence, e.g., a probe or primer of the invention, that are identical to the nucleic acid residues of a reference sequence, e.g., a biomarker sequence of the invention, after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using computer software, such as BLAST, BLAST-2, BLAST-P, BLAST-N, BLAST-X, WU-BLAST-2, ALIGN, ALIGN-2, CLUSTAL, Megalign (DNASTAR). In addition, those skilled in the art can determine appropriate parameters for measuring alignment, including any algorithms needed to achieve optimal alignment over the length of the sequences being compared.

"Resistant" and "resistance" as used herein means that a cell (e.g., a cancer cell), a tissue containing the cell (e.g., a tumor), or a patient containing the cell or tissue having cancer (e.g., a human having cancer) is non-responsive to treatment with an anti-cancer agent (e.g., an anthracycline, such as doxorubicin, epirubicin, daunorubicin, or idarubicin). In particular, the treatment reduces the growth of a resistant cell (e.g., the cancer cell) in vitro by less than about 40%, 30%, 20%, 10%, 5%, 1%, or less, relative to the growth of a less resistant cell not exposed to the treatment. Resistance to treatment may be determined by a cell proliferation assay, e.g., a cell-based assay, which measures the growth of treated cells as a function of the absorbance of the cells of an incident light beam, such as the NCI60 assays described herein. In this assay, greater absorbance indicates greater cell growth, and thus, resistance to the treatment.

The terms "responsive" and "responsiveness," as used herein, refer to the likelihood that an anthracycline (e.g., doxorubicin, epirubicin, daunorubicin, or idarubicin, or an anthracycline-containing liposome, such as a doxorubicin-containing liposome (e.g., 2B3-101)), a tissue (e.g., a tumor), or a patient with cancer (e.g., a human having cancer). For example, the desired effect can include inhibition of the growth of a cancer cell in vitro by more than 10%, 20%, 30%, 40%, 50%, 60%, 70%, 80%, 90%, or 100% relative to the growth of a cancer cell not exposed to anthracycline. The desired effect can also include reduction in tumor mass by, e.g., about 10%, 20%, 30%, 40%, 50%, 60%, 70%, 80%, 90%, or 100%. Responsiveness to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity to the treatment. A greater reduction in growth indicates more sensitivity to the treatment. In particular, "responsiveness" is a measure of the sensitivity or resistance of a patient to a treatment for cancer (e.g., an anthracycline).

The term "sample," as used herein, refers to any specimen (such as cells, tissue (e.g., a tissue sample obtained by biopsy), blood, serum, plasma, urine, cerebrospinal fluid, or pancreatic fluid) taken from a subject. Preferably, the sample is taken from a portion of the body affected by a cancer (e.g., a biopsy of the cancer tissue, such as breast cancer tissue). Biopsy may involve fine needle aspiration biopsy, core needle biopsy (e.g., stereotactic core needle biopsy, vacuum-assisted core biopsy, or magnetic resonance imaging (MRI) guided biopsy), or surgical biopsy (e.g., incisional biopsy or excisional biopsy). The sample may undergo additional purification and processing, for example, to remove cell debris and other unwanted molecules. Additional processing may further involve producing cDNA molecules corresponding to nucleic acid molecules (e.g., mRNA) in the sample and/or amplification of the nucleic acid molecules, e.g., using PCR, such as RT-PCR. The standard methods of sample purification, such as removal of unwanted molecules, are known in the art.

"Sensitive" and "sensitivity" as used herein refer to a cell (e.g., a cancer cell), a tissue containing the cell (e.g., a tumor), or a patient containing the cell or tissue having cancer (e.g., a human having cancer) that is responsive to treatment with an anti-cancer agent (e.g., an anthracycline, such as doxorubicin, epirubicin, daunorubicin, or idarubicin). In particular, the treatment inhibits the growth of the cell (e.g., the cancer cell) in vitro by about 50%, 60%, 70%, 80%, 90%, 95%, 99% or 100% relative to the growth of a cell not exposed to the treatment. Sensitivity to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity to the treatment.

The term "specific hybridization" as used herein refers to when complementary nucleic acid sequences form a stable duplex under high stringency conditions, such as high hybridization temperature and low salt in hybridization buffers, which permit only hybridization between nucleic acid sequences that are highly similar. Nucleic acids are referred to as "complementary" that contain nucleotides or nucleotide homologues that can form hydrogen bonds according to Watson-Crick base-pairing rules (e.g., G with C, A with T or A with U) or other hydrogen bonding motifs such as for example diaminopurine with T, 5-methyl C with G, 2-thiothymidine with A, inosine with C, pseudoisocytosine with G, etc. Anti-sense RNA may be complementary to other oligonucleotides, e.g., mRNA.

"Treatment," "medical treatment," to "treat," and "therapy," as used interchangeably herein, refer to administering or exposing a patient with cancer (e.g., a human) to a therapeutic agent, such as anthracycline (e.g., doxorubicin, epirubicin, daunorubicin, or idarubicin, or an anthracycline-containing liposome, such as a doxorubicin-containing liposome (e.g., 2B3-101)), or to some other form of medical intervention used to treat or prevent a disease, disorder, or condition (e.g., surgery, cryotherapy, radiation therapy, or combinations thereof). In particular, a medical treatment can be or can include administration of an anthracycline. For example, the treatment may be of a solid tumor or a hematological cancer. Radiation therapy includes the administration of a radioactive agent to a patient or exposure of a patient to radiation. The radiation may be generated from sources, such as particle accelerators and related medical devices or agents that emit, e.g., X-radiation, gamma radiation, or electron (Beta radiation) beams. A treatment may be or further include surgery, e.g., to remove a tumor from a subject or living organism.

Other features and advantages of the invention will be apparent from the following Detailed Description, the drawings, and the claims.

DETAILED DESCRIPTION OF THE INVENTION

Figure 1:
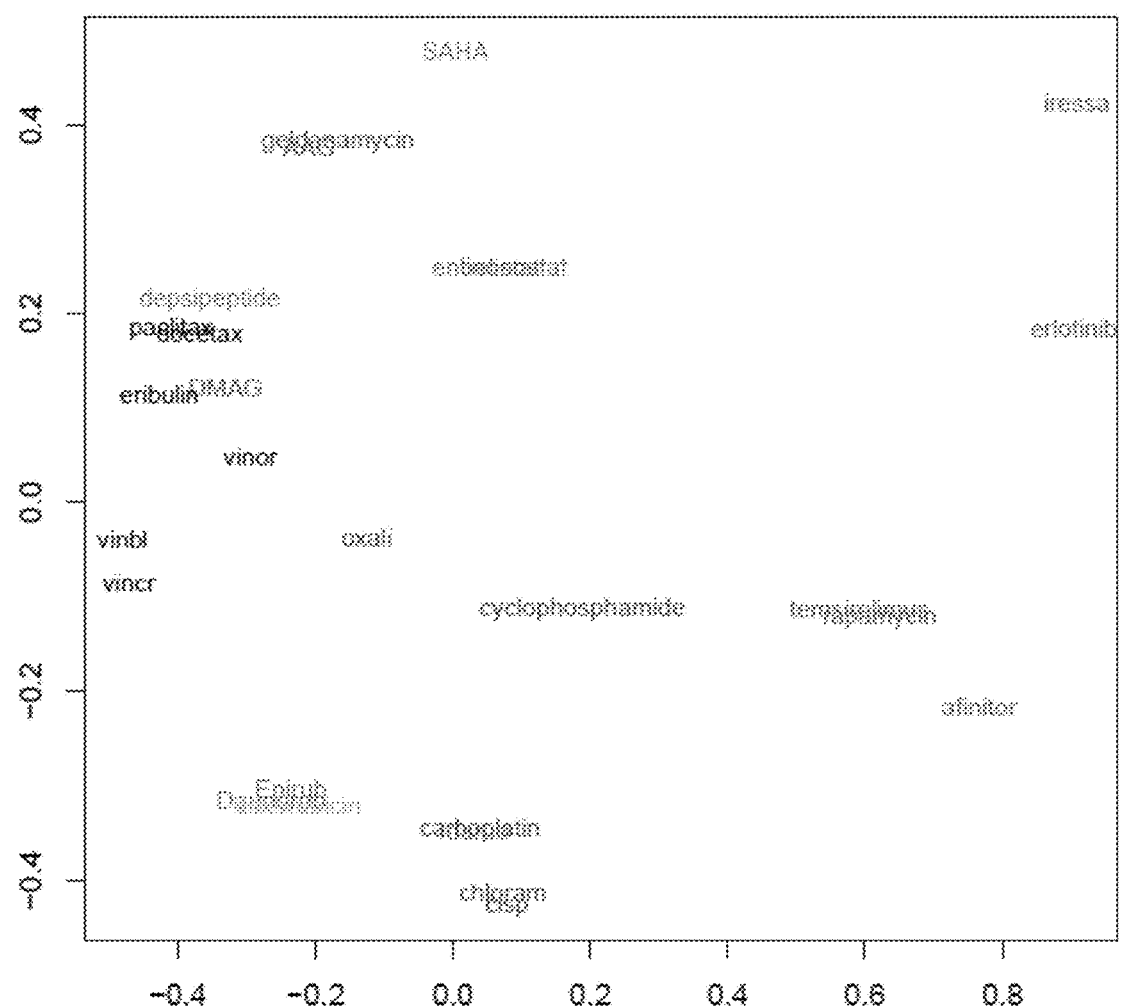
FIG. 1 is a graph showing the similarity in growth inhibition profiles of therapeutic agents in the NCI60 growth assay. A multidimensional scaling plot of the calculated similarities based on Pearson correlation between therapeutic agents is shown. Notably, doxorubicin is on top of the daunorubicin (CC=0.95) and epirubicin (CC=0.82), while idarubicin is on top of carboplatin.

I have discovered that a tumor sample of a patient with cancer (e.g., a patient having a known cancer type) may be tested by, e.g., detecting the levels of one or more of the biomarkers shown in Tables 1-4 (e.g., as single biomarkers or combinations of any two or more, or all, of the biomarkers) in the sample from the patient and used to predict the responsiveness of the patient to an anthracycline, such as doxorubicin (e.g., a doxorubicin-containing liposome), epirubicin, daunorubicin, or idarubicin. These patients may already be determined to be resistant to a therapy other than an anthracycline, such as irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

A device, such as a microarray, with one or more single-stranded oligonucleotide probes that have substantial identity (e.g., at least 85%, 90%, 95%, 99%, or 100% sequence identity) to a sequence that is complementary or identical to the nucleic acid sequence of one or more biomarkers shown in Tables 1-4 can be used according to the methods described herein to assess the responsiveness of a cancer patient to treatment with an anthracycline (e.g., doxorubicin, epirubicin, daunorubicin, or idarubicin, or an anthracycline-containing liposome, such as a doxorubicin-containing liposome (e.g., 2B3-101)). For example, the probes can be used to detect one or more (e.g., two, three, four, five, ten, twenty, or all) of the biomarkers of sensitivity listed in Tables 1 and 3, such as HSLS1 (SEQ ID NO: 1), in a sample (e.g., a tumor sample) from a patient with cancer (e.g., breast cancer). Additionally, the probes can be used to detect one or more (e.g., two, three, four, five, ten, twenty, or all) of the biomarkers of resistance listed in Tables 2 and 4, such as SFN (SEQ ID NO: 105, 106, 108, 475, 480, or 491), in a sample (e.g., a tumor sample) from a patient with cancer (e.g., breast cancer).

Accordingly, the invention features individual biomarkers selected from those shown in Tables 1-4 (e.g., HSLS1 (SEQ ID NO: 1) or SFN (SEQ ID NO: 105, 106, 108, 475, 480, or 491)) and sets of two or more of the biomarkers shown in Tables 1-4 that can be used to determine the responsiveness of a cancer patient to an anthracycline (e.g., doxorubicin, epirubicin, daunorubicin, or idarubicin, or an anthracycline-containing liposome, such as a doxorubicin-containing liposome (e.g., 2B3-101)) at various stages of disease progression (e.g., patients diagnosed with cancer or patients after cancer recurrence) and at different times during the treatment process (e.g., prior to administration of any cancer treatment, after administration of one or more cancer treatments other than anthracycline, prior to administration of the anthracycline, or during administration of the anthracycline). Additionally, the methods can be used to determine responsiveness of a cancer patient to an anthracycline that is resistant to one or more cancer therapies other than the anthracycline, such as irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, ZD1839, anastrozole, and rituximab.

In particular, the invention provides methods for determining whether a patient may be responsive to an anthracycline (e.g., doxorubicin, epirubicin, daunorubicin, or idarubicin, or an anthracycline-containing liposome, such as a doxorubicin-containing liposome (e.g., 2B3-101)) by, e.g., detecting the level (e.g., mRNA or a protein produced therefrom) of one or more of the biomarkers shown in Tables 1-4 (e.g., HSLS1 (SEQ ID NO: 1)) in a biological sample (e.g., a tumor biopsy) obtained from the subject using a device (e.g., a microarray or a protein array). The level of one or more of the biomarkers of sensitivity may then be compared to the level of the biomarker(s) in a cell or tissue known to be sensitive or resistant to the anthracycline to determine the patient's responsiveness to the anthracycline. The patient is determined to be responsive to the anthracycline if or when the level of the one or more of the biomarkers of sensitivity (e.g., one or more of HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), and SELPLG (SEQ ID NO: 15)) is substantially similar to the level of the biomarker(s) of sensitivity in a cell or tissue known to be sensitive to the anthracycline (e.g., from a patient sensitive to the anthracycline). The patient is also determined to be responsive to the anthracycline if or when the level of one or more of the biomarkers of resistance (e.g., one or more of SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124)) is substantially dissimilar to the level of the biomarker(s) of resistance in a cell or tissue known to be resistant to the anthracycline (e.g., from a patient resistant to the anthracycline).

The invention also features methods of treating a patient with cancer, such as a patient having a cancer that is resistant to one or more cancer therapies other than an anthracycline, by detecting the level(s) of one or more of the biomarker(s) shown in Tables 1-4 (e.g., HSLS1 (SEQ ID NO: 1) in a sample (e.g., a tumor sample) from the patient, and then administering the anthracycline based on the level(s) of the biomarker(s). In particular, a patient with cancer may be administered the anthracycline if the level of one or more biomarkers of sensitivity is substantially similar to the level of the biomarker(s) of sensitivity in a cell or tissue known to be sensitive to the anthracycline. Additionally, a patient with cancer may be administered the anthracycline if the level of one or more biomarkers of resistance is substantially dissimilar to the level of the biomarker(s) of resistance in a cell or tissue known to be resistant to the anthracycline. Thus, the methods can be used to treat cancer patients predicted to be responsive to the anthracycline, such as patients having, e.g., brain cancer, metastatic cancer (e.g., breast cancer that has metastasized to the brain), breast cancer (e.g., estrogen receptor-positive (ERpos) breast cancer), prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, lung cancer (e.g., non-small cell lung carcinoma (NSCLC)), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), and Hodgkin's lymphoma. Alternatively, a patient with cancer may not be administered the anthracycline if the level of one or more biomarkers of sensitivity is substantially dissimilar to the level of the biomarker(s) of sensitivity in a cell or tissue known to be sensitive to the anthracycline. Likewise, a patient with cancer may not be administered the anthracycline if the level of one or more biomarkers of resistance is substantially similar to the level of the biomarker(s) of resistance in a cell or tissue known to be resistant to the anthracycline.

Methods are described herein for identifying biomarkers of drug responsiveness, detecting levels of one or more biomarkers of sensitivity and one or more biomarkers of resistance in cancer patients, determining the responsiveness of a cancer patient to an anthracycline, and treating cancer patients with the anthracycline. Also described are devices and kits for use in these methods.

Methods for Identifying Biomarkers of Drug Responsiveness

The invention features methods for identifying biomarkers (e.g., one or more of the biomarkers of Tables 1-4) for determining the responsiveness of a cancer patient to a cancer treatment, such as an anthracycline (e.g., doxorubicin, epirubicin, daunorubicin, or idarubicin, or an anthracycline-containing liposome, such as a doxorubicin-containing liposome (e.g., 2B3-101)). Such methods can involve, for example, an algorithm based on growth inhibition values (GI50) of cell lines (e.g., NCI60 cell lines) subjected to treatment with the anthracycline, followed by measurement of gene expression (e.g., using a microarray (e.g., an Affymetrix HG-U133A or HG-U133_Plus_2 array)).

Methodology of the In Vitro Cancer Growth Inhibition Screen

The human tumor cell lines of the cancer screening panel may be grown in RPMI 1640 medium containing 5% fetal bovine serum and 2 mM L-glutamine. Cells may be inoculated into 96 well microtiter plates in 100 µL at plating densities ranging from 5,000 to 40,000 cells/well depending on the doubling time of individual cell lines. After cell inoculation, the microtiter plates may be incubated at 37° C., 5% CO2, 95% air and 100% relative humidity for 24 hours prior to addition of experimental agent (e.g., an anthracycline, such as doxorubicin, epirubicin, daunorubicin, or idarubicin, or an anthracycline-containing liposome, such as a doxorubicin-containing liposome (e.g., 2B3-101)). After 24 hours, two plates of each cell line may be fixed in situ with TCA, to represent a measurement of the cell population for each cell line at the time of agent addition (Tz). Experimental agents may be solubilized in dimethyl sulfoxide at 400-fold the desired final maximum test concentration and stored frozen prior to use. At the time of agent addition (e.g., an anthracycline, such as doxorubicin), an aliquot of frozen concentrate may be thawed and diluted to twice the desired final maximum test concentration with complete medium containing 50 µg/ml Gentamicin. A total of four additional 10-fold or ½ log serial dilutions are made to provide a total of five concentrations plus control. Aliquots of 100 µl of these different agent dilutions are added to the appropriate microtiter wells already containing 100 µl of medium, resulting in the required final agent concentrations.

Following agent addition (e.g., an anthracycline, such as doxorubicin, epirubicin, daunorubicin, or idarubicin, or an anthracycline-containing liposome, such as a doxorubicin-containing liposome (e.g., 2B3-101)), the plates may be incubated for an additional 48 h at 37° C., 5% CO2, 95% air, and 100% relative humidity. For adherent cells, the assay may be terminated by the addition of cold TCA. Cells may be fixed in situ by the gentle addition of 50 µl of cold 50% (w/v) TCA (final concentration, 10% TCA) and incubated for 60 minutes at 4° C. The supernatant may be discarded, and the plates may be washed five times with tap water and air-dried. Sulforhodamine B (SRB) solution (100 µl) at 0.4% (w/v) in 1% acetic acid may be added to each well, and the plates may be incubated for 10 minutes at room temperature. After staining, unbound dye may be removed by washing five times with 1% acetic acid and the plates may be air-dried. Bound stain may be subsequently solubilized with 10 mM trizma base, and the absorbance may be read on an automated plate reader at a wavelength of 515 nm. For suspension cells, the methodology may be the same, except that the assay may be terminated by fixing settled cells at the bottom of the wells by gently adding 50 µl of 80% TCA (final concentration, 16% TCA). Using the seven absorbance measurements [time zero, (Tz), control growth, (C), and test growth in the presence of agent (e.g., the anthracycline) at the five concentration levels (Ti)], the percentage growth may be calculated at each of the agent concentration levels. Percentage growth inhibition may be calculated as:

$$[(Ti-Tz)/(C-Tz)] \times 100 \text{ for concentrations for which } Ti >/= Tz$$

$$[(Ti-Tz)/Tz] \times 100 \text{ for concentrations for which } Ti < Tz$$

Three dose response parameters may be calculated for each experimental agent (e.g., the anthracycline). Growth inhibition of 50% (GI50) is calculated from [(Ti−Tz)/(C−Tz)]×100=50, which is the agent (e.g., an anthracycline, such as doxorubicin, epirubicin, daunorubicin, or idarubicin, or an anthracycline-containing liposome, such as a doxorubicin-containing liposome (e.g., 2B3-101)) concentration resulting in a 50% reduction in the net protein increase (as measured by SRB staining) in control cells during incubation with the test agent. The agent concentration resulting in total growth inhibition (TGI) is calculated from Ti=Tz. The LC50 (concentration of the agent, such as anthracycline (e.g., doxorubicin, epirubicin, daunorubicin, or idarubicin), resulting in a 50% reduction in the measured protein at the end of the compound treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

Gene Expression and Growth Inhibition Analysis

The gene expression measurements of NCI60 cancer cell lines can be obtained from a publically available database (e.g., the National Cancer Institute and the Massachusetts Institute of Technology). Each dataset can be normalized so that sample expression measured by different chips can be compared. The preferred method of normalization is the logit transformation, which may be performed for each gene y on each chip, as follows:

$$\text{logit}(y) = \log[(y - \text{background})/(\text{saturation} - y)],$$

where background is calculated as the minimum intensity measured on the chip minus 0.1% of the signal intensity range: min−0.001*(max−min), and saturation is calculated as the maximum intensity measured on the chip plus 0.1% of the signal intensity range: max+0.001*(max−min). The resulting logit transformed data may then be z-transformed to mean zero and standard deviation 1.

Next, gene expression can be correlated to cancer cell growth inhibition. Growth inhibition data (GI50) of the NCI60 cell lines in the presence of a cancer treatment, such as an anthracycline (e.g., doxorubicin, epirubicin, daunorubicin, or idarubicin, or an anthracycline-containing liposome, such as a doxorubicin-containing liposome (e.g., 2B3-101)), can be obtained from the NCI. The correlation between the logit-transformed expression level of each gene in each cell line and the logarithm of GI50 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given treatment (e.g., an anthracycline, such as doxorubicin or a doxorubicin-containing liposome (e.g., 2B3-101)) may be correlated to gene expression levels of the patient. Since a plurality of measurements may be available for a single gene, the most accurate determination of correlation coefficient can be, e.g., the median of the correlation coefficients calculated for all probes measuring expression of the same gene.

For example, the median correlation coefficient of gene expression measured on a probe to growth inhibition or patient sensitivity to an anthracycline (e.g., doxorubicin, epirubicin, daunorubicin, or idarubicin, or an anthracycline-containing liposome, such as a doxorubicin-containing liposome (e.g., 2B3-101)) can be calculated for all genes of interest. Genes that have a median correlation above about 0.20 (e.g., above 0.21 0.22. 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, or higher (e.g., 0.3 or higher)), can be used as biomarkers of sensitivity for assessing responsiveness of a cancer patient to the anthracycline (e.g., a patient with cancer that is resistant to one or more cancer therapies other than the anthracycline and/or has an unknown responsiveness to anthracycline).

Likewise, genes that have a median correlation below about −0.20 (e.g., below −0.21, −0.22. −0.23, −0.24, −0.25, −0.26, −0.27, −0.28, −0.29, −0.30, −0.31, −0.32, −0.33, −0.34, −0.35, −0.36, −0.37, −0.38, −0.39, −0.40, or lower (e.g., −0.3 or lower)), can be used as biomarkers of resistance for assessing responsiveness of a cancer patient to the anthracycline (e.g., a patient with cancer that is resistant to one or more cancer therapies other than the anthracycline and/or has an unknown responsiveness to anthracycline). Preferably, the correlation coefficient of a biomarker of sensitivity will exceed 0.2, while the correlation coefficient of a biomarker of resistance will be less than −0.2. The result is a list of biomarker genes that correlate to sensitivity or resistance to an anthracycline, as shown in Tables 1 and 3 and Tables 2 and 4, respectively.

Cancer Types

The methods, devices, and kits of the invention can be used for prognosing, monitoring, treating, and/or reducing cancer in a subject suffering from, diagnosed with, or susceptible to cancer. Non-limiting examples of cancers that can be prognosed, monitored, treated (e.g., by administering an anthracycline, such as doxorubicin, epirubicin, daunorubicin, or idarubicin), or reduced using the methods include hematological and solid tumors. In particular, cancers include, e.g., brain cancer (e.g., astrocytoma, glioblastoma multiforme, and craniopharyngioma), metastatic cancer (e.g., breast cancer that has metastasized to the brain), breast cancer (e.g., an estrogen receptor-positive (ERpos) breast cancer or a metastatic form of breast cancer), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system.

In particular, the methods are useful for prognosing, monitoring, treating, or preventing, e.g., brain cancer, breast cancer (e.g., an ERpos breast cancer or a metastatic form of breast cancer), prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), and Hodgkin's lymphoma. For example, the cancer can be breast cancer, such as Stage 0, Stage I, Stage II, Stage III, or Stage IV breast cancer. In particular, the cancer may be breast cancer that is resistant to one or more cancer therapies other than an anthracycline, such as cyclophosphamide, fluorouracil (5-FU), methotrexate, cisplatin, docetaxel, paclitaxel, cisplatin, docetaxel, carboplatin, trastuzumab, vinorelbine, radiation, and/or surgery. For instance, the breast cancer is medullary carcinoma. The breast cancer may also be, e.g., a metastatic form of breast cancer.

Methods for Detecting Biomarker Levels in Cancer Patients

A cancer patient can be assessed for sensitivity or resistance to an anthracycline (e.g., doxorubicin, epirubicin, daunorubicin, or idarubicin, or an anthracycline-containing liposome, such as a doxorubicin-containing liposome (e.g., 2B3-101)) by detecting a level of a biomarker (e.g., one or more of the biomarkers of Tables 1-4) in a biological sample obtained from the cancer patient (e.g., a patient with cancer that is resistant to one or more cancer therapies other than an anthracycline and/or has an unknown responsiveness to an anthracycline). The biological sample can include, for example, cells, tissue (e.g., a tissue sample obtained by biopsy), blood, serum, plasma, urine, sputum, cerebrospinal fluid, lymph tissue or fluid, or pancreatic fluid. For example, the biological sample can be fresh frozen or formalin-fixed paraffin embedded (FFPE) tissue obtained from the subject, such as a tumor sample (e.g., a biopsy) from the tissue of interest (e.g., prostate, ovarian, lung, lymph nodes, thymus, spleen, bone marrow, breast, colorectal, pancreatic, cervical, bladder, gastrointestinal, head, or neck tissue).

RNA Extraction and Measurement of Biomarker Levels

Cell samples or tissue samples may be snap frozen in liquid nitrogen until processing. RNA may be extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. or a compatible apparatus, e.g., the GCS3000Dx GeneChip® System from Affymetrix Inc., using the manufacturer's instructions. The resulting biomarker level measurements may be further analyzed as described herein. The procedures described can be implemented using, e.g., R software available from R-Project (www.r-project.org) and supplemented with packages available from Bioconductor (www.bioconductor.org).

The level of one or more of the biomarkers shown in Tables 1-4 (e.g., HSLS1 (SEQ ID NO: 1)) may be measured in a biological sample (e.g., a tumor sample) obtained from the cancer patient (e.g., a patient with any of the cancer types described herein, such as a patient with cancer that is resistant to one or more cancer therapies and/or has an unknown responsiveness to an anthracycline) using, e.g., polymerase chain reaction (PCR), reverse transcriptase PCR (RT-PCR), quantitative real-time PCR (qRT-PCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies (e.g., those described in U.S. Patent Application Nos. US 2011/0201515, US 2011/0229888, and US 2013/0017971, each of which is incorporated by reference in its entirety), proteomic techniques (e.g., mass spectrometry or protein arrays), and combinations thereof.

Devices

Devices of the invention can be used for detecting a level of one or more biomarkers shown in Tables 1-4. The device may include at least one (or one type of) single-stranded nucleic acid (e.g., a probe) having at least 85% sequence identity (e.g., 85%, 90%, 95%, 97%, 98%, 99%, or 100% sequence identity) to a nucleic acid sequence that is complementary or identical to at least 5 (e.g., at least 10, at least 15, at least 20, or more) consecutive nucleotides of one or more biomarkers shown in Tables 1-4 (e.g., HSLS1 (SEQ ID NO: 1) or SFN (SEQ ID NO: 105, 106, 108, 475, 480, or 491)), in which the at least one single-stranded nucleic acid is sufficient for the detection of the level of the one or more biomarkers. The device may be used to detect the level of a given biomarker by specific hybridization between the single-stranded nucleic acid and the biomarker (e.g., an mRNA, genomic DNA, or noncoding RNA), a nucleic acid of the biomarker (e.g., an mRNA), or a complementary nucleic acid thereof. The device may be or include a microarray. The device may also include or be used with reagents and materials for next generation sequence (e.g., sequencing by synthesis). The device may also include or be used with NanoString reagents and at least one nCounter cartridge. The device may be or include a protein array, which contains one or more protein binding moieties (e.g., proteins, antibodies, nucleic acids, aptamers, affibodies, lipids, phospholipids, small molecules, labeled variants of any of the above, and any other moieties useful for protein detection as well known in the art) capable of detectably binding to the polypeptide product(s) of one or more biomarkers shown in Tables 1-4. The device may also be a cartridge for measuring an amplification product resulting from hybridization between one or more nucleic acid molecules from the patient and at least one single-stranded nucleic acid single-stranded nucleic acid molecules of the device, such as a device for performing qRT-PCR.

Microarrays

The level(s) of the biomarker(s) (e.g., the biomarkers listed in Tables 1-4, such as, (e.g., HSLS1 (SEQ ID NO: 1)) may be determined using high-throughput expression profiling platforms, such as microarrays. In particular, a microarray for use in the methods for assessing the responsiveness of a cancer patient to an anthracycline (e.g., a patient with cancer that is resistant to one or more cancer therapies and/or has an unknown responsiveness to an anthracycline, such as doxorubicin, epirubicin, daunorubicin, or idarubicin, or an anthracycline-containing liposome, such as a doxorubicin-containing liposome (e.g., 2B3-101)) contains or is produced by generating oligonucleotide probes (e.g., DNA, cDNA, or RNA probes) capable of hybridizing to one or more biomarkers of interest (e.g., one or more of the biomarkers of Tables 1-4) or the complement sequences thereof. Each probe can have, e.g., at least 10, 15, 20, 25, 30, or more contiguous nucleic acid residues (e.g., at least 15) that are complementary or identical to a nucleic acid sequence of a selected biomarker. The probe nucleic acid sequence can also have at least 85% (e.g., 90%, 95%, 99%, or 100%) sequence identity to the nucleic acid sequence of the gene coding the biomarker (e.g., HSLS1 (SEQ ID NO: 1)) or the complement sequence thereof. In particular, the probe sequences can be complementary to all or a portion of the nucleic acid sequence of the biomarker(s).

For example, microarrays of the invention for determining responsiveness to an anthracycline (e.g., doxorubicin, epirubicin, daunorubicin, or idarubicin, or an anthracycline-containing liposome, such as a doxorubicin-containing liposome (e.g., 2B3-101)) can include probes for one or more (e.g., at least 5, 10, 15, or 20 or more (e.g., all)) biomarkers of sensitivity shown in Tables 1 and 3, such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ARHGAP15 (SEQ ID NO: 10), CD99 (SEQ ID NO: 12 or 31), SRSF7 (SEQ ID NO: 13), SELPLG (SEQ ID NO: 15), SFRS7 (SEQ ID NO: 19 or 54), or CAP350 (SEQ ID NO: 20 or 61). Microarrays for determining responsiveness to the anthracycline can also include probes for one or more (e.g., at least 5, 10, 15, or 20 or more (e.g., all)) biomarkers of resistance listed in Tables 2 and 4, such as SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124).

Microarrays for determining responsiveness to an anthracycline (e.g., doxorubicin, epirubicin, daunorubicin, or idarubicin, or an anthracycline-containing liposome, such as a doxorubicin-containing liposome (e.g., 2B3-101)) can also include probes for one or more (e.g., at least 5, 10, 15, or 20 or more (e.g., all)) biomarkers of sensitivity and biomarkers of resistance shown in Tables 1-4, such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124).

A microarray probe may be single-stranded or double-stranded. The probe may be labeled (e.g., detectably labeled with a fluorescent molecule, dye molecule, small molecule, epitope tag, barcode sequence, polypeptide, or any other detectable molecule). Probes can be detectably labeled and immobilized on a solid support to form the microarray. Additionally, probes can be detectably labeled and included in, e.g., a tube, such as probes labeled with a fluorescent molecule. For example, probes can be either prefabricated and spotted to the surface or directly synthesized on to the surface (in situ) of the microarray. The microarray can also be configured such that the sequence and position of each member (e.g., probe) of the array is known. For example, a selection of biomarkers whose levels correlates with an increased likelihood of responsiveness to anthracycline can be arrayed on a solid support. Hybridization of a labeled probe with a particular target nucleic acid (e.g., an mRNA corresponding to one or more biomarkers of Tables 1-4) indicates that the sample from which the mRNA was derived expresses that biomarker (e.g., the biomarker of sensitivity or resistance to an anthracycline).

PCR-Based Techniques

As few as one to thirty (e.g., 5 to 30 or 10 to 30, or at least the first 15 of the biomarkers listed in Tables 1-4) biomarkers may be used to determine patient responsiveness to an anthracycline using the methods described herein. Tissue or cell samples from a cancer patient (e.g., a patient with a known cancer type that is resistant to one or more cancer therapies and/or has an unknown responsiveness to an anthracycline) can be conveniently assayed for levels using PCR analysis, such as quantitative real-time PCR (qRT-PCR), or quantitative loop-mediated isothermal amplification (q-LAMP). For example, an mRNA corresponding to a biomarker of Tables 1-4 can be detected in a biological sample by (a) producing cDNA from the sample by reverse transcription using at least one primer; (b) amplifying the cDNA so produced using a target polynucleotide as sense and antisense primers to amplify target cDNAs therein; and (c) detecting the presence of the amplified target cDNA using polynucleotide probes. The primers and probes including the target sequences shown in Tables 1-4, such as HSLS1 (SEQ ID NO: 1) and/or SFN (SEQ ID NO: 105, 106, 108, 475, 480, or 491), may be used to detect the level(s) of one or more of the indicated biomarkers using PCR. The methods can include one or more steps that allow determination of the levels of target mRNA in a biological sample (e.g., by simultaneously examining the levels of a comparative control mRNA sequence or "housekeeping" gene, such as an actin family member or GAPDH). The primers for these PCR-based assays may be labeled for detection according to methods known in the art.

Sequencing

The levels of the biomarkers shown in Tables 1-4, such as HSLS1 (SEQ ID NO: 1), SFN (SEQ ID NO: 105, 106, 108, 475, 480, or 491), may be determined using sequencing technologies, such as next generation sequencing platforms (e.g., RNA-Seq), as described in Mortazavi et al., *Nat. Methods* 5: 621-628, 2008, hereby incorporated by reference. RNA-Seq is a robust technology for monitoring biomarker levels by direct sequencing of the RNA molecules in a sample. This methodology may include fragmentation of RNA to an average length of, e.g., 200 nucleotides, conversion to cDNA by random priming, and synthesis of double-stranded cDNA (e.g., using the PROTOSCRIPT® First Strand cDNA Synthesis Kit from New England Biosciences). The cDNA may then be converted into a molecular library for sequencing by addition of sequence adapters for each library (e.g., from ILLUMINA®/Solexa), and the resulting 50 to 100 nucleotide reads are mapped onto the genome. Exemplary sequencing platforms suitable for use according to the methods include, e.g., pyrosequencing, ILLUMINA® sequencing by synthesis, SOLID® sequencing, ION TORRENT® sequencing, and SMRT® sequencing.

Methods of Determining Patient Responsiveness to an Anthracycline

The invention features diagnostic methods for the detection and screening of cancer patients that may be responsive to an anthracycline (e.g., a patient with a known cancer type that is resistant to one or more cancer therapies and/or has an unknown responsiveness to an anthracycline (e.g., doxorubicin, epirubicin, daunorubicin, or idarubicin, or an anthracycline-containing liposome, such as a doxorubicin-containing liposome (e.g., 2B3-101)) using one or more of the biomarkers shown in Tables 1-4 (e.g., HSLS1 (SEQ ID NO: 1) or SFN (SEQ ID NO: 105, 106, 108, 475, 480, or 491)). The methods of the invention may be used for predicting a patient's responsiveness to the anthracycline, and optionally, treating the cancer patient throughout the progression of cancer and/or in cases of recurrence (e.g., after a first line treatment, a second line treatment, and/or a third line treatment).

The invention provides individual biomarkers (e.g., HSLS1 (SEQ ID NO: 1) and sets of biomarkers (e.g., two or more of the biomarkers listed in Tables 1-4)), the levels of which, as detected in a biological sample (e.g., a tumor sample, such as a biopsy) obtained from a cancer patient (e.g., a human with cancer), are indicative of responsiveness to an anthracycline (e.g., doxorubicin, epirubicin, daunorubicin, or idarubicin, or an anthracycline-containing liposome, such as a doxorubicin-containing liposome (e.g., 2B3-101)). The biomarkers were identified using methods similar to those previously described in, e.g., Chen et al. (*Mol. Cancer Ther.* 11:34-33, 2012), Wang et al. (*J. Nat. Cancer Inst.* 105: 1284-1291, 2013), and Knudsen et al. (*PLoS One,* 9: e87415, 2014), each of which are incorporated by reference herein in their entirety.

In particular, an algorithm based on growth inhibition values (GI50) of a cell line (e.g., NCI60 cells) subjected to treatment with an anthracycline (e.g., doxorubicin, epirubicin, daunorubicin, or idarubicin, or an anthracycline-containing liposome, such as a doxorubicin-containing liposome (e.g., 2B3-101)) and gene expression is determined (e.g., by microarray analysis, reverse transcriptase polymerase chain reaction (RT-PCR), quantitative real-time PCR (qPCR), or next generation sequencing). After normalization, genes with, e.g., a Pearson correlation coefficient greater than about 0.2 or below about −0.2 can be classified as biomarkers of sensitivity or resistance, respectively. In particular, a correlation coefficient of about 0.2 or greater is a statistically significant cut-off known in the art for establishing whether the levels of the biomarker, e.g., the biomarkers shown in Tables 1-4, correlate with the likelihood of cancer treatment sensitivity, such as sensitivity to the anthracycline. Thus, a correlation coefficient of about 0.2 or greater or about −0.2 or lower can be used to identify biomarkers, such as the biomarkers of Tables 1-4, for predicting patient responsiveness to treatment with the anthracycline according to the methods described herein.

Comparison of Biomarker Levels

One or more biomarkers of sensitivity and/or resistance, identified as described herein, can be used to predict responsiveness to an anthracycline (e.g., doxorubicin, epirubicin, daunorubicin, or idarubicin, or an anthracycline-containing liposome, such as a doxorubicin-containing liposome (e.g., 2B3-101)) by measuring the level of the biomarkers in a biological sample obtained from a cancer patient (e.g., a patient with a solid tumor or hematological cancer) in a sample (e.g., a tumor sample) obtained from the cancer patient. A single biomarker (e.g., any of the biomarkers of Tables 1-4, such as HSLS1 (SEQ ID NO: 1) or SFN (SEQ ID NO: 105, 106, 108, 475, 480, or 491)) may be used to determine the responsiveness of a cancer patient to the anthracycline (e.g., a patient with a known cancer type that is resistant to one or more cancer therapies and/or has an unknown responsiveness to an anthracycline).

For instance, after determining the level of a biomarker(s) of sensitivity (e.g., any of the biomarkers of Tables 1 and 3, such as HSLS1 (SEQ ID NO: 1)) in a sample (e.g., a tumor sample) from the cancer patient, the level of the biomarker(s) of sensitivity in the sample may be compared to the level of the biomarker(s) of sensitivity in a cell (e.g., a cancer cell) or tissue (e.g., a tumor tissue) known to be sensitive to treatment with the anthracycline. If the level of the biomarker(s) of sensitivity in the sample from the cancer patient is substantially similar (e.g., identical to, corresponds to, or has the same trend of level) to the level of the biomarker(s) of sensitivity in the cell or tissue known to be sensitive to the anthracycline, then the cancer patient is predicted to be responsive to treatment with the anthracycline. Alternatively, if the level of the biomarker(s) of sensitivity in the sample from the cancer patient is substantially dissimilar to the level of the biomarker(s) of sensitivity in the cell or tissue known to be sensitive to an anthracycline, then the cancer patient is predicted to be non-responsive to treatment with the anthracycline.

The level of the biomarker(s) of sensitivity (e.g., any of the biomarkers of Tables 1 and 3, such as HSLS1 (SEQ ID NO: 1)) in a sample (e.g., a tumor sample) from the cancer patient may also be compared to the level of the biomarker(s) of sensitivity in a cell (e.g., a cancer cell) or tissue (e.g., a tumor tissue) known to be resistant to treatment with an anthracycline (e.g., doxorubicin, epirubicin, daunorubicin, or idarubicin, or an anthracycline-containing liposome, such as a doxorubicin-containing liposome (e.g., 2B3-101)). If the level of the biomarker(s) of sensitivity in the sample from the cancer patient is substantially similar to the level of the biomarker(s) of sensitivity in the cell or tissue known to be resistant to the anthracycline, then the cancer patient is predicted to be non-responsive to treatment with the anthracycline. Alternatively, if the level of the biomarker(s) of sensitivity in the sample from the cancer patient is substantially dissimilar to the level of the biomarker(s) of sensitivity in the cell or tissue known to be resistant to the anthracycline, then the cancer patient is predicted to be responsive to treatment with the anthracycline.

For instance, after determining the level of a biomarker(s) of resistance (e.g., any of the biomarkers of Tables 2 and 4, such as SFN (SEQ ID NO: 105, 106, 108, 475, 480, or 491)) in a sample (e.g., a tumor sample) from a cancer patient (e.g., a patient with a solid tumor or hematological cancer), the level of the biomarker of resistance in the sample from the cancer patient may also be compared to the level of the biomarker(s) of resistance in a cell (e.g., a cancer cell) or tissue (e.g., a tumor tissue) known to be resistant to treatment with an anthracycline (e.g., doxorubicin, epirubicin, daunorubicin, or idarubicin, or an anthracycline-containing liposome, such as a doxorubicin-containing liposome (e.g., 2B3-101)). If the level of the biomarker(s) of resistance in the sample from the cancer patient is substantially similar to the level of the biomarker(s) of resistance in the cell or tissue known to be resistant to anthracycline, then the cancer patient is predicted to be non-responsive to treatment with the anthracycline. Alternatively, if the level of the biomarker(s) of resistance in the sample from the cancer patient is substantially dissimilar to the level of the biomarker(s) of resistance in the cell or tissue known to be resistant to an anthracycline, then the cancer patient is predicted to be responsive to treatment with the anthracycline.

The level of a biomarker(s) of resistance (e.g., any of the biomarkers of Tables 2 and 4, such as SFN (SEQ ID NO: 105, 106, 108, 475, 480, or 491)) in a sample (e.g., a tumor sample) from a cancer patient (e.g., a patient with a solid tumor or hematological cancer) may be compared to the level of the biomarker(s) of resistance in a cell (e.g., a cancer cell) or tissue (e.g., a tumor tissue) known to be sensitive to treatment with an anthracycline (e.g., doxorubicin, epirubicin, daunorubicin, or idarubicin, or an anthracycline-containing liposome, such as a doxorubicin-containing liposome (e.g., 2B3-101)). If the level of the biomarker(s) of resistance in the sample from the cancer patient is substantially similar (e.g., identical to, corresponds to, or has the same trend of level) to the level of the biomarker(s) of resistance in the cell or tissue known to be sensitive to the anthracycline, then the cancer patient is predicted to be responsive to treatment with the anthracycline. Alternatively, if the level of the biomarker(s) of resistance in the sample from the cancer patient is substantially dissimilar to the level of the biomarker(s) of resistance in the cell or tissue known to be sensitive to the anthracycline, then the cancer patient is predicted to be responsive to treatment with the anthracycline.

The responsiveness of a cancer patient to an anthracycline (e.g., a patient with a known cancer type that is resistant to one or more cancer therapies and/or has an unknown responsiveness to an anthracycline, such as, e.g., doxorubicin, epirubicin, daunorubicin, or idarubicin, or an anthracycline-containing liposome, such as a doxorubicin-containing liposome (e.g., 2B3-101)) can also be predicted by comparing the level of a biomarker (e.g., HSLS1 (SEQ ID NO: 1)) to the level of the biomarker in one or more cells or tissues (e.g., from a cancer patient population) known to be sensitive to treatment with the anthracycline and one or more cells or tissues (e.g., from a cancer patient population) known to be resistant to treatment with the anthracycline. In particular, the patient may be determined to be responsive to treatment with an anthracycline if the level of the biomarker(s) is more similar to the level of the biomarker(s) in cells or tissues known to be sensitive to treatment with the anthracycline than to a cell or tissue known to be resistant to treatment with the anthracycline. Alternatively, the patient may be determined to be non-responsive to treatment with an anthracycline if the level of the biomarker(s) is more similar to the level of the biomarker(s) in cells or tissues known to be resistant to treatment with the anthracycline than to a cell or tissue known to be sensitive to treatment with the anthracycline.

Additionally, one or more biomarkers of sensitivity (e.g., one or more of HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15)) and one or more biomarkers of resistance (e.g., one or more of SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124)) may be used in combination to determine the responsiveness of a cancer patient to treatment with an anthracycline (e.g., a patient with a known cancer type that is resistant to one or more cancer therapies and/or has an unknown responsiveness to an anthracycline). For example, the predicted responsiveness of a cancer patient may be determined from, e.g., the difference score, which may be defined as the difference between the mean expression levels of a plurality of the biomarkers of sensitivity of Tables 1 and 3 (e.g., one, two, three, four, five, ten, twenty, or all of the biomarkers shown in Tables 1 and 3, such as HSLS1 (SEQ ID NO: 1) and the mean expression levels of a plurality of the biomarkers of resistance of Tables 2 and 4 (e.g., one, two, three, four, five, ten, twenty, or all of the biomarkers shown in Tables 2 and 4, such as SFN (SEQ ID NO: 105, 106, 108, 475, 480, or 491)). Thus, the difference score may be calculated by subtracting the mean expression levels of a plurality of the biomarkers of resistance from the mean expression levels of a plurality of the biomarkers of sensitivity.

The difference score of the cancer patient can then be compared to a difference score based on the expression level of the biomarkers in a patient (e.g., a patient with cancer, such as a patient with a solid tumor or hematological cancer) known to be sensitive or resistant to treatment with an anthracycline (e.g., doxorubicin, epirubicin, daunorubicin, or idarubicin, or an anthracycline-containing liposome, such as a doxorubicin-containing liposome (e.g., 2B3-101)). In particular, the patient may be determined to be responsive to treatment with the anthracycline if the difference score is substantially similar to a difference score of a patient known to be sensitive to treatment with the anthracycline. Alternatively, the patient may be determined to be non-responsive to treatment with an anthracycline if the difference score is substantially similar to a difference score of a patient known to be resistant to treatment with the anthracycline. Additionally, the patient may be determined to be responsive to treatment with the anthracycline if the difference score is substantially similar to a difference score of a patient known to be sensitive to treatment with the anthracycline relative to a difference score of a patient known to be resistant to treatment with the anthracycline. Alternatively, the patient may be determined to be non-responsive to treatment with the anthracycline if the difference score is substantially similar to a difference score of a patient known to be resistant to treatment with the anthracycline relative to a difference score of a patient known to be sensitive to treatment with the anthracycline.

For example, a patient with cancer (e.g., a patient with a known cancer type that is resistant to one or more cancer therapies and/or has an unknown responsiveness to an anthracycline) may be responsive to treatment with an anthracycline (e.g., doxorubicin, epirubicin, daunorubicin, or idarubicin, or an anthracycline-containing liposome, such as a doxorubicin-containing liposome (e.g., 2B3-101)) if the difference score (e.g., the difference between mean expression levels of a plurality of the biomarkers of sensitivity of Tables 1 and 3 and mean expression levels of a plurality of the biomarkers of resistance of Tables 2 and 4) corresponds to a difference score of a patient known to be sensitive to treatment with the anthracycline. Alternatively, the patient may be non-responsive to treatment with the anthracycline if the difference score corresponds to a difference score of a patient known to be resistant to treatment with the anthracycline. Additionally, the patient may be determined to be responsive to treatment with the anthracycline if the difference score corresponds to a difference score of a patient known to be sensitive to treatment with the anthracycline relative to a difference score of a patient known to be resistant to treatment with the anthracycline. Alternatively, the patient may be determined to be non-responsive to treatment with the anthracycline if the difference score corresponds to a difference score of a patient known to be resistant to treatment with the anthracycline relative to a difference score of a patient known to be sensitive to treatment with the anthracycline.

Preferably, the cell or tissue known to be either sensitive or resistant to an anthracycline is of the same cancer type as the cancer patient with an unknown responsiveness to the anthracycline (e.g., a patient with a known cancer type that is resistant to one or more cancer therapies). For example, the cancer patient and the cell or tissue known to be either sensitive or resistant to an anthracycline may both have a cancer type selected from a solid tumor or a hematological cancer, e.g., brain cancer (e.g., astrocytoma, glioblastoma multiforme, and craniopharyngioma), metastatic cancer (e.g., breast cancer that has metastasized to the brain), breast cancer (e.g., an estrogen receptor-positive (ERpos) breast cancer or a metastatic form of breast cancer), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), stomach cancer, intra-epithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient and the cell or tissue with known resistance or sensitivity to anthracycline is, e.g., breast cancer (e.g., ERpos breast cancer and/or a metastatic form of breast cancer), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN).

Machine learning techniques such as Neural Networks, Support Vector Machines, K Nearest Neighbor, and Nearest Centroids may also be employed to develop models that discriminate patients sensitive to treatment with anthracycline from those resistant to treatment with the anthracycline using biomarker levels as model variables which assign each patient a classification as sensitive or resistant to treatment with an anthracycline (e.g., doxorubicin, epirubicin, daunorubicin, or idarubicin, or an anthracycline-containing liposome, such as a doxorubicin-containing liposome (e.g., 2B3-101)). Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; V. Tresp et al., "Neural Network Modeling of Physiological Processes," in Hanson S. J. et al. (Eds.), Computational Learning Theory and Natural Learning Systems 2, MIT Press, 1994, each of which are hereby incorporated by reference in their entirety.

Biomarkers of Sensitivity and Resistance

The biomarkers of Tables 1 and 2 were identified as biomarkers of sensitivity and resistance to doxorubicin, respectively. The biomarkers of Tables 3 and 4 were identified as biomarkers of sensitivity and resistance to epirubicin, respectively. Given the structural similarities of anthracycline compounds and the results provided herein in Examples 1 and 4, the expression levels of one or more of the biomarkers of Tables 1-4 can be used to determine cancer patient responsiveness to treatment with a range of anthracyclines, such as doxorubicin and epirubicin or a liposomal formulation thereof (e.g., a doxorubicin containing-liposome, such as 2B3-101), and also including daunorubicin and idarubicin. Once determined to be responsive using the methods of the invention, the patient can be treated with an anthracycline (e.g., doxorubicin, epirubicin, daunorubicin, or idarubicin, or an anthracycline-containing liposome, such as a doxorubicin-containing liposome (e.g., 2B3-101)) alone or the anthracycline and one or more of the other therapies described herein.

TABLE 1 mRNA biomarkers of sensitivity to doxorubicin. Affymetrix IDs refer to the array type HG-U133A.

| Gene | Affymetrix ID | Correlation | Affymetrix Probe Sequence | SEQ ID NO: |
|---|---|---|---|---|
| HCLS1 | 202957_at | 0.458 | TGATGAGCTTTCCTTTGATCCGGAC | 1 |
| PTPRCAP | 204960_at | 0.381 | CCTCCATGTCACCGCACTGTAGAGG | 2 |
| NEIL3 | 219502_at | 0.371 | ATTCTCTGGCATTTAGTCTCTTCAA | 3 |
| PTPRC | 212587_s_at | 0.357 | AAGTGTGCAGAATACTGGCCGTCAA | 4 |
| IFI16 | 208965_s_at | 0.355 | CCCTCCACAAGCAGCACTGTCAAAA | 5 |
| RHOH | 204951_at | 0.354 | CTACAAGTGAACTCCTTGCCCAGGC | 6 |
| SSBP2 | 203787_at | 0.341 | ACACATACATACATTGACCCACAGG | 7 |
| CD2 | 205831_at | 0.341 | TCCCCTCTCAGGTCATGTGTAGATG | 8 |
| ITGA4 | 213416_at | 0.34 | ATTCTTTTTGGCAGGTAGGCTATA | 9 |
| ARHGAP15 | 218870_at | 0.34 | ACCTCATGTCCACGCAAAGCTTGGG | 10 |
| SRPK2 | 203182_s_at | 0.338 | GCAGGTTGCACACAGTTTTGTTTAT | 11 |

TABLE 1-continued mRNA biomarkers of sensitivity to doxorubicin. Affymetrix IDs refer to the array type HG-U133A.

| Gene | Affymetrix ID | Correlation | Affymetrix Probe Sequence | SEQ ID NO: |
|---|---|---|---|---|
| DD99 | 201028_s_at | 0.336 | TGGAGAAAATGACGACCCACGACCA | 12 |
| SRSF7 | 213649_at | 0.334 | ATCATGCTGAGGCGCCTTGCAAATC | 13 |
| CTCF | 202521_at | 0.333 | AGAGAGCCTCAGTCTTACTGATTTC | 14 |
| SELPLG | 209879_at | 0.332 | TCCATCTAGTGACAAGTGACCCCCA | 15 |
| LAT | 211005_at | 0.332 | AGAGATTTGGAGATGTCTCTGTGTG | 16 |
| CEP350 | 213165_at | 0.332 | GTTTAATAGCTTTTCCTTCTGGACT | 17 |
| NCKAP1L | 209734_at | 0.33 | CCTGCTTCGAAATGCCTATCGGGAG | 18 |
| CYFIP2 | 220999_s_at | 0.326 | GGTGACATATTTACGCTTGTGATCA | 19 |
| PTPRC | 207238_s_at | 0.325 | GAACAGTTTGTACAGACGTATGCTT | 20 |
| CD3D | 213539_at | 0.325 | GAATCTACCGTGCAAGTTCATTATC | 21 |
| CYFIP2 | 215785_s_at | 0.322 | GGATCCAACTGGACAACGTGTGGGA | 22 |
| IKZF1 | 205038_at | 0.321 | CTCATCACATTATCATTGCATATCA | 23 |
| CUTC | 218970_s_at | 0.32 | GTCTGTGCTTCTTCCATAGACAGAA | 24 |
| CD53 | 203416_at | 0.319 | AAAGGGCAAGATCTCATTTCAATTT | 25 |
| ARHGEF6 | 209539_at | 0.319 | TAACCATGCTTACACACTAAACTAT | 26 |
| PTPRC | 212588_at | 0.319 | ATTGCATATGCATAGTTCCCATGTT | 27 |
| CD247 | 210031_at | 0.314 | GACTGACCTTGATGAGCTGTGCACA | 28 |
| NAMPT | 217738_at | 0.314 | GTCCACTAGAACTCTGCTGTGTGTC | 29 |
| PER2 | 205251_at | 0.313 | TAACATCAGCTGCCTATGCCTATGA | 30 |
| CD99 | 201029_s_at | 0.312 | GTCCCTGTAACTCAAATGTCAACCC | 31 |
| ACAP1 | 205213_at | 0.312 | CCCTGCTACGACTGGCAAAGATGAG | 32 |
| DOCK2 | 213160_at | 0.312 | CTAGGCACAGCTTTCATAACCCAGT | 33 |
| USP7 | 201498_at | 0.311 | AATGCCAGCTGCGTGTCTAGTTTTG | 34 |
| FMNL1 | 204789_at | 0.309 | TCATCACAGATCTGCGGAACCAGCC | 35 |
| PVRIG | 219812_at | 0.309 | GCCCAGGGCCATGGAAGGACCCTTA | 36 |
| TRBC1 | 211796_s_at | 0.308 | CCTCAATGACTCCAGATACTGCCTG | 37 |
| URB2 | 205284_at | 0.307 | GGCAGGTCGGTGACGTTTAGCACAG | 38 |
| CXCR4 | 211919_s_at | 0.306 | GTGGTCTATGTTGGCGTCTGGATCC | 39 |
| CEP350 | 204373_s_at | 0.304 | AAACATCTTGTCTACATCCTTTGGC | 40 |
| SAP30 | 204899_s_at | 0.304 | TGCCGCTGTCTAACTTGGTGTGCAG | 41 |
| NARF | 219862_s_at | 0.304 | ACGGACATGCGGATAAGGCCCTGCT | 42 |
| SLA | 203761_at | 0.303 | TAAGCATTCCGTCCATCTAAGCTCA | 43 |
| IL2RG | 204116_at | 0.303 | GTTACACCCTAAAGCCTGAAACCTG | 44 |
| MFNG | 204153_s_at | 0.3 | GCCTTTCTTGCTGTTAGGGGCTACC | 45 |
| GMFG | 204220_at | 0.3 | AAGACCGGCAGATGGTGGTGCTGGA | 46 |
| WBSCR22 | 207628_s_at | 0.3 | CTTCTCCGGTGGCATGGTGGTAGAC | 47 |
| LCP1 | 208885_at | 0.3 | ACACACCTAGCCAGCTGTCAAGGGC | 48 |
| TRIM14 | 203148_s_at | 0.299 | CAAGGGAGCTTGCACGGTACTGACC | 49 |

TABLE 1-continued mRNA biomarkers of sensitivity to doxorubicin. Affymetrix IDs refer to the array type HG-U133A.

| Gene | Affymetrix ID | Correlation | Affymetrix Probe Sequence | SEQ ID NO: |
|---|---|---|---|---|
| TRBC1 | 210915_x_at | 0.298 | AGATCCTGCTAGGGAAGGCCACCAT | 50 |
| EVL | 217838_s_at | 0.297 | CTGACACGGAACACCAGGTCTGCTC | 51 |
| ZAP70 | 214032_at | 0.293 | TCATGAGTGACTGCTGGATCTACAA | 52 |
| PHF11 | 221816_s_at | 0.291 | TCTTTAGAACTAGTCGTCTCCTCTT | 53 |
| LAPTM5 | 201720_s_at | 0.29 | AGCTGCTCACAACTGGGTCAACGCT | 54 |
| ANP32B | 201306_s_at | 0.286 | GTCTGTGGCTACCAGTTACACTGAG | 55 |
| MCM7 | 208795_s_at | 0.285 | CAAGGGGCAGACAGCTAGGACTCAG | 56 |
| HDAC4 | 204225_at | 0.284 | CTTTTCCGCACAGCTGTGTTGACTT | 57 |
| TRAF3IP3 | 213888_s_at | 0.284 | GAGGCAGCGGGATGGACTACATGAC | 58 |
| PRPF3 | 202251_at | 0.283 | ACAGTGTCCTACAGAGAACATGGCT | 59 |
| WDR59 | 218505_at | 0.282 | ATCCCAGAGGACCCATAAGTGCCGG | 60 |
| SYNRG | 221937_at | 0.282 | GAAGGGAGCATTGTAGCCTGCTGTA | 61 |
| ANP32B | 201305_x_at | 0.281 | GGTTGGACTGCTCATGGATTTTGTA | 62 |
| TRBC1 | 213193_x_at | 0.281 | CAATACACATTCTTCTTTTGCCAGC | 63 |
| BATF | 205965_at | 0.28 | GACCCCACCACTGTGGGTTGCAGGC | 64 |
| BCL11B | 219528_s_at | 0.28 | ACAATGTTGAGTTCAGCATGTGTCT | 65 |
| LAPTM5 | 201721_s_at | 0.278 | GCCATCCATTCAGTCGATTCAGTCA | 66 |
| DDIT4 | 202887_s_at | 0.278 | GGCAGCTATCTTACAGACGCATGAA | 67 |
| TNFAIP8 | 208296_x_at | 0.278 | TAGGAAATGACAGACCCAACCACCA | 68 |
| CXCR4 | 209201_x_at | 0.277 | CACGCACTCACCTCTGTGAGCAGAG | 69 |
| TM6SF1 | 219892_at | 0.275 | TCTCACATTGGTGCATCTCTTCATG | 70 |
| FNBP1 | 213940_s_at | 0.273 | CCGGCAGAGCGGACTGTACGACAGC | 71 |
| CXorf57 | 219355_at | 0.273 | AAAGGCTGCAGTATGTCTATATTCT | 72 |
| PSMD11 | 208776_at | 0.272 | GCTGTCCAATATGTAGCCGCTAGCC | 73 |
| MPHOSPH9 | 215731_s_at | 0.271 | TTCTTGCACTACAGGCACTCAATAA | 74 |
| SEPT6 | 213666_at | 0.27 | GTCTCTTGAGAGAGCCTCTTTGCAT | 75 |
| ANAPC5 | 208722_s_at | 0.269 | GTACCGGTTACAGTACTTGGCCTCT | 76 |
| FYB | 211795_s_at | 0.269 | ATGTCCTTCGGAGTTACCTAGCGGA | 77 |
| POM121 POM121C | 213360_s_at | 0.268 | GTTAAGTTATGCCTGTGCAAAGAAG | 78 |
| LOC728802 PDE4DIP | 213388_at | 0.268 | CTATCTGTGTCCATGAAGTCTTACT | 79 |
| LOC100287515 ZNF26 | 219595_at | 0.267 | TTTAGAACCTGCTTCTCTGATCTGT | 80 |
| CLK2 | 203229_s_at | 0.265 | AAACCGCTGCGGCGGTATCTGACCT | 81 |
| ARHGAP19 | 212738_at | 0.265 | GCCTGAGTGCTTGGGTTACCATGGA | 82 |
| BIN2 | 219191_s_at | 0.265 | CCAAACCTCGCCAGAGAAGCTCTTC | 83 |
| MYB | 204798_at | 0.263 | TGTGGTTGATAGCCAGTCACTGCCT | 84 |
| SUGP2 | 212001_at | 0.263 | CAGCCGTGTCAAAGTCACAGTGTCT | 85 |

TABLE 1-continued mRNA biomarkers of sensitivity to doxorubicin. Affymetrix IDs refer to the array type HG-U133A.

| Gene | Affymetrix ID | Correlation | Affymetrix Probe Sequence | SEQ ID NO: |
|---|---|---|---|---|
| ADD2 | 205268_s_at | 0.262 | ACCGAAACTGGCATCTTACTCTTGG | 86 |
| CYTIP | 209606_at | 0.262 | AAATCTTAGGTTTGCTTATGCCCAG | 87 |
| CD1A | 210325_at | 0.262 | CGCCACATTTTAGCCGTACTTTGCT | 88 |
| PRF1 | 214617_at | 0.262 | GCTCATCGGCTATCGTTAGTGCTAG | 89 |
| CXCR4 | 217028_at | 0.262 | ATTGATGTGTGTCTAGGCAGGACCT | 90 |
| STAT5B | 212549_at | 0.261 | TAAAGGTAGTGGTGTGTCTCGACCC | 91 |
| SEPT6 | 212415_at | 0.258 | AACAGTCATGTGGCTCGCAGATGCA | 92 |
| CD1C | 205987_at | 0.257 | CCGTCGACTCTCCATTTAAATTGTT | 93 |
| CD1B | 206749_at | 0.257 | CATGAGCCATCATCATGTCTCCTCT | 94 |
| CORO1A | 209083_at | 0.257 | TATCTCTCCATGTTCAGTTCCAAGG | 95 |
| KIAA0182 | 212057_at | 0.257 | CACCCACCAGATTGTTACTACAGTG | 96 |
| FBXL14 | 213145_at | 0.256 | GAAGCTCATATCTTATCTCTGTTCT | 97 |
| MOB1A | 214812_s_at | 0.256 | TTCAACAGGCACATTATTTCCCCCT | 98 |
| SMARCE1 | 211988_at | 0.255 | GGTAAATCCATCCTTATTGTATAGA | 99 |
| SRRT | 222047_s_at | 0.255 | GAGAATTTTTTGTACGATCAGCCTT | 100 |
| CD93 | 202878_s_at | 0.254 | GTGCTGTTGCTCTTATCTGCAAGGT | 101 |
| GTF3A | 215091_s_at | 0.254 | CAGTACTTACCCTTGGCTAAGAACT | 102 |
| TAF15 | 202840_at | 0.252 | TGGCAGTGGCTACGGTGGAGACCGA | 103 |

TABLE 2 mRNA biomarkers of resistance to doxorubicin. Affymetrix IDs refer to the array type HG-U133A.

| Gene | Affymetrix ID | Correlation | Affymetrix Probe Sequence | SEQ ID NO: |
|---|---|---|---|---|
| ACTN1 | 208637_x_at | -0.449 | CTTCCTTCAAGATCCTGGCTGGGGA | 104 |
| SFN | 209260_at | -0.427 | CACTCTTCTTGCAGCTGTTGAGCGC | 105 |
| SFN | 33323_r_at | -0.425 | TGACCATGTTTCCTCTCAATAAAGT | 106 |
| CTBP2 | 210835_s_at | -0.414 | AAACTGTTTGCCTGTGGTAGACACC | 107 |
| SFN | 33322_i_at | -0.41 | TGGGTGTGACCATGTTTCCTCTCAA | 108 |
| FHL2 | 202949_s_at | -0.409 | CTCACCCAGGCAATCTTGCCTTCTG | 109 |
| ACTN1 | 208636_at | -0.408 | AAATCCCCTCAGAGGTGTGACTAGT | 110 |
| CST6 | 206595_at | -0.405 | GTGCAGATGTGATAAGTCCCCGAGG | 111 |
| NR2F2 | 209120_at | -0.403 | GTAACGTGATTGATTCAGTATCTTA | 112 |
| REXO2 | 218194_at | -0.399 | TGATGCCAGTTATCATGCTGCCACT | 113 |
| ANXA2 | 201590_x_at | -0.392 | CAAGCCCCTGTATTTTGCTGATCGG | 114 |
| TJP1 | 202011_at | -0.39 | AAGTATCCCTACTGTAATTTGTGAT | 115 |
| NR2F2 | 209121_x_at | -0.386 | TCAAGGCGCTGCACGTTGACTCAGC | 116 |
| ANXA2 | 213503_x_at | -0.386 | CTCACCATGCTTCCAGCTAACAGGT | 117 |
| IGF2BP2 | 218847_at | -0.383 | AGCTACCTCAGGTGTTTTTACCTCA | 118 |

TABLE 2-continued mRNA biomarkers of resistance to doxorubicin. Affymetrix IDs refer to the array type HG-U133A.

| Gene | Affymetrix ID | Correlation | Affymetrix Probe Sequence | SEQ ID NO: |
|---|---|---|---|---|
| CTBP2 | 201220_x_at | -0.381 | AAGTCTACAGGGGCTGGTGACCTCT | 119 |
| CCND1 | 208712_at | -0.377 | AGCAAGCTGCCGAACCAAAAGAATT | 120 |
| COTL1 | 221059_s_at | -0.376 | GCACATTTGATATAGCTCTTTTTCT | 121 |
| AMOTL2 | 203002_at | -0.373 | TTTTTGTGCTGTGAACATTTTCTGC | 122 |
| SDC4 | 202071_at | -0.371 | CTCTCACACTGTTGTCTGTTACTGA | 123 |
| LSR | 208190_s_at | -0.369 | GACGTTTTCTACGTAGCTTTTGTAT | 124 |
| CDKN2A | 209644_x_at | -0.366 | AGAGGCAGTAACCATGCCCGCATAG | 125 |
| ANXA2 | 210427_x_at | -0.363 | ACCAGCTTGCGAATAACAGTCCCCG | 126 |
| GPRC5A | 203108_at | -0.362 | TCCCCAAACTTGCTGTCAATTCCGA | 127 |
| RRAS2 | 212589_at | -0.362 | AGAGCATACCCTTGTATAGCTTCAG | 128 |
| LAPTM4B | 214039_s_at | -0.362 | TCCTTGTATGCGCTTTTTACCTTGA | 129 |
| ANXA2P2 | 208816_x_at | -0.359 | CTGATCAGAATCATGGTCTCCCGCA | 130 |
| RRAS2 | 212590_at | -0.355 | AGAATCCCTTCAGTTTTAGCTACCA | 131 |
| LGALS3 | 208949_s_at | -0.349 | AGTACTGGTTGAACCTGACCACTTC | 132 |
| DBNDD2 SYS1 SYS1-DBNDD2 | 218094_s_at | -0.349 | TGGAGCCTGCAGCTAGCAGTGGGCC | 133 |
| GPRC5A | 212444_at | -0.347 | GGATGCCTTTTCACATCATTTCAGT | 134 |
| KRT18 | 201596_x_at | -0.346 | TCCTGCTGCACCTTGAGTCAGAGCT | 135 |
| LAMC2 | 202267_at | -0.346 | CAGAGCTCTGGGTTGTGCACATTTC | 136 |
| LAPTM4B | 208767_s_at | -0.345 | GTAGAATTCTTCCTGTACGATTGGG | 137 |
| CAPN2 | 208683_at | -0.343 | AATCGTTCTCCTTACAATCAAGTTC | 138 |
| NT5E | 203939_at | -0.342 | AACAGTGTGCAAATGGCAGCTAGAG | 139 |
| LAPTM4B | 208029_s_at | -0.34 | ACATGGGTGACATGCCTCGTATGT | 140 |
| INPP4B | 205376_at | -0.339 | GAATGGTATTCGTTTCACCTGTTGT | 141 |
| TNFRSF12A | 218368_s_at | -0.338 | CAGGGGAACCTTCCAAGGTGTCTGG | 142 |
| SCRN1 | 201462_at | -0.336 | ATATGCCTGTTAGACCTTAGCTGTG | 143 |
| CYR61 | 210764_s_at | -0.336 | GACTAAATGCTACCTGGGTTTCCAG | 144 |
| TNFRSF21 | 218856_at | -0.336 | TTCTGGAACACATTGCTGCACTTTG | 145 |
| ACTN4 | 200601_at | -0.335 | GCCAGCGCTTCTGGTCTGGTAAATA | 146 |
| CDKN2A | 207039_at | -0.335 | GTTACTGGCTTCTCTTGAGTCACAC | 147 |
| DSG2 | 217901_at | -0.335 | ATTGTTGAATGGTGTCATGCAAAGG | 148 |
| EPHA2 | 203499_at | -0.333 | GATAAGTTTCTATTCTGTCAGTGTT | 149 |
| LDLR | 202068_s_at | -0.33 | CACGTAAATGCGTCCCTGTACAGAT | 150 |
| KRT7 | 209016_s_at | -0.328 | GAGTGGGAGCCGTGAATATCTCTGT | 151 |
| PXN | 201087_at | -0.325 | TTTATAGTGACCCACCCTAGATCTT | 152 |
| SLC39A4 | 219215_s_at | -0.324 | AGTCCCAACTCCAGTAAAGACACTC | 153 |
| EPCAM | 201839_s_at | -0.319 | GTGTTATTGCTGTTATTGTGGTTGT | 154 |
| EEF1D | 203113_s_at | -0.318 | AGGCCAAGAAGCCTGCACTGGTGGC | 155 |

TABLE 2-continued mRNA biomarkers of resistance to doxorubicin. Affymetrix IDs refer to the array type HG-U133A.

| Gene | Affymetrix ID | Correlation | Affymetrix Probe Sequence | SEQ ID NO: |
|---|---|---|---|---|
| CYR61 | 201289_at | -0.317 | GCTTTTATTCGTCCTTTGACAAAAG | 156 |
| S100A10 | 200872_at | -0.315 | GAGCAGATCAGGACACTTAGCAAAT | 157 |
| CLIC3 | 219529_at | -0.306 | GCTGCAGATCGAGGACTTTCTGGAG | 158 |
| DYNLT1 | 201999_s_at | -0.305 | ATGAGTATCCCTGTAGGTCACCTGC | 159 |
| TMBIM1 | 217730_at | -0.305 | ACAAGGGTCAGTCTGTCGGGTGGGG | 160 |
| NOSIP | 217950_at | -0.305 | GATGCAGGCCTGAGTGTGTGCGGGA | 161 |
| F2RL1 | 213506_at | -0.304 | AAGCCTTCAGAGGGTTTGGACCACA | 162 |
| CORO1C | 221676_s_at | -0.304 | CCACCGCTCTCATTTCATGGAGTCT | 163 |
| EGR1 | 201694_s_at | -0.303 | CTGAGCTTCGGTTCTCCAGAATGTA | 164 |
| KLF6 | 208961_s_at | -0.302 | AAAGGCTTCCAGGCTGAGAGCCGGC | 165 |
| AGRN | 212285_s_at | -0.302 | AGGTGGCAGGGATGGCTCCGAAGCC | 166 |
| LAMA3 | 203726_s_at | -0.301 | GTAACCCAAGCCTATTTCACAGCAA | 167 |
| ZNF204P | 214823_at | -0.3 | TTAAAAGTCATGGATCTCAATCTCA | 168 |
| PHACTR2 | 204048_s_at | -0.299 | GTATTGGCAATCATGACACCTGTAA | 169 |
| MGAT4B | 220189_s_at | -0.298 | GGTGATTCTGAGCGAGATCTTCCTG | 170 |
| CNN3 | 201445_at | -0.296 | GTACAGCCAGTTCTTTTATGCAAAA | 171 |
| MARCKS | 201669_s_at | -0.296 | ACTTTTCACTTATCTCATGTTAGCT | 172 |
| TRAM1 | 201398_s_at | -0.294 | CAGTGGAACCAAATTTTTGCCATTA | 173 |
| MST1R | 205455_at | -0.294 | CAGCAACCTACATGAACTTGGGCCC | 174 |
| TMSB10 | 217733_s_at | -0.294 | GAAATCGCCAGCTTCGATAAGGCCA | 175 |
| CTNND1 TMX2-CTNND1 | 208407_s_at | -0.293 | TACAGACCATATTACCTGGATTACC | 176 |
| ZYX | 200808_s_at | -0.292 | CTGACCCAGGACCCAACATGGTCTA | 177 |
| FLNB | 208613_s_at | -0.29 | TGCTATAGCGCCATTCCCAAGGCAT | 178 |
| DYRK2 | 202968_s_at | -0.289 | ATTTGCTCAATAACTCTACTCATTT | 179 |
| RHOBTB3 | 202976_s_at | -0.289 | TACACACAGTTTTTCCGACTTTTCA | 180 |
| EXT1 | 201995_at | -0.287 | AGAGCCAGATTGTGCCAACTATCCA | 181 |
| PLXNB2 | 208890_s_at | -0.286 | CCAGGGCAAGTTCCCAGATCCTATG | 182 |
| PELI1 | 218319_at | -0.284 | GACAGTTGCACTACATCAAATCTTT | 183 |
| EGFR | 201983_s_at | -0.282 | CAACCCCGAGTATCTCAACACTGTC | 184 |
| APOBEC3B | 206632_s_at | -0.282 | TTATGCTCAATATTCCCAGAATAGT | 185 |
| AHNAK | 211986_at | -0.282 | CAGACGGAGGTCAGGTCTTCCTCTT | 186 |
| UBC | 211296_x_at | -0.281 | ACATCCAGAAAGAGTCCACCCTGCA | 187 |
| LOC100505584 MT1E | 212859_x_at | -0.281 | GCTTGTTCGTCTCACTGGTGTGAGC | 188 |
| PKM | 201251_at | -0.28 | GGAAGAAGATCAACGCCTCACTGAA | 189 |
| YWHAB | 208743_s_at | -0.279 | TCTTGGTCTGGCACTAAATTTCTCA | 190 |
| SPATS2L | 222154_s_at | -0.278 | GCTTGATCTGTTGATGCTTTCTCTC | 191 |
| LITAF | 200704_at | -0.277 | GGCTGCTGTGTCATCTTTGAAGTCA | 192 |

TABLE 2-continued mRNA biomarkers of resistance to doxorubicin. Affymetrix IDs refer to the array type HG-U133A.

| Gene | Affymetrix ID | Correlation | Affymetrix Probe Sequence | SEQ ID NO: |
|---|---|---|---|---|
| YES1 | 202933_s_at | -0.277 | TTAAGGGCTTTATGTGAACTATGAT | 193 |
| TSPAN1 | 209114_at | -0.276 | AGCTGGCTGCCATGATTGTTTCCAT | 194 |
| CD24 | 209771_x_at | -0.276 | AAGTGGGCTTGATTCTGCAGTAAAT | 195 |
| RND3 | 212724_at | -0.275 | TGAAAACGAGCTTTCTTTCCCATGA | 196 |
| ADAM9 | 202381_at | -0.273 | ATGAGTTATCATCTTAGCTGTGTTA | 197 |
| LAMB1 | 201505_at | -0.272 | GATGCCAGAAGGAAAGCCGAAATGC | 198 |
| LAD1 | 203287_at | -0.271 | GCTGTGGATCTGTTTGGCCAGGGTC | 199 |
| NHP2L1 | 201077_s_at | -0.27 | ACCAAGAAGCTACTGGACCTCGTTC | 200 |
| TPD52L2 | 201379_s_at | -0.269 | GGCCCTGCATGTCAGATGGCGTGGT | 201 |
| KRT8 | 209008_x_at | -0.269 | TCGCCACCTACAGGAAGCTGCTGGA | 202 |
| HTATIP2 | 209448_at | -0.269 | GTCTCTGAGTTACAAAAGTGCTAAT | 203 |
| GJB3 | 215243_s_at | -0.269 | ACTTGGCTCAGTGGAAGCCCTCTTT | 204 |
| TACSTD2 | 202286_s_at | -0.268 | ACATTGCCCGGAAACTCAGTCTATT | 205 |
| TGFA | 205015_s_at | -0.268 | TGTAATCACCTGTGCAGCCTTTTGT | 206 |
| RAB11FIP1 | 219681_s_at | -0.268 | GCTTTTAATTATCTACAGCTATTTT | 207 |
| S100A2 | 204268_at | -0.266 | TTCCACAAGTACTCCTGCCAAGAGG | 208 |
| EIF3G | 208887_at | -0.266 | TGGGCCTGTCTACTGGCGAGAAGGA | 209 |
| MRPL40 | 203152_at | -0.264 | GAAGCTCTGGAGGAACTGCAACTGG | 210 |
| CSE1L | 210766_s_at | -0.264 | GAATGCAGAAGCGCTCCAGTATCTC | 211 |
| EEF1A1 LOC100653236 | 213614_x_at | -0.264 | ATCACCATTGATATCTCCTTGTGGA | 212 |
| FZD6 | 203987_at | -0.263 | GAGTGTCCACTATTGATTGTATTAT | 213 |
| CLMN | 221042_s_at | -0.262 | GACAGTAGCGACTACAGCATTCCTT | 214 |
| HSP90B1 MIR3652 | 200599_s_at | -0.26 | AACAGCAACGCTTCGGTCAGGGTAT | 215 |
| CD63 | 200663_at | -0.259 | CCCGACTCCTGCTGCATTAATGTTA | 216 |
| EZR | 208623_s_at | -0.259 | CACACATGCCACTATGAGCTTTCAG | 217 |
| IER3 | 20163_s_at | -0.257 | AATGCAGGTCTCTTGGTATTTATTG | 218 |
| LDHA | 200650_s_at | -0.256 | AGTGAGTCACATCCTGGGATCCAGT | 219 |
| CSE1L | 201112_s_at | -0.256 | AAAAGAGCATGATCCTGTAGGTCAA | 220 |
| F3 | 204363_at | -0.256 | GCATTTCTAGGACTTTTCTAACATA | 221 |
| PLEKHA1 | 219024_at | -0.256 | GGATTTTACGAGTCTCTTGCCAAGG | 222 |
| ZYX | 215706_x_at | -0.255 | CCATTGTGGACCACCCACACTGAGA | 223 |
| LCN2 | 212531_at | -0.252 | CAGGACTTTTGTTCCAGGTTGCCAG | 224 |
| RRBP1 | 201204_s_at | -0.251 | CCCCTAGACGTTGCCAACCAGAACT | 225 |
| LMNA | 212086_x_at | -0.251 | GCATCATGTAATCTGGGACCTGCCA | 226 |

TABLE 3 mRNA biomarkers of sensitivity to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| HCLS1 | 202957_at | 0.52 | TGATGAGCTTTCCTTTGATCCGGAC | 227 |
| PTPRC | 207238_s_at | 0.458 | GAACAGTTTGTACAGACGTATGCTT | 228 |
| MBNL1 | 201152_s_at | 0.452 | TCCATACCCCTTCAAACATGTTGCT | 229 |
| PTPRCAP | 204960_at | 0.45 | CAACCACAGGCATCAGGCAACCATT | 230 |
| ITGA4 | 213416_at | 0.446 | GAAAGCAGAGTACTATGGTTGTCCA | 231 |
| ARHGAP15 | 218870_at | 0.427 | GCCTTTCAAGCGACAGATGCCTCAT | 232 |
| PTPRC | 212588_at | 0.422 | GTTCTACTCATATATATCTATCTTA | 233 |
| SRSF7 | 213649_at | 0.417 | GGCCAAAGAGGGTCGACCTGCAAAC | 234 |
| ARHGEF6 | 209539_at | 0.415 | GAAGCTTGTGCAGAGTGGTAACCAT | 235 |
| PTPN7 | 204852_s_at | 0.41 | CACAATTTCCAGGGGACCTCAGGTC | 236 |
| IKZF1 | 205038_at | 0.409 | TGTGGAAAGCCTGGATCTCAGCTCC | 237 |
| SELPLG | 209879_at | 0.407 | TTGTCTTTTGGTTGCCATGGTCACC | 238 |
| IFI16 | 208965_s_at | 0.406 | GCGTTTCTGGAGATTACAACATCCT | 239 |
| CUTC | 218970_s_at | 0.404 | ACAGAATTCCACTGTTCTGCTCGGT | 240 |
| CD53 | 203416_at | 0.402 | TCTAAATAATGCCCAGTCTTCTCCC | 241 |
| RHOH | 204951_at | 0.4 | CACAACACTTATGTATGCACCCCAA | 242 |
| PTPRC | 212587_s_at | 0.398 | AAGTGTGCAGAATACTGGCCGTCAA | 243 |
| CD247 | 210031_at | 0.396 | GACTGACCTTGATGAGCTGTGCACA | 244 |
| MTHFD2 | 201761_at | 0.395 | GCTGTCCTTTTGAGGCTTAGTCAGT | 245 |
| SLA | 203761_at | 0.394 | GACTCATGTTTCCCTGTTTCAAAGG | 246 |
| ACAP1 | 205213_at | 0.394 | CTGACCATCGCCATGGAAACAGCCA | 247 |
| CD3D | 213539_at | 0.393 | GACTGGACCTGGGAAAACGCATCCT | 248 |
| NCKAP1L | 209734_at | 0.391 | CTTCCTAAACCCTTGCCATAGTGGA | 249 |
| CTCF | 202521_at | 0.383 | TGGCAGATCATGATTTCCAGCCCAC | 250 |
| ZAP70 | 214032_at | 0.381 | ATCACCAGAATAAACCCAGCTTCCC | 251 |
| MFNG | 204153_s_at | 0.378 | ACCCCTTGCGAACAGGACCAGATTT | 252 |
| IKZF1 | 205039_s_at | 0.374 | AAACAGGGGTTCTTAGTCTCAGCAC | 253 |
| CYFIP2 | 215785_s_at | 0.372 | CAGCCTGCCATAGGATCCAACTGGA | 254 |
| NOTCH1 | 218902_at | 0.371 | TCAGACTTGGCTCAGCTCGGGGAGC | 255 |
| LCP1 | 208885_at | 0.368 | AATCAAGCCACTCGGCAGGCATGGA | 256 |
| NEIL3 | 219502_at | 0.365 | GAACGTTCTATGTATTTCATCGGAT | 257 |
| SRGN | 201858_s_at | 0.364 | AGGACTTGAATCGTATCTTCCCACT | 258 |
| BIN2 | 219191_s_at | 0.363 | ATAAGCTTATCTCAGCTGACTCCTC | 259 |
| SCN3A | 210432_s_at | 0.36 | GAACCCTTGGATTTATGTGAGGTCA | 260 |
| AIF1 | 215051_x_at | 0.36 | CCCCCCAGCCAAGAAAGCTATCTCT | 261 |
| PTGER4 | 204897_at | 0.359 | GTGTTTTTGTGAATTGCTTGGTTGT | 262 |
| PRKACB | 202741_at | 0.357 | TTGTGGCTTATGGGTATTGCTGTCT | 263 |

TABLE 3-continued mRNA biomarkers of sensitivity to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| CXCR4 | 209201_x_at | 0.357 | TGCATTATCATCTCCAAGCTGTCAC | 264 |
| TRAF3IP3 | 213888_s_at | 0.356 | TGAAAAAGGGTTTCTATTCTCTCTG | 265 |
| IL2RG | 204116_at | 0.349 | GACTCTGCCTCGTCAGTGAGATTCC | 266 |
| LAPTM5 | 201720_s_at | 0.347 | GCAGGACAATCTGCTTGTGTCTCCC | 267 |
| GMFG | 204220_at | 0.345 | GAGACAGCCCAGGTTCGTGGTTTAC | 268 |
| SRGN | 201859_at | 0.344 | TTTTCCTGGATATCTGTGTATTTTC | 269 |
| FMNL1 | 204789_at | 0.344 | CCCCCTCCAAATAGCCATACTTAGC | 270 |
| SSBP2 | 203787_at | 0.343 | ACATTGACCCACAGGACATTGTAAA | 271 |
| CORO1A | 209083_at | 0.342 | GACAGTGCCTCGAAAGTCGGACCTG | 272 |
| RFTN1 | 212646_at | 0.342 | GTCTCTGCACCTACTTTTGCAGAAT | 273 |
| ZNF22 | 218005_at | 0.342 | ACTGAGCCAGCCTTTTAGATCTACA | 274 |
| CYTH1 | 202880_s_at | 0.34 | GACAGAGAGGCACCTGGGTCAGTAT | 275 |
| SLA | 203760_s_at | 0.339 | GTCTGGGTTTGCAGATGGGTGCCCT | 276 |
| VAV1 | 206219_s_at | 0.337 | AAAGAGAACCATCAGCAGGCCAGCA | 277 |
| TRBC1 | 210915_x_at | 0.337 | TGACTCCAGATACTGCCTGAGCAGC | 278 |
| MAPRE2 | 213489_at | 0.336 | GAGCTATACATTCTTCTTTCTGGTC | 279 |
| LIMS2 | 220765_s_at | 0.336 | GAGGTGTGGTCAGAGGTGACTTGTT | 280 |
| TRBC1 | 211796_s_at | 0.335 | CTGTCAAGTCCAGTTCTACGGGCTC | 281 |
| PRF1 | 214617_at | 0.332 | AGATTGGATACGCATCAGACAGATG | 282 |
| LAPTM5 | 201721_s_at | 0.331 | CCAATGCTCACCTATTCAGTTGCTC | 283 |
| CXCR4 | 211919_s_at | 0.331 | CCTCTATGCTTTCCTTGGAGCCAAA | 284 |
| PHF11 | 221816_s_at | 0.331 | TCCCAGCACCTAGTATGCTCAGTAA | 285 |
| CD99 | 201028_s_at | 0.329 | TCTAGCTTCATTGCTTACCAGAAAA | 286 |
| CXCR4 | 217028_at | 0.328 | GTATGTCTCGTGGTAGGACTGTAGA | 287 |
| KRT14 | 209351_at | 0.326 | CCCGTGTGGACACAGATCCCACTGG | 288 |
| GLYR1 SEPT6 | 212414_s_at | 0.326 | CATTTGGCATTCACATGTGGCTGTT | 289 |
| TNFAIP8 | 208296_x_at | 0.324 | TTGAGTTCTCCTTTTAAGTACCAAT | 290 |
| LOC72880 2 PDE4DIP | 213388_at | 0.324 | CATTTCCCTACCAAAGCTGTGTATT | 291 |
| LAIR1 | 210644_s_at | 0.323 | CCTTCTACAATCGAGCAGCTCCTTG | 292 |
| EVL | 217838_s_at | 0.323 | GTGCACCAGAGCACGCACAGGAGCC | 293 |
| SATB1 | 203408_s_at | 0.322 | GTGTGTACCCCGTAAGCATGAAACC | 294 |
| PER2 | 205251_at | 0.322 | AATAGATTTGTTTGACTGCTTGTGT | 295 |
| CYTIP | 209606_at | 0.32 | ACAGCCAATTTCTAAGCAGACAGGA | 296 |
| CYFIP2 | 220999_s_at | 0.32 | ACCCCACATTCATATCCCTAAATTT | 297 |
| HNRNPA1 | 222040_at | 0.32 | GAATGACAAGCTGTACCTTAAACCA | 298 |
| CD1B | 206749_at | 0.318 | TGAGGCGCCGGTCATATCAGAATAT | 299 |

TABLE 3-continued mRNA biomarkers of sensitivity to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
| --- | --- | --- | --- | --- |
| SEPT6 | 212415_at | 0.318 | GTAACTGCACTCAAGCTGTGCTCAA | 300 |
| SEPT6 | 213666_at | 0.318 | GTTGACTGTCTACAGCCACTGTTAA | 301 |
| NGLY1 | 220742_s_at | 0.318 | GTAGTCTGTTGGTTCAGTGCATGCT | 302 |
| TRBC1 | 213193_x_at | 0.317 | GGGGGACCTTAGCATGCCTAAGTGA | 303 |
| MAP4K1 | 214219_x_at | 0.317 | GATGGCTCTGTGAAGCTGGTGACCC | 304 |
| PVRIG | 219812_at | 0.317 | TGTGAGTGACAGTTACCCCATTTCA | 305 |
| CD93 | 202878_s_at | 0.315 | GCTTAAGCTTGAATTAGATCCCTGC | 306 |
| ACLY | 210337_s_at | 0.313 | ATGGGGTTCATTGGACACTATCTTG | 307 |
| CD1E | 215784_at | 0.313 | TTTCCTGCTTTGGCTACATATCCAT | 308 |
| TGFB1 | 203085_s_at | 0.312 | AGCTGTCCAACATGATCGTGCGCTC | 309 |
| IFI16 | 208966_x_at | 0.312 | TACAACACTATACATACACACCACC | 310 |
| PPRC1 | 203737_s_at | 0.311 | TGGAAAGATACCTGGCCGCATGACT | 311 |
| MAP4K1 | 206296_x_at | 0.311 | GAGACACGCCCAGTGGATGATCCTA | 312 |
| ACTR2 | 200727_s_at | 0.31 | TCTGCTGCTTTGTTTCTTCTAAGTA | 313 |
| PLCB1 | 213222_at | 0.31 | GTACATATTTTGGTTCTTCTATCTC | 314 |
| ICAM3 | 204949_at | 0.308 | GTACCCCGAGCTGCGGTGTTTGAAG | 315 |
| EIF1 | 212225_at | 0.308 | CCTTTGTGCTTGCAGAAAGTTTGCC | 316 |
| DOCK2 | 213160_at | 0.307 | GATTCCTGAACTCAAGGTACCAGCA | 317 |
| NAP1L1 | 212967_x_at | 0.306 | AAGGGACGTGGGACAGTTCGTACTG | 318 |
| TCF4 | 213891_s_at | 0.305 | GTAGAAGTGTCCAAACAGGTTGTGT | 319 |
| CD3G | 206804_at | 0.304 | GAAATCGTCAGCATTTTCGTCCTTG | 320 |
| PRKCQ | 210038_at | 0.304 | GACACCTTCGCTTGTTATCTTGTCA | 321 |
| SACS | 213262_at | 0.304 | ACAGGATGCAATCTTTTGTTGTCTA | 322 |
| RASGRP2 | 208206_s_at | 0.303 | GTGGTTGGATCAAGGACTCATTCCT | 323 |
| ITM2A | 202747_s_at | 0.3 | CAATAACAGAAAGTCCTTCCGCCTT | 324 |
| ITM2A | 202746_at | 0.299 | ATTGGCATTGCTTGTTTTTGAAAC | 325 |
| JARID2 | 203298_s_at | 0.298 | GCTACCCATATTGCACTGAGCTTGC | 326 |
| SLC16A1 | 202236_s_at | 0.297 | GGCATATGTTTCTGCTAGCTATATA | 327 |
| IMPDH2 | 201892_s_at | 0.295 | TCATATTGCGAAAGCCTTGGCCCTT | 328 |
| HMGN4 | 202579_x_at | 0.293 | AATATATTCTTTACTGCCTTGTGGA | 329 |
| ADD2 | 205268_s_at | 0.293 | ACCGAAACTGGCATCTTACTCTTGG | 330 |
| KIAA0226L | 44790_s_at | 0.293 | CAAATGTTCTGTTTTGGCTGCTATT | 331 |
| BCL11B | 219528_s_at | 0.292 | ACAATGTTGAGTTCAGCATGTGTCT | 332 |
| SH2D1A | 210116_at | 0.291 | ATGGGTGGTTTACCATTTCTTGAGG | 333 |
| NFATC3 | 210555_s_at | 0.29 | CAACCATTGGTCTGCAGGACATCAC | 334 |
| RAC2 | 213603_s_at | 0.29 | GCCAGATGGTTGCTGCCACAACTTG | 335 |
| APOL3 | 221087_s_at | 0.29 | GGTAATGAGCCATGGCCATTGTCCC | 336 |

TABLE 3-continued mRNA biomarkers of sensitivity to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| CD99 | 201029_s_at | 0.289 | GTCCCTGTAACTCAAATGTCAACCC | 337 |
| MYC | 202431_s_at | 0.289 | GCAACCTCACAACCTTGGCTGAGTC | 338 |
| NAP1L1 | 208752_x_at | 0.289 | ATCCTTGCTGCAGACTTCGAAATTG | 339 |
| FHL1 | 210298_x_at | 0.289 | AATCGAAGCTTAGCAGCTCCTCGTG | 340 |
| WIPF1 | 202664_at | 0.288 | CTACCCTAGACATCTGCATCTTTGT | 341 |
| PRKCQ | 210039_s_at | 0.288 | CCCCCATGTGACTTTTATCTGTAGC | 342 |
| MSN | 200600_at | 0.287 | GATGTCATCTGTCACTATAGGTCAT | 343 |
| PTP4A2 | 208617_s_at | 0.287 | GTATCAGTGCCTGCCTGAGTTAGGA | 344 |
| CD1C | 205987_at | 0.284 | CCAGCAACCCAGGAGCCTAGTACAA | 345 |
| — | 213484_at | 0.284 | ACGCAAGAGTACTTACTGTCTTCCC | 346 |
| MAZ | 207824_s_at | 0.283 | AACTGCTCCCACTGTGGCAAGAGCT | 347 |
| FLI1 | 204236_at | 0.282 | ACAGGGCTGTTTAAGTCACTGACTT | 348 |
| MZB1 | 221286_s_at | 0.282 | TAAAACCCAGTGACCTCACTTCTTT | 349 |
| C18orf1 | 209574_s_at | 0.281 | AAGGAATATCCTGGAGTGGTCCCCA | 350 |
| ABCC10 | 213485_s_at | 0.281 | CCCTCTTGCATCTGGAACGCCAGGT | 351 |
| ANP32A | 201051_at | 0.28 | GGACTCTGATGTTACTCTTGAGCTT | 352 |
| CD2 | 205831_at | 0.28 | GTCTCACTACAAGCAGCCTATCTGC | 353 |
| GZMB | 210164_at | 0.28 | ACTCTGGAGGCCCTCTTGTGTGTAA | 354 |
| CDC1 | 200790_at | 0.279 | AGAGTAGGGTCGCCATGATGCAGCC | 355 |
| MYB | 204798_at | 0.278 | GCTGCTATGGTCTTAGCCTGTAGAC | 356 |
| NCOR2 | 207760_s_at | 0.278 | TCTGTCATTTACACACGTCGTTCTA | 357 |
| CDH11 | 207173_x_at | 0.277 | TTTCGCCTTAAACTCTGGACACTCT | 358 |
| TCF4 | 222146_s_at | 0.277 | CAATGCCCGAGAGCGTCTGCGGGTC | 359 |
| GPSM3 | 204265_s_at | 0.276 | AACCTGAGAGACAGCTCTACCCTTC | 360 |
| FNBP1 | 212288_at | 0.276 | AGCGCAGCGCAAAGGTCTCAATGCC | 361 |
| TNFAIP3 | 202644_s_at | 0.274 | GTGGTTGCTGTCATATTTGCTCTAG | 362 |
| ITK | 211339_s_at | 0.273 | GATGATTTACTCAGCTTATCCAAA | 363 |
| ADA | 204639_at | 0.271 | TTTTACATTTATTCCTTCCAAGAAG | 364 |
| SH2D1A | 211210_x_at | 0.27 | GAAGTCCTCAGCTAGAAGTACACAA | 365 |
| SASH3 | 204923_at | 0.269 | ATTCAGGACAAGCTGCAACTTCCCC | 366 |
| IGLL1 | 206660_at | 0.268 | AGGTCATGCACGAAGGGAGCACCGT | 367 |
| STAT5B | 212549_at | 0.268 | TTGGGGCCTCAAATTTGACTCTGCC | 368 |
| SLC7A6 | 203580_s_at | 0.267 | AATGTGATTTTCCTAGGCTACTGCA | 369 |
| THY1 | 208850_s_at | 0.265 | TTGTACTTTTGTTCCAGAGCTGCT | 370 |
| LCP2 | 205269_at | 0.263 | AAATCACTAAACCTCGTTTTCTCAG | 371 |
| CD1A | 210325_at | 0.263 | ATATCCCTTACTCCAGAGGGCCTTC | 372 |
| GNA15 | 205349_at | 0.262 | GCGGACGAGAGAAATCGCGGCCCAC | 373 |

TABLE 3-continued mRNA biomarkers of sensitivity to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| BCAT1 | 214452_at | 0.262 | TATGCTACTGGGACAGACTGTTGCA | 374 |
| SFPQ | 201586_s_at | 0.261 | AAAGACCAACAAATCTCAAGCCCTA | 375 |
| TNFAIP8 | 210260_s_at | 0.261 | GAGTTCTCCTTTTAAGTACCAATGA | 376 |
| IER5 | 218611_at | 0.26 | AACGTTTATATCCTGTGATTACTCT | 377 |
| CYB5R4 | 219079_at | 0.26 | GTTCTCGTCTGCATTTGTGGACCAG | 378 |
| SRPK2 | 203182_s_at | 0.259 | GCATGATCATGCTTGTCTAGAACAC | 379 |
| GPR65 | 214467_at | 0.259 | TAGAGCATGCTGTGAACTTCGAAGA | 380 |
| FKBP11 | 219117_s_at | 0.258 | GGTAGGGATGGCCATGGTGCCAGCC | 381 |
| ARHGEF7 | 202548_s_at | 0.256 | TTCTGTGGATCCAGTATCTTCCTCG | 382 |
| CD1D | 205789_at | 0.255 | GTATCTGAAGACCTACCAGGGACAA | 383 |
| FHL1 | 214505_s_at | 0.255 | GCCAACAAGCGCTTTGTTTTCCACC | 384 |
| GIMAP6 | 219777_at | 0.255 | AATCATATTGGTATTCTAGTTGGCA | 385 |
| SH2D1A | 211211_x_at | 0.254 | GAAGTCCTCAGCTAGAAGTACACAA | 386 |
| FYB | 211795_s_at | 0.254 | GTTATACAAACCACAGATGACACAA | 387 |

TABLE 4 mRNA biomarkers of resistance to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| SDC4 | 202071_at | -0.504 | CAGTAACCACATGCGGCTGTTTAAA | 388 |
| CTBP2 | 210835_s_at | -0.452 | AAACTGTTTGCCTGTGGTAGACACC | 389 |
| TMBIM1 | 217730_at | -0.452 | GGGAGATACCGAAGCCTACTGTGGT | 390 |
| COTL1 | 221059_s_at | -0.445 | GGGCTCCCAAAGCGACAAGATCGTT | 391 |
| CTBP2 | 201220_x_at | -0.438 | GTTTGCCTGTGGTAGACACCTGCAC | 392 |
| LAMA3 | 203726_s_at | -0.428 | GACGACACTGAGGATCCCTGTGTGG | 393 |
| LGALS3 | 208949_s_at | -0.424 | AGTACTGGTTGAACCTGACCACTTC | 394 |
| LDLR | 202068_s_at | -0.423 | GAAATCGCCGTGTTACTGTTGCACT | 395 |
| TACSTD2 | 202286_s_at | -0.42 | ACTGGGCCTATGTAGTAGCCTCATT | 396 |
| LAPTM4B | 214039_s_at | -0.419 | TATACTTCTGCCTAACAACATGGAA | 397 |
| ABLIM1 | 200965_s_at | -0.417 | GCATACGTTTCTTTACAGCAGAGGA | 398 |
| AGRN | 212285_s_at | -0.415 | GTGTTGATTTTATTTGACCCCTGGA | 399 |
| RBM47 | 218035_s_at | -0.409 | CAATGTTCCTGATGATGTACCCCAC | 400 |
| EPCAM | 201839_s_at | -0.408 | GTGTGCATTAAATATGCTTCCACAG | 401 |
| LAD1 | 203287_at | -0.407 | CTTTTTGTGTGCAACCACTTACCCT | 402 |
| F2RL1 | 213506_at | -0.407 | GGTTTGGACCACATCTCTTTGGAAA | 403 |
| CST6 | 206595_at | -0.405 | GGCATCAAGTACTTCCTGACGATGG | 404 |
| TJP1 | 202011_at | -0.403 | AAGGATGCTTGTACATAATGCGTGC | 405 |

TABLE 4-continued mRNA biomarkers of resistance to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
| --- | --- | --- | --- | --- |
| MGAT4B | 220189_s_at | -0.402 | TCAACACGTCTGTGGAGGTGCTGCC | 406 |
| LSR | 208190_s_at | -0.4 | AGAACTTGGCCCTGAGTCGGGAAAG | 407 |
| S100A10 | 200872_at | -0.399 | CCACAGCTTCCCCCATAGAAGGATT | 408 |
| HOXB7 | 204779_s_at | -0.394 | TCTGGACTAACCCTGTGGTTGCCTG | 409 |
| RRAS2 | 212589_at | -0.394 | GAAACCTTCCCAATAGAGTACAACA | 410 |
| CLMN | 221042_s_at | -0.392 | AACCAGGAAGGCCAACAGCTCAGGA | 411 |
| NPC2 | 200701_at | -0.39 | CCTCATTGAGTTCGGTGCATCTGGC | 412 |
| HOXB7 | 216973_s_at | -0.385 | GTAAGGTCTTTGTAAAATCTTGCAG | 413 |
| CAPN2 | 208683_at | -0.374 | AATCAAGTTCTTGACCCTATTCGGC | 414 |
| PDXK | 218019_s_at | -0.374 | GGTCCTGTTGACTTGTATGATATCC | 415 |
| ANXA2 | 213503_x_at | -0.372 | CTGATCAGAATCATGGTCTCCCGCA | 416 |
| YWHAB | 217717_s_at | -0.371 | CCCCCTTTCCTACAGCAATATGTTC | 417 |
| ANXA2 | 201590_x_at | -0.367 | CGTGGCCATCCCTGTGAGGGTGACG | 418 |
| LMNA | 212086_x_at | -0.366 | CTGCCCTGCACGTCATGGGAGGGGG | 419 |
| ANXA2 | 210427_x_at | -0.365 | ACCAGCTTGCGAATAACAGTCCCCG | 420 |
| S100A11 | 200660_at | -0.363 | CGGGAAGGGCGTGGGTTGAGGAGAG | 421 |
| EGR1 | 201694_s_at | -0.362 | GCAGTTCATTATTTTGTGGTTCTAT | 422 |
| NR2F2 | 209120_at | -0.358 | GTAACGTGATTGATTCAGTATCTTA | 423 |
| DSG2 | 217901_at | -0.356 | GGATTTATATAGTGTGCTCCCACTA | 424 |
| LAPTM4B | 208029_s_at | -0.355 | AAGACCATTAGAAAGCACCAGGCCG | 425 |
| SPATS2L | 222154_s_at | -0.354 | GGGTTTCACAGTGCAATCTCTGCCC | 426 |
| CD63 | 200663_at | -0.345 | GAATTGCTTTTGTCGAGGTTTTGGG | 427 |
| LEPROT | 202378_s_at | -0.345 | GTTTGGCTGTTCATGTAGTCACGGT | 428 |
| ALDH7A1 | 208951_at | -0.345 | GCACACACAGAGACTTTTGCTCCGA | 429 |
| GJB3 | 215243_s_at | -0.343 | AGGTGAGAAGTGCTCCCAAGCAGAC | 430 |
| SCRN1 | 201462_at | -0.342 | AGCACAAGCTTATGCTTCCCGTAGC | 431 |
| DYNLT1 | 201999_s_at | -0.342 | GGCACCGAAGTCAGATGAGTATCCC | 432 |
| RHOBTB3 | 202976_s_at | -0.341 | TACACACAGTTTTTCCGACTTTTCA | 433 |
| IGF2BP2 | 218847_at | -0.34 | AATGGTACTTGTCCTAGCGTTTTGG | 434 |
| KRT19 | 201650_at | -0.339 | TGGTTCACCAGCCGGACTGAAGAAT | 435 |
| GPR56 | 212070_at | -0.339 | ACACTCTCCTAAGAGGTTCTCTCCA | 436 |
| LAPTM4B | 208767_s_at | -0.338 | AACTTCCCCCAAATCTGATGGACCT | 437 |
| ANXA2P2 | 208816_x_at | -0.338 | CTGATCAGCTGTACGACTCCATGAA | 438 |
| ZNF165 | 206683_at | -0.337 | AGCTCAAAACTTGCTAGGCATCAGA | 439 |
| ACTN4 | 200601_at | -0.335 | GCCAGCGCTTCTGGTCTGGTAAATA | 440 |
| TGFA | 205016_at | -0.334 | GATTTACCAGGCTTTCTGAAAGATC | 441 |
| LAMC2 | 202267_at | -0.333 | ATCCATCCTTCCAACATATATTTAT | 442 |
| APOBEC3B | 206632_s_at | -0.333 | ATTCCCAGAATAGTTTTCAATGTAT | 443 |

TABLE 4-continued mRNA biomarkers of resistance to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
| --- | --- | --- | --- | --- |
| RAB11FIP1 | 219681_s_at | -0.332 | TTGTTGTTACTCACTTAAGACTGGA | 444 |
| GPRC5A | 203108_at | -0.331 | AAATTCCTGGGGCTGATACTTCTCT | 445 |
| NR2F2 | 209121_x_at | -0.331 | ACCCCAACCAGCCGACGAGATTCGG | 446 |
| — | 208540_x_at | -0.33 | GACTGAGCGGTGCATTGAGTCCCTG | 447 |
| COND1 | 208712_at | -0.33 | AGCAAGCTGCCGAACCAAAAGAATT | 448 |
| BCL2L1 | 212312_at | -0.329 | GGGGTAGGGCTGACTAGAAGGGCCA | 449 |
| GPRC5A | 212444_at | -0.329 | GGTGGTGGGGCAACACTGCTTAATG | 450 |
| HTATIP2 | 209448_at | -0.327 | GCCATGAAAACCTTATGACCGTGCA | 451 |
| RRAS2 | 212590_at | -0.327 | TATACACAGACATGCTCTTTTTTA | 452 |
| TNFRSF12A | 218368_s_at | -0.324 | CAGGGGAACCTTCCAAGGTGTCTGG | 453 |
| OSBPL10 | 219073_s_at | -0.324 | CCACAGCCTCAATCTTGTATTTAGT | 454 |
| LCN2 | 212531_at | -0.322 | GACGGCTGAGTGCACAGGTGCCGCC | 455 |
| AMOTL2 | 203002_at | -0.314 | ATGGCTGTTTTGTTATGCCACCCTG | 456 |
| AHNAK | 211986_at | -0.314 | TGGGGTGATGGGTTGCAGACGGAGG | 457 |
| PLEKHA1 | 219024_at | -0.313 | AGCCTTCCGGTCAGTGACGTGTGAG | 458 |
| SLC25A13 | 203775_at | -0.311 | AGTATTTAATTCATGTTGCCTTGCA | 459 |
| PPDPF | 218010_x_at | -0.309 | CCCACCCTGTAAACTAGGCGGCTGC | 460 |
| S100A14 | 218677_at | -0.309 | GAGGCTCAGGGGACTGGTTGGGCCA | 461 |
| PELI1 | 218319_at | -0.308 | TTCACTCAGGAAATGCATGTCAGGA | 462 |
| PLXNB2 | 208890_s_at | -0.307 | CCAGGGCAAGTTCCCAGATCCTATG | 463 |
| PPIC | 204517_at | -0.305 | TTCTGAATTCATTATGATCCCCATA | 464 |
| TNFRSF21 | 218856_at | -0.305 | GGCGCCCTTTCCATAGAGAATTTGC | 465 |
| TSPAN1 | 209114_at | -0.304 | TGCTGTGGCTTCACCAACTATACGG | 466 |
| ANXA3 | 209369_at | -0.303 | AATTGTGTGAGGAACACGCCGGCCT | 467 |
| TCF7L2 | 212761_at | -0.301 | CTGTAGCATGCCGTTCTGGATTAAT | 468 |
| CDC14B | 221556_at | -0.301 | ATCCGATGATAGTACTGCAGTTTTC | 469 |
| CSE1L | 210766_s_at | -0.3 | GGTTCCATCAATGGTGAGCACCAGC | 470 |
| CNN3 | 201445_at | -0.298 | GAGCTCAGTATTTAGTCCTTTGTTT | 471 |
| EGFR | 201983_s_at | -0.298 | AAATTAGCCTGGACAACCCTGACTA | 472 |
| YES1 | 202933_s_at | -0.298 | GAATGGAGCAGTTCCTTATATAATA | 473 |
| ACTN1 | 208636_at | -0.298 | GGACAACTTTGATATTGCTTGGCAC | 474 |
| SFN | 209260_at | -0.296 | TCTTGCTCCAAAGGGCTCCGTGGAG | 475 |
| DBNDD2 SYS1 SYS1-DBNDD2 | 218094_s_at | -0.295 | TAAACCATCCCGTAGTCTTCTAATA | 476 |
| MLEC | 20061_7_at | -0.294 | GCCAGCAGCCACAACATGCATTGAC | 477 |
| LITAF | 200704_at | -0.294 | GGATTCTAGGTTGGCTGCTGTGTCA | 478 |
| LAMB1 | 201505_at | -0.294 | GATGCCAGAAGGAAAGCCGAAATGC | 479 |

TABLE 4-continued mRNA biomarkers of resistance to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| SFN | 33323_r_at | -0.294 | TGTGACCATGTTTCCTCTCAATAAA | 480 |
| PKM | 201251_at | -0.293 | CGTGGCACTGGTAGGTTGGGACACC | 481 |
| INPP4B | 205376_at | -0.292 | GATGAGCACCAGTTACACAAGGACT | 482 |
| RNASEH2A | 203022_at | -0.29 | CTCAATGAAGGGTCCCAAGCCCGTC | 483 |
| ZCCHC14 | 212655_at | -0.29 | TCACATGTGTGAGTCTTACGTGCAC | 484 |
| CSE1L | 201112_s_at | -0.288 | AAAAGAGCATGATCCTGTAGGTCAA | 485 |
| CDKN2A | 207039_at | -0.288 | CTTTTCACTGTGTTGGAGTTTTCTG | 486 |
| YES1 | 202932_at | -0.287 | TTTCCTCTTATCAACAACTTGTGAC | 487 |
| C20orf111 | 209020_at | -0.287 | ACCAGGGGCAAGCCATGCACATGCA | 488 |
| CD24 | 209771_x_at | -0.287 | GCCTCGACACACATAAACCTTTTTA | 489 |
| SERPINB6 | 211474_s_at | -0.286 | TGGCCTTATCCGTGCAGTGGTGGCA | 490 |
| SFN | 33322_i_at | -0.286 | ATGTCTGCTGGGTGTGACCATGTTT | 491 |
| KRT8 | 209008_x_at | -0.282 | TCGCCACCTACAGGAAGCTGCTGGA | 492 |
| KRT18 | 201596_x_at | -0.281 | TCCTGCTGCACCTTGAGTCAGAGCT | 493 |
| PLS1 | 205190_at | -0.281 | TAAGATATGTTCTTGCTCTTTTATA | 494 |
| SLC25A1 | 210010_s_at | -0.281 | TGCAGTAGTGCCAAAAGGCCCCTTC | 495 |
| MST1R | 205455_at | -0.279 | TGCTTAGCTGCCTTGAGCTAACCCC | 496 |
| ATP1B1 | 201242_s_at | -0.278 | AACCTACTAGTCTTGAACAAACTGT | 497 |
| EPHA2 | 203499_at | -0.278 | GGGCAGACTGTGAACTTGACTGGGT | 498 |
| FKBP9 | 212169_at | -0.278 | AGACAGCAATGACAGTCCACCTGCC | 499 |
| CD24 | 216379_x_at | -0.278 | TAAATCTTTTACAACTGCCTCGACA | 500 |
| TGIF1 | 203313_s_at | -0.274 | GTGGATGTTGCACTCAAACGGGCTG | 501 |
| DBI | 209389_x_at | -0.274 | GTTACTGTGCCATGTGTTTATCCTA | 502 |
| RND3 | 212724_at | -0.274 | TTTCCCATGATAGTGCTTCGTTTTT | 503 |
| ADD3 | 205882_x_at | -0.273 | TAAGCCACCTTCTACTATGCAATTT | 504 |
| TSPAN4 | 209263_x_at | -0.273 | CAAGGCAGACACCTACTGCGCGTAG | 505 |
| CASK | 211208_s_at | -0.273 | GCATGTGGACAGTCGCGAGCGTTTA | 506 |
| CTSA | 200661_at | -0.27 | GCCGGCTTCGTGAAGGAGTTCTCCC | 507 |
| CTNNAL1 | 202468_s_at | -0.27 | AAACAAGCTAATTCCTCTATGCCAC | 508 |
| S100A2 | 204268_at | -0.27 | TTCCACAAGTACTCCTGCCAAGAGG | 509 |
| LASP1 | 200618_at | -0.269 | GTTGTTGTCTCATTTTGGTCTGTTT | 510 |
| LGALS3BP | 200923_at | -0.269 | TTCCACTAGGGTCCACCAGGAGTTC | 511 |
| MALL | 209373_at | -0.268 | GAGGCCTGGCGGAATGGTGGTGCCC | 512 |
| ANXA4 | 201302_at | -0.267 | AAGCTTCAAACTAGGTATTCTGGGA | 513 |
| HMGA2 | 208025_s_at | -0.266 | GTTCCTTTGAGTGTCTTCTAACTTT | 514 |
| PRKCI | 209678_s_at | -0.266 | TGTGTCTGATCCTCATTTTTCAACC | 515 |
| CALM1 CALM2 CALM3 | 211984_at | -0.266 | AATTTGGTCAAGTCTACTCTTCCGT | 516 |

TABLE 4-continued mRNA biomarkers of resistance to epirubicin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| FA2H | 219429_at | -0.266 | ACCAAGGAGCTGGTCAGACGGCCCT | 517 |
| ITGA6 | 201656_at | -0.265 | GATACTAAGGACGTTGTTTTGGTTG | 518 |
| SVIL | 202565_s_at | -0.265 | GTATCTTCATACACGTTTGGAAATG | 519 |
| TUBB4B | 213726_x_at | -0.265 | CAGGAGCTGTTCAAGCGCATCTCCG | 520 |
| SLC39A4 | 219215_s_at | -0.265 | CCCACCTTTGACTTAAGATCCCACA | 521 |
| LACTB2 | 218701_at | -0.264 | AGATTTCTATGCACCTTTACTCTTT | 522 |
| MECOM | 221884_at | -0.264 | AGTCCAAATCGCAGGCATATGCTAT | 523 |
| NT5E | 203939_at | -0.263 | AGCCTGCTCAGCTCTGCATAAGTAA | 524 |
| MBP | 210136_at | -0.262 | AGCTTCATGTTGCTCTGCGACAATC | 525 |
| MRPL40 | 203152_at | -0.26 | GGAGCTCACCTTTGAGGAGACTGAG | 526 |
| ADD3 | 201752_s_at | -0.257 | TAACCCATTTAGTCATCTCACAGAA | 527 |
| RHOC | 200885_at | -0.254 | AGAACAAGCGTCGGAGGGCTGTCC | 528 |

The biomarker HSLS1 (SEQ ID NO: 1) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker HSLS1 (SEQ ID NO: 1) may be assessed using nucleic acid amplification methods (e.g., PCR, such as qRT-PCR) or a device (e.g., a microarray). As is described above, the level of HSLS1 (SEQ ID NO: 1) in the patient sample may then be compared, e.g., to the level of HSLS1 (SEQ ID NO: 1) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker HSLS1 (SEQ ID NO: 1) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker PTPRCAP (SEQ ID NO: 2) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker PTPRCAP (SEQ ID NO: 2) may be assessed using nucleic acid amplification methods (e.g., PCR, such as qRT-PCR) or a device (e.g., a microarray). As is described above, the level of PTPRCAP (SEQ ID NO: 2) in the patient sample may then be compared, e.g., to the level of PTPRCAP (SEQ ID NO: 2) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker PTPRCAP (SEQ ID NO: 2) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker NEIL3 (SEQ ID NO: 3) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker NEIL3 (SEQ ID NO: 3) may be assessed using nucleic acid amplification methods (e.g., PCR, such as qRT-PCR) or a device (e.g., a microarray). As is described above, the level of NEIL3 (SEQ ID NO: 3) in the patient sample may then be compared, e.g., to the level of NEIL3 (SEQ ID NO: 3) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker NEIL3 (SEQ ID NO: 3) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker PTPRC (SEQ ID NO: 4, 20, or 27) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker PTPRC (SEQ ID NO: 4, 20, or 27) may be assessed using nucleic acid amplification methods (e.g., PCR, such as qRT-PCR) or a device (e.g., a microarray). As is described above, the level of PTPRC (SEQ ID NO: 4, 20, or 27) in the patient sample may then be compared, e.g., to the level of PTPRC (SEQ ID NO: 4, 20, or 27) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker PTPRC (SEQ ID NO: 4, 20, or 27) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker IFI16 (SEQ ID NO: 5) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker IFI16 (SEQ ID NO: 5) may be assessed using nucleic acid amplification methods (e.g., PCR, such as qRT-PCR) or a device (e.g., a microarray). As is described above, the level of IFI16 (SEQ ID NO: 5) in the patient sample may then be compared, e.g., to the level of IFI16 (SEQ ID NO: 5) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker IFI16 (SEQ ID NO: 5) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker RHOH (SEQ ID NO: 6) may be used to assess a cancer patient's (e.g, a patient with cancer that is resistant to one or more cancer, such as one or more cancer therapies other than anthracycline) responsiveness to anthracycline. The level of the biomarker RHOH (SEQ ID NO: 6) may be assessed using nucleic acid amplification methods (e.g., PCR, such as qRT-PCR) or a device (e.g., a microarray). As is described above, the level of RHOH (SEQ ID NO: 6) in the patient sample may then be compared, e.g., to the level of RHOH (SEQ ID NO: 6) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker RHOH (SEQ ID NO: 6) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker SSBP2 (SEQ ID NO: 7) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker SSBP2 (SEQ ID NO: 7) may be assessed using nucleic acid amplification methods (e.g., PCR, such as qRT-PCR) or a device (e.g., a microarray). As is described above, the level of SSBP2 (SEQ ID NO: 7) in the patient sample may then be compared, e.g., to the level of SSBP2 (SEQ ID NO: 7) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker SSBP2 (SEQ ID NO: 7) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker CD2 (SEQ ID NO 8) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker CD2 (SEQ ID NO 8) may be assessed using nucleic acid amplification methods (e.g., PCR, such as qRT-PCR) or a device (e.g., a microarray). As is described above, the level of CD2 (SEQ ID NO 8) in the patient sample may then be compared, e.g., to the level of CD2 (SEQ ID NO 8) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker CD2 (SEQ ID NO 8) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker ITGA4 (SEQ ID NO: 9) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker ITGA4 (SEQ ID NO: 9) may be assessed using nucleic acid amplification methods (e.g., PCR, such as qRT-PCR) or a device (e.g., a microarray). As is described above, the level of ITGA4 (SEQ ID NO: 9) in the patient sample may then be compared, e.g., to the level of ITGA4 (SEQ ID NO: 9) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker ITGA4 (SEQ ID NO: 9) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker ARHGAP15 (SEQ ID NO: 10) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker ARHGAP15 (SEQ ID NO: 10) may be assessed using nucleic acid amplification methods (e.g., PCR, such as qRT-PCR) or a device (e.g., a microarray). As is described above, the level of ARHGAP15 (SEQ ID NO: 10) in the patient sample may then be compared, e.g., to the level of ARHGAP15 (SEQ ID NO: 10) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker ARHGAP15 (SEQ ID NO: 10) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker SRPK2 (SEQ ID NO: 11) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker SRPK2 (SEQ ID NO: 11) may be assessed using nucleic acid amplification methods (e.g., PCR, such as qRT-PCR) or a device (e.g., a microarray). As is described above, the level of SRPK2 (SEQ ID NO: 11) in the patient sample may then be compared, e.g., to the level of SRPK2 (SEQ ID NO: 11) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker SRPK2 (SEQ ID NO: 11) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker CD99 (SEQ ID NO: 12 and 31) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). responsiveness to anthracycline. The level of the biomarker CD99 (SEQ ID NO: 12 and 31) may be assessed using nucleic acid amplification methods (e.g., PCR, such as qRT-PCR) or a device (e.g., a microarray). As is described above, the level of CD99 (SEQ ID NO: 12 and 31) in the patient sample may then be compared, e.g., to the level of CD99 (SEQ ID NO: 12 and 31) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker CD99 (SEQ ID NO: 12 or 31) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker SRSF7 (SEQ ID NO: 13) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker SRSF7 (SEQ ID NO: 13) may be assessed using nucleic acid amplification methods (e.g., PCR, such as qRT-PCR) or a device (e.g., a microarray). As is described above, the level of SRSF7 (SEQ ID NO: 13) in the patient sample may then be compared, e.g., to the level of SRSF7 (SEQ ID NO: 13) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker SRSF7 (SEQ ID NO: 13) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2

(SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124), The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker CTCF (SEQ ID NO: 14) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker CTCF (SEQ ID NO: 14) may be assessed using nucleic acid amplification methods (e.g., PCR, such as qRT-PCR) or a device (e.g., a microarray). As is described above, the level of CTCF (SEQ ID NO: 14) in the patient sample may then be compared, e.g., to the level of CTCF (SEQ ID NO: 14) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker CTCF (SEQ ID NO: 14) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker SELPLG (SEQ ID NO: 15) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker SELPLG (SEQ ID NO: 15) may be assessed using nucleic acid amplification methods (e.g., PCR, such as qRT-PCR) or a device (e.g., a microarray). As is described above, the level of SELPLG (SEQ ID NO: 15) in the patient sample may then be compared, e.g., to the level of SELPLG (SEQ ID NO: 15) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker SELPLG (SEQ ID NO: 15) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker SFN (SEQ ID NO: 105, 106, 108, 475, 480, or 491) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker SFN (SEQ ID NO: 105, 106, 108, 475, 480, or 491) may be assessed using nucleic acid amplification methods (e.g., PCR, such as qRT-PCR) or a device (e.g., a microarray). As is described above, the level of SFN (SEQ ID NO: 105, 106, 108, 475, 480, or 491) in the patient sample may then be compared, e.g., to the level of SFN (SEQ ID NO: 105, 106, 108, 475, 480, or 491) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker SFN (SEQ ID NO: 105, 106, 108, 475, 480, or 491) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker ACTN1 (SEQ ID NO: 104 or 110) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker ACTN1 (SEQ ID NO: 104 or 110) may be assessed using nucleic acid amplification methods (e.g., PCR, such as qRT-PCR) or a device (e.g., a microarray). As is described above, the level of ACTN1 (SEQ ID NO: 104 or 110) in the patient sample may then be compared, e.g., to the level of ACTN1 (SEQ ID NO: 104 or 110) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker ACTN1 (SEQ ID NO: 104 or 110) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker CTBP2 (SEQ ID NO: 107 or 119) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker CTBP2 (SEQ ID NO: 107 or 119) may be assessed using nucleic acid amplification methods (e.g., PCR, such as qRT-PCR) or a device (e.g., a microarray). As is described above, the level of CTBP2 (SEQ ID NO: 107 or 119) in the patient sample may then be compared, e.g., to the level of CTBP2 (SEQ ID NO: 107 or 119) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker CTBP2 (SEQ ID NO: 107 or 119) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker FHL2 (SEQ ID NO: 109) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker FHL2 (SEQ ID NO: 109) may be assessed using nucleic acid amplification methods (e.g., PCR, such as qRT-PCR) or a device (e.g., a microarray). As is described above, the level of FHL2 (SEQ ID NO: 109) in the patient sample may then be compared, e.g., to the level of FHL2 (SEQ ID NO: 109) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker FHL2 (SEQ ID NO: 109) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker CST6 (SEQ ID NO: 111) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker CST6 (SEQ ID NO: 111) may be assessed using nucleic acid amplification methods (e.g., PCR, such as qRT-PCR) or a device (e.g., a microarray). As is described above, the level of CST6 (SEQ ID NO: 111) in the patient sample may then be compared, e.g., to the level of CST6 (SEQ ID NO: 111) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker CST6 (SEQ ID NO: 111) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker NR2F2 (SEQ ID NO: 112 or 116) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker NR2F2 (SEQ ID NO: 112 or 116) may be assessed using nucleic acid amplification methods (e.g., PCR, such as qRT-PCR) or a device (e.g., a microarray). As is described above, the level of NR2F2 (SEQ ID NO: 112 or 116) in the patient sample may then be compared, e.g., to the level of NR2F2 (SEQ ID NO: 112 or 116) in a cell (e.g., a cancer cell) or tissue (e.g., a tumor tissue) known to be sensitive or resistant to treatment with the anthracycline and, which can be used as a reference to determine the cancer patient's responsiveness to the anthracycline.

The biomarker NR2F2 (SEQ ID NO: 112 or 116) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO:

15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker REXO2 (SEQ ID NO: 113) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker REXO2 (SEQ ID NO: 113) may be assessed using nucleic acid amplification methods (e.g., PCR, such as qRT-PCR) or a device (e.g., a microarray). As is described above, the level of REXO2 (SEQ ID NO: 113) in the patient sample may then be compared, e.g., to the level of REXO2 (SEQ ID NO: 113) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker REXO2 (SEQ ID NO: 113) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker ANXA2 (SEQ ID NO: 114, 117, or 126) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker ANXA2 (SEQ ID NO: 114, 117, or 126) may be assessed using nucleic acid amplification methods (e.g., PCR, such as qRT-PCR) or a device (e.g., a microarray). As is described above, the level of ANXA2 (SEQ ID NO: 114, 117, or 126) in the patient sample may then be compared, e.g., to the level of ANXA2 (SEQ ID NO: 114, 117, or 126) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker ANXA2 (SEQ ID NO: 114, 117, or 126) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker TJP1 (SEQ ID NO: 115) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker KRT8 (SEQ ID NO: 106 (SEQ ID NO: 314 or 386) may be assessed using nucleic acid amplification methods (e.g., PCR, such as qRT-PCR) or a device (e.g., a microarray). As is described above, the level of TJP1 (SEQ ID NO: 115) in the patient sample may then be compared, e.g., to the level of TJP1 (SEQ ID NO: 115)

in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker TJP1 (SEQ ID NO: 115) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline The biomarker IGF2BP2 (SEQ ID NO: 118) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker IGF2BP2 (SEQ ID NO: 118) may be assessed using nucleic acid amplification methods (e.g., PCR, such as qRT-PCR) or a device (e.g., a microarray). As is described above, the level of IGF2BP2 (SEQ ID NO: 118) in the patient sample may then be compared, e.g., to the level of IGF2BP2 (SEQ ID NO: 118) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker IGF2BP2 (SEQ ID NO: 118) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), CCND1 (SEQ ID NO: 120), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker CCND1 (SEQ ID NO: 120) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker CCND1 (SEQ ID NO: 120) may be assessed using nucleic acid amplification methods (e.g., PCR, such as qRT-PCR) or a device (e.g., a microarray). As is described above, the level of CCND1 (SEQ ID NO: 120) in the patient sample may then be compared, e.g., to the level of CCND1 (SEQ ID NO: 120) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker CCND1 (SEQ ID NO: 120) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), COTL1 (SEQ ID NO: 121), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker COTL1 (SEQ ID NO: 121) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker COTL1 (SEQ ID NO: 121) may be assessed using nucleic acid amplification methods (e.g., PCR, such as qRT-PCR) or a device (e.g., a microarray). As is described above, the level of COTL1 (SEQ ID NO: 121) in the patient sample may then be compared, e.g., to the level of COTL1 (SEQ ID NO: 121) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker COTL1 (SEQ ID NO: 121) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), AMOTL2 (SEQ ID NO: 122), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker AMOTL2 (SEQ ID NO: 122) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker AMOTL2 (SEQ ID NO: 122) may be assessed using nucleic acid amplification methods (e.g., PCR, such as qRT-PCR) or a device (e.g., a microarray). As is described above, the level of AMOTL2 (SEQ ID NO: 122) in the patient sample may then be compared, e.g., to the level of AMOTL2 (SEQ ID NO: 122) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker AMOTL2 (SEQ ID NO: 122) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), SDC4 (SEQ ID NO: 123), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker SDC4 (SEQ ID NO: 123) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker SDC4 (SEQ ID NO: 123) may be assessed using nucleic acid amplification methods (e.g., PCR, such as qRT-PCR) or a device (e.g., a microarray). As is described above, the level of SDC4 (SEQ ID NO: 123) in the patient sample may then be compared, e.g., to the level of SDC4 (SEQ ID NO: 123) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker SDC4 (SEQ ID NO: 123) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO:

111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), and LSR (SEQ ID NO: 124). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

The biomarker and LSR (SEQ ID NO: 124) may be used to assess a cancer patient's (e.g., a patient with a known cancer type that is resistant to one or more cancer therapies and/or has an unknown responsiveness to an anthracycline) responsiveness to an anthracycline (e.g., doxorubicin, epirubicin, daunorubicin, or idarubicin, or an anthracycline-containing liposome, such as a doxorubicin-containing liposome (e.g., 2B3-101)). The level of the biomarker and LSR (SEQ ID NO: 124) may be assessed using nucleic acid amplification methods (e.g., PCR, such as qRT-PCR) or a device (e.g., a microarray). As is described above, the level of and LSR (SEQ ID NO: 124) in the patient sample may then be compared, e.g., to the level of and LSR (SEQ ID NO: 124) in a cell (e.g., a cancer cell) or tissue (e.g., a tumor tissue) known to be sensitive or resistant to treatment with the anthracycline, which can be used as a reference to determine the cancer patient's responsiveness to the anthracycline.

The biomarker and LSR (SEQ ID NO: 124) may be used as the sole biomarker to predict cancer patient responsiveness to treatment with the anthracycline or in combination with one or more additional biomarkers (e.g., one, two, three, four, five, ten, or all of the biomarkers shown in Tables 1-4), such as HSLS1 (SEQ ID NO: 1), PTPRCAP (SEQ ID NO: 2), NEIL3 (SEQ ID NO: 3), PTPRC (SEQ ID NO: 4, 20, or 27), IFI16 (SEQ ID NO: 5), RHOH (SEQ ID NO: 6), SSBP2 (SEQ ID NO: 7), CD2 (SEQ ID NO 8), ITGA4 (SEQ ID NO: 9), ARHGAP15 (SEQ ID NO: 10), SRPK2 (SEQ ID NO: 11), CD99 (SEQ ID NO: 12 or 31), SRSF7 (SEQ ID NO: 13), CTCF (SEQ ID NO: 14), SELPLG (SEQ ID NO: 15), SFN (SEQ ID NO: 105, 106, 108, 475, 480, or 491), ACTN1 (SEQ ID NO: 104 or 110), CTBP2 (SEQ ID NO: 107 or 119), FHL2 (SEQ ID NO: 109), CST6 (SEQ ID NO: 111), NR2F2 (SEQ ID NO: 112 or 116), REXO2 (SEQ ID NO: 113), ANXA2 (SEQ ID NO: 114, 117, or 126), TJP1 (SEQ ID NO: 115), IGF2BP2 (SEQ ID NO: 118), CCND1 (SEQ ID NO: 120), COTL1 (SEQ ID NO: 121), AMOTL2 (SEQ ID NO: 122), SDC4 (SEQ ID NO: 123). The level of the biomarker(s) may be determined using, e.g., a microarray, PCR, or other techniques described herein, for example, using a nucleic acid probe sequence based on the target sequences shown in Tables 1-4. In particular, the patient is determined to be responsive to the anthracycline if the level of the biomarker or the complement thereof is substantially similar to the level of the biomarker or the complement thereof in a cell or tissue known to be sensitive to the anthracycline and/or the level of the biomarker or the complement thereof is substantially dissimilar to the level of the biomarker or the complement thereof in a cell or tissue known to be resistant to the anthracycline.

Methods of Treatment

The diagnostic methods of the invention permit the assessment of whether a patient is likely to be responsive to treatment with an anthracycline (e.g., doxorubicin, epirubicin, daunorubicin, or idarubicin, or an anthracycline-containing liposome, such as a doxorubicin-containing liposome (e.g., 2B3-101)), and can thus be used to direct the patient's treatment (e.g., as a first line therapy and/or as a second or third line therapy). A patient to be treated or tested for responsiveness to an anthracycline according to the methods may include, e.g., a patient that has been diagnosed with cancer, a patient that has not received a cancer treatment (e.g., the anthracycline, an anti-cancer agent other than the anthracycline, or radiation), a patient that has received a cancer treatment (e.g., an anti-cancer agent other than the anthracycline or radiation), or a patient during treatment with the anthracycline. For example, the patient may have a solid tumor or a hematological cancer, such as a cancer type selected from brain cancer (e.g., astrocytoma, glioblastoma multiforme, and craniopharyngioma), breast cancer (e.g., medullary carcinoma, ER-positive breast cancer, and/or a metastatic form of breast cancer), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system.

In particular, the cancer of the patient is, e.g., breast cancer (e.g., ERpos breast cancer and/or a metastatic form of breast cancer), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN).

The patient may have a cancer (e.g., a patient with a solid tumor or hematological cancer) that is resistant to one or more cancer therapies other than an anthracycline (e.g., irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, APO010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab), surgery, or radiation. The patient may also have experienced a recurrence following a treatment with a cancer therapy other than the anthracycline, surgery, or radiation.

A patient found to be responsive to an anthracycline according to the methods of the invention may be preferentially selected for treatment with the anthracycline. For example, a patient can be identified as responsive to anthracycline by determining the level of one or more biomarkers (e.g., one or more of the biomarkers shown in Tables 1-4, such as HSLS1 (SEQ ID NO: 1)) in a biological sample (e.g., a tumor sample) obtained from the patient, and subsequently administered the anthracycline. Alternatively, a patient can be identified as less likely to be responsive to anthracycline by determining the level of one or more biomarkers (e.g., one or more of the biomarkers shown in Tables 1-4, such as HSLS1 (SEQ ID NO: 1)) in a biological sample obtained from the patient.

If the patient exhibits levels of one or more biomarkers indicative of non-responsiveness to an anthracycline, the patient may be treated with or offered a treatment with an agent other than the anthracycline. In particular, the patient may be treated with, e.g., radiation and/or administration of a therapeutic agent, such as irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, adriamycin, decitabine, estramustine, azaguanine, mitomycin, paclitaxel, taxotere, APO010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

Administration of an Anthracycline

Once a patient has been determined to be responsive to an anthracycline (e.g., doxorubicin, epirubicin, daunorubicin, or idarubicin, or an anthracycline-containing liposome, such as a doxorubicin-containing liposome (e.g., 2B3-101)), according to the methods described herein, the anthracycline may be administered to the patient, for example, parenterally or enterally. Enteral routes of the anthracycline administration include oral, buccal, sublabial, sublingual, or by inhalation. Parenteral routes of the anthracycline administration include intravenous, transdermal, intradermal, intramuscular, intra-arterial, intracranial, subcutaneous, intraorbital, intraventricular, intraspinal, intraperitoneal, or intranasal. The preferred route for administration of anthracycline may be intravenous, such as intravenous infusion or as a bolus injection. For example, anthracycline is administered by intravenous infusion over a time period of, e.g., daily, weekly, or monthly, such as once, twice, three, four, five, or six times weekly.

An anthracycline (e.g., doxorubicin, epirubicin, daunorubicin, or idarubicin) can be administered at, e.g., a dose of about 1 mg/kg to about 100 mg/kg of anthracycline, such as about 5 mg/kg, about 6 mg/kg, about 7 mg/kg, about 8 mg/kg, about 9 mg/kg, or about 10 mg/kg (e.g., about 5 mg/kg or about 7 mg/kg). In particular, anthracycline may be administered at a treatment regimen of, e.g., about 1 mg/kg to about 10 mg/kg weekly, such as about 5 mg/kg or about 7 mg/kg weekly. The treatment regimen may be repeated one to five times, one to ten times, one to fifteen times, one to twenty times, or more. The administration of anthracycline can be repeated at such a frequency for a certain period of time, followed by a period without treatment. Such repeated administrations can occur over a course of therapy lasting a specified length of time (e.g., at least 1 week, 2 weeks, 3 weeks, 1 month, 2 months, 3 months, 6 months, 8 months, 10 months, 12 months, 18 months, 24 months, 36 months, 48 months, or 60 months).

An anthracycline-containing liposome, such as a doxorubicin-containing liposome (e.g., 2B3-101)), can be administered at a dose of about 20 mg/m$^2$ to about 80 mg/m$^2$ of doxorubicin, such as a dose of about 40 mg/m$^2$, about 50 mg/m$^2$ or about 60 mg/m$^2$. The method may include administering the anthracycline-containing liposome to the patient in a treatment regimen at least once per one, two, or three weeks, such as in a dose of about 40 mg/m$^2$, about 50 mg/m$^2$ or about 60 mg/m$^2$ every three or four weeks (e.g., about 50 mg/m$^2$ every three or four weeks).

An anthracycline (e.g., doxorubicin, epirubicin, daunorubicin, or idarubicin, or an anthracycline-containing liposome, such as a doxorubicin-containing liposome (e.g., 2B3-101)) can be administered in a pharmaceutical composition that includes one or more pharmaceutically acceptable carriers, excipients, or diluents. Examples of suitable carriers, excipients, or diluents of the anthracycline include, but are not limited to, sodium chloride solution, saline, sterile water, polyalkylene glycols, oils of vegetable origin, hydrogenated napthalenes, suitable buffer, 1,3-butanediol, and/or Ringer's solution. Other exemplary carriers, excipients, or diluents are described in the Handbook of Pharmaceutical Excipients, 6th Edition, Rowe et al., Eds., Pharmaceutical Press (2009), hereby incorporated by reference in its entirety.

Liposomes

An anthracycline-containing liposome (e.g., liposome containing doxorubicin, epirubicin, daunorubicin, or idarubicin, such as a doxorubicin-containing liposome (e.g., 2B3-101)) for use in the methods may include neutral phospholipids, cholesterol (Chol), and polymer-conjugated lipids. For example, an anthracycline-containing liposome (e.g., a doxorubicin-containing liposome) may include about 40% to about 75% (mol/mol) of a neutral phospholipid, about 20% to about 45% (mol/mol) of Chol, and about 3% to about 6% (mol/mol) of a polymer-conjugated lipid. In particular, the anthracycline-containing liposome includes hydrogenated soy phosphatidylcholine (HSPC) in an amount of about 55% (mol/mol), Chol in an amount of about 40% (mol/mol), and [poly(ethylene glycol)]-distearoyl phosphatidyl ethanolamine (DSPE-PEG) conjugated to glutiothionate (DSPE-PEG-GSH) in an amount of about 5% (mol/mol). For instance, a doxorubicin-containing liposome is 2B3-101 (DOXIL®/CAELYX®) and includes HSPC in an amount of about 55% (mol/mol), Chol in an amount of about 40% (mol/mol), and DSPE-PEG-GSH in an amount of about 5% (mol/mol).

The anthracycline-containing liposome may include one or more neutral phospholipids, such as phosphatidyl choline (PC) or phosphatidylethanolamine (PE), in an amount of about 40% to about 75% (mol/mol) of the liposomal composition. Preferably, the neutral phospholipid is PC, such as PC in an amount of about 40% to about 60% (mol/mol). For example, the neutral phospholipid may include, e.g., HSPC, 1,2-dipalmitoyl-sn-glycero-3-phosphocholine (DPPC), dimyristoylphosphatidylcholine (DMPC), soy phosphatidylcholine (SPC), distearoyl phosphatidylcholine (DSPC), or egg yolk phosphatidylcholine (EYPC). In particular, the neutral lipid is HSPC in an amount of about 55% (mol/mol). The liposome may also include, e.g., about 20% to about 45% (mol/mol) Chol, such as about 20% to about 40% (mol/mol) Chol, about 20% to about 30% (mol/mol) Chol, about 25% to about 40% (mol/mol) Chol, about 25% to about 35% (mol/mol) Chol, or about 25% to about 30% (mol/mol) Chol. In particular, the anthracycline-containing liposome includes Chol is in an amount of about 40% (mol/mol).

Additionally, the anthracycline-containing liposome may include one or more polymer-conjugated lipid, such as PEG [poly(ethylene glycol)], PAcM [poly(N-acryloylmorpholine)], PVP [poly(vinylpyrrolidone)], PLA [poly(lactide)], PG [poly(glycolide)], POZO [poly(2-methyl-2-oxazoline)], PVA [poly(vinyl alcohol)], HPMC (hydroxypropylmethylcellulose), PEO [poly(ethylene oxide)], chitosan [poly(D-glucosamine)], PAA [poly(aminoacid)], polyHEMA [Poly (2-hydroxyethylmethacrylate)], and co-polymers thereof, such as a polymer-conjugated lipid further conjugated to GSH. Preferably, the liposome includes a polymer-conjugated lipid in an amount of at least 2%, such as an amount of polymer-conjugated lipid of at least 5% and no more than 15% (mol/mol) or at least 3% and no more than 6% (mol/mol). For example, the anthracycline-containing liposome includes DSPE-PEG conjugated to GSH in an amount of about 5% (mol/mol). The composition of the 2B3-101 liposome in milligrams (mg) can be as follows: about 2 mg/mL doxorubicin, about 10 mg/mL HSPC, about 3 mg/mL of DSPE-PEG2000-mal-GSH, and about 3 mg/mL of cholesterol.

Kits

Kits of the invention can be used for determining the responsiveness of a cancer patient (e.g., a patient with a solid tumor or hematological cancer that is resistant to one or more cancer therapies other than the anthracycline) to an anthracycline (e.g., doxorubicin, epirubicin, daunorubicin, or idarubicin, or an anthracycline-containing liposome, such as a doxorubicin-containing liposome (e.g., 2B3-101)). Kits of the invention can include reagents and/or materials for, e.g., collecting and/or purifying nucleic acids from biological samples (such as those obtained from a patient to be treated with a target drug(s) of the invention), reagents for amplifying such nucleic acids to produce an amplified sample, and/or at least one device of the invention. Reagents for amplifying nucleic acids may include, e.g., PCR reagents, including but not limited to DNA polymerase, RNA polymerase, PCR buffer, magnesium chloride solutions, nucleic acid primers (e.g., primers designed to target particular biomarkers of responsiveness to a target drug(s) of interest), and/or any other PCR reagents as are well known in the art. In particular, kits useful in the method may include one or more of the following: a kit for RNA extraction from tumors (e.g., Trizol for mRNA, mirVana miRNA isolation kit from Ambion Inc), a kit for RNA labeling (e.g., MessageAmp from Ambion Inc., FlashTag from Genisphere Inc), a microarray for measuring biomarker levels (e.g., HG-U133A, HG-U133_Plus2 or miRNA-1.0 from Affymetrix Inc), a microarray hybridization station and scanner (e.g., GeneChip System 3000Dx from Affymetrix Inc), and/or software for analyzing the levels of biomarkers as described in herein (e.g., implemented in R from R-Project or S-Plus from Insightful Corp.).

For example, a kit of the invention can include one or more probes capable of detecting one or more biomarkers of Tables 1-4 (e.g., the kit may include probes for one or more of the biomarkers of Tables 1-4). Such probes can, for example, include nucleic acids capable of specifically hybridizing to the biomarker(s) based on nucleic acid sequence complementarity. In particular, a probe has at least 85% sequence identity (e.g., 85%, 90%, 95%, 97%, 98%, 99%, or 100% sequence identity) to a nucleic acid sequence that is complementary or identical to at least 5 (e.g., at least 15 or more) consecutive nucleotides of one or more biomarkers. The probes can be attached to a solid surface, such as a microarray. The kit may include NanoString capture probes, NanoString reporter probes, and/or one or more nCounter cartridges. The kit may include reagents for next generation sequencing, including but not limited to poly(T) oligonucleotides, dye terminators, sequencing adapters, adapter ligation reagents, reverse transcriptase, primers (e.g., random primers), DNA-cleaving enzymes, polymerases, and/or any combination thereof. The kit may also be one that includes a protein array and/or reagents for detection of the polypeptide product(s) of one or more biomarkers of Tables 1-4 (e.g., antibodies or antigen-binding fragments that specifically bind to the one or more biomarkers).

The following examples are intended to illustrate, rather than limit, the invention.

EXAMPLES

Example 1. Identification of Biomarkers of Sensitivity and Resistance to Doxorubicin Using Affymetrix HG-U133A Arrays DNA chip measurements of the 60 cancer cell lines of the NCI60 data set were performed using Affymetrix HG-U133A arrays and logit normalized. For each array, the logit transformation was performed followed by a Z-transformation to mean zero and SD 1, and correlated to growth inhibition (log(GI50)). Growth inhibition data of different therapeutic agents against the same cell lines were downloaded from the National Cancer Institute. The similarity in growth inhibition profile profiles for different therapeutic agents, including doxorubicin, daunorubicin and epirubicin, and idarubicine, were determined using the NCI60 growth assay (FIG. 1). In a multidimensional scaling plot, doxorubicin, daunorubicin, and epirubicin were determined to have similar effects on the NCI60 tumor cell lines, whereas idarubicine has a slightly different effect on the NCI60 tumor cell lines.

Next, the expression of each gene in each cell line was correlated to the growth of those cell lines (log(GI50)) in the presence of doxorubicin. The Pearson correlation coefficient was then determined to identify genes positively and negatively correlated to sensitivity to doxorubicin. Tables 1 and 2 show the top positively correlated genes (the biomarkers of sensitivity) and negatively correlated genes (the biomarkers of resistance) for doxorubicin using the Affymetrix HG-U133A arrays. These biomarkers of sensitivity and resistance shown in Tables 1 and 3, respectively, may be used individually or in any combination of two or more to identify patients that are responsive to the anthracycline doxorubicin.

Example 2. Identification of Biomarkers of Sensitivity and Resistance to Epirubicin Using Affymetrix HG-U133A Arrays DNA chip measurements of the 60 cancer cell lines of the NCI60 data set were also performed using HG-U133_Plus_2 arrays and logit normalized. For each array, the logit transformation was performed followed by a Z-transformation to mean zero and SD 1, and correlated to growth inhibition (log(GI50)). Growth inhibition data of epirubicin against the same cell lines were downloaded from the National Cancer Institute. Each gene's expression in each cell line was correlated to the growth of those cell lines (log(GI50)) in the presence of epirubicin. The covariance (Pearson correlation coefficient multiplied by standard deviation) was then determined to identify genes positively and negatively correlated to sensitivity to epirubicin. Tables 3 and 4 show the top positively correlated genes (the biomarkers of sensitivity) and negatively correlated genes (the biomarkers of resistance) using the Affymetrix HG-U133A arrays, respectively. These biomarkers of sensitivity and resistance shown in Tables 3 and 4, respectively, may be used individually or in any combination of two or more to identify patients that are responsive to the anthracycline epirubicin.

Figure 2:
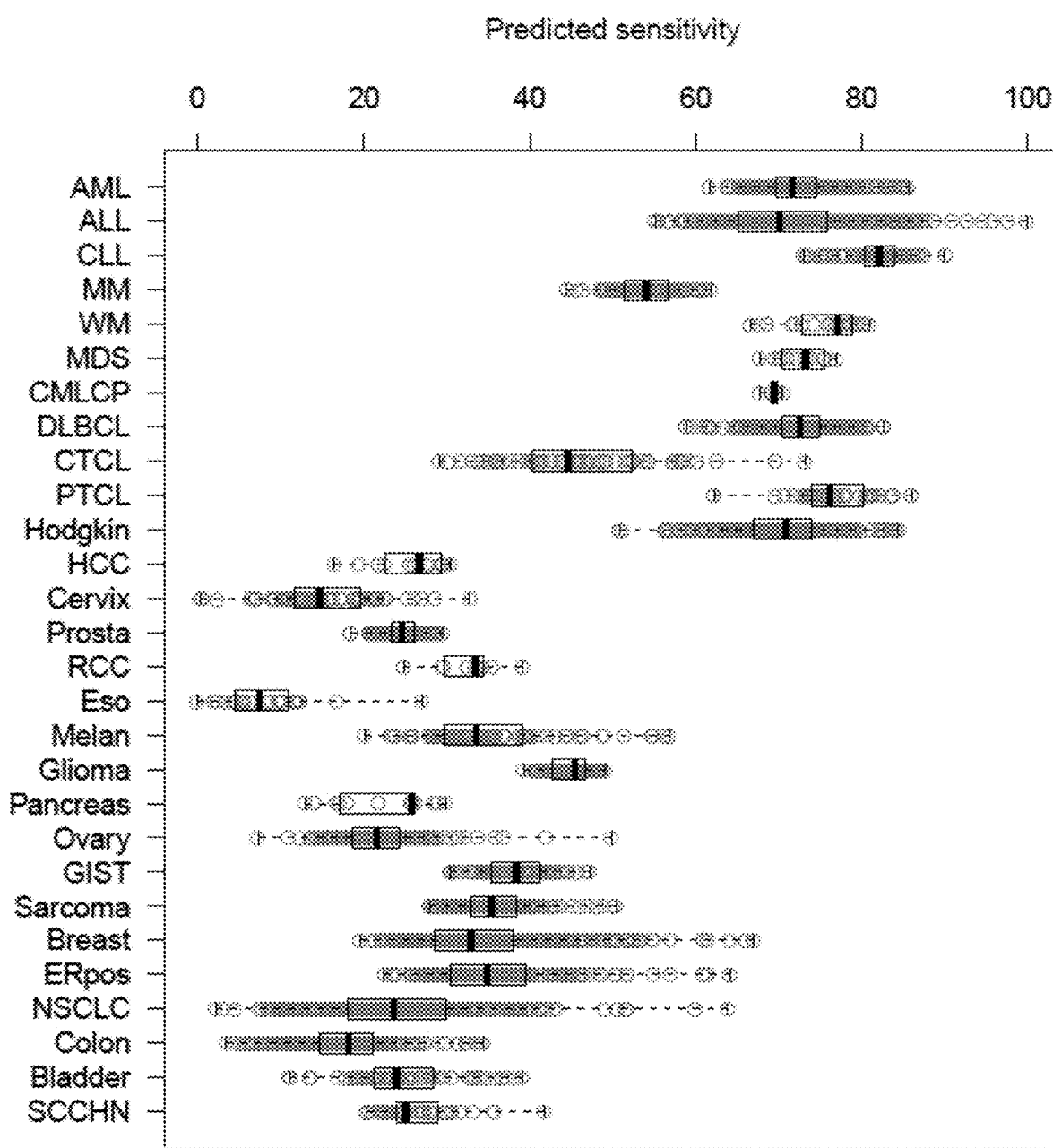
FIG. 2 is a graph grouping predicted sensitivity to the anthracycline, doxorubicin (e.g., a doxorubicin-containing liposome), by cancer type. Each gray circle represents the predicted doxorubicin sensitivity of one patient calculated as the difference between the mean of the levels of the biomarkers of sensitivity (e.g., Tables 1 and/or 3) and the mean of the levels of the biomarkers of resistance for the patient (e.g., Tables 2 and/or 4). Patients are grouped according to cancer type. The median predicted sensitivity (black bar) for a cancer type is related to the relative response rate for that cancer type. The predictions are used for relative comparisons to compare cancer types and cannot be used for absolute predictions of response rate for a given cancer type. The predictions are normalized to a scale of 0 to 100 for all 3,522 patients.

Example 3. Predicting Responsiveness to Doxorubicin in Cancer Patient Populations An mRNA-based predictor of responsiveness to doxorubicin (e.g., a doxorubicin-containing liposome 2B3-101 (DOXIL®/CAELYX®)) developed according to the methods of the invention was applied to 3,522 patients having a variety of cancers. Each patient had a pre-treatment measurement of gene expression with an Affymetrix array. The predicted doxorubicin sensitivity of each patient was calculated as the difference between the mean of the levels of the biomarkers of sensitivity (Table 1) and the mean of the levels of the biomarkers of resistance (Table 2) for the patient. When the patients were grouped by cancer types, and cancer types predicted to be more responsive to the doxorubicin were identified (FIG. 2). Of 27 different cancer types, patients with hematological cancer types were predicted to be more responsive to treatment with doxorubicin than patients with solid tumor cancers.

The median of the boxplots shown in FIG. 2 is a cutoff that may be used to separate patients predicted to be responsive to treatment with doxorubicin, such as the doxorubicin-containing liposome 2B3-101 (DOXIL®/CAELYX®), from patients predicted to be non-responsive to the treatment with doxorubicin for a given cancer type. Values above the median indicate patients predicted to be responsive to doxorubicin, while values below the median indicate patients predicted to be non-responsive to doxorubicin. For a test sample from an individual patient, it is useful to compare the test sample to the reference population for the same cancer type. If the test sample is above the median for the reference population of the same cancer type, then the patient is predicted to be responsive to doxorubicin treatment. If the test sample is below the median for the reference population of the same cancer type, then the patient is predicted to be non-responsive to the doxorubicin treatment. This method for predicting patient responsiveness can also be used when the reference cancer population consists of only two patients: a patient responsive to the doxorubicin treatment and a patient non-responsive to the doxorubicin treatment.

Example 4. Clinical Validation of Identified Biomarkers of Resistance and Sensitivity The biomarkers of sensitivity and resistance identified in Example 2 and shown in Tables 3 and 4 have been validated in a clinical trial of 137 breast cancer patients treated with epirubicin. Patients were examined every 9 to 12 weeks by CT scan and clinical evaluation. After patient informed consent, mRNA was isolated from formalin fixed paraffin embedded tumor tissue from diagnostic biopsies and analyzed using Affymetrix arrays. Blinded predictions of epirubicin efficacy were compared to clinical data collected retrospectively from patient medical records. Statistical analysis was performed using Cox proportional hazards model adjusted for treatment line. The primary endpoint was progression free survival (PFS). Median time to progression was 9.3 months (95% CI: 7.2-13.2). Of the 137 patients, four received epirubicin more than once.

Scoring the Drug Response Predictor (DRP) of the biomarkers of sensitivity and resistance as a continuous covariate demonstrated that the DRP was significantly associated to PFS (p=0.02). The estimated hazard ratio was 0.56 (90% CI: 0.35-0.89) comparing two patients with DRP score differing by 50 percentage points. The estimated median time to progression for a patient with a DRP value of 25% was 7 months versus 13 months for a patient with a DRP value of 75%. No interaction with previous adjuvant chemotherapy was observed (p=0.98). Since the anti-tumor activity of epirubicin was determined to be nearly identical to that of doxorubicin, these results indicate that the identified biomarkers of sensitivity and resistance to epirubicin can be used to predict patient responsiveness to doxorubicin, such as a doxorubicin-containing liposome (e.g., 2B3-101 (DOXIL®/CAELYX®)).

Other Embodiments

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. For example, it is anticipated that measuring the level of proteins, metabolites, identifying genetic mutations and DNA copy number variations, all will be useful in determining patient responsiveness.

The invention claimed is:

1. A method of treating cancer in a human patient in need thereof, comprising administering an anthracycline to the patient, wherein the patient has been determined to be responsive to the anthracycline by a method comprising:
  (a) contacting a tumor sample from the patient comprising a plurality of nucleic acid molecules with a device comprising:
    i) single-stranded nucleic acid molecules capable of specifically hybridizing with nucleotides of biomarkers of sensitivity, wherein the biomarkers of sensitivity are HCLS1 and PTPRCAP or a complement of HCLS1 and PTPRCAP; and
    ii) one or more single-stranded nucleic acid molecules capable of specifically hybridizing with nucleotides of biomarkers of resistance, wherein the biomarkers of resistance are ACTN1 and SFN or a complement of ACTN1 and SFN;
  (b) detecting a level of expression of the biomarkers of sensitivity and the biomarkers of resistance; and
  (c) calculating a difference score for the patient by subtracting a mean of the level of expression of the biomarkers of resistance from a mean of the level of expression of the biomarkers of sensitivity, wherein the difference score is above a cutoff value.

2. The method of claim 1, further comprising administering one or more additional therapies to the patient prior to, concurrently with, or after administration of the anthracycline, wherein the one or more additional therapies are selected from the group consisting of surgery, radiation, or a therapeutic agent, and wherein optionally the therapeutic agent is selected from the group consisting of cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, AP0010, ara-c, methylprednisolone, methotrexate, methylgag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

3. The method of claim 1, wherein the anthracycline is administered to the patient intravenously, intramuscularly, transdermally, intradermally, intra-arterially, intracranially, subcutaneously, intraorbitally, intraventricularly, intraspinally, intraperitoneally, or intranasally.

4. The method of claim 3, wherein the anthracycline is administered by intravenous infusion.

5. The method of claim 1, wherein the anthracycline is administered to the patient at a dose of about 1 mg/kg to about 100 mg/kg of anthracycline.

6. The method of claim 5, wherein the anthracycline is administered to the patient at a dose of about 5 mg/kg, about 6 mg/kg, about 7 mg/kg, about 8 mg/kg, about 9 mg/kg, or about 10 mg/kg.

7. The method of claim 1, comprising administering the anthracycline to the patient in a treatment regimen daily, weekly, or monthly.

8. The method of claim 7, wherein the treatment regimen comprises administration of the anthracycline at least once, twice, three, four, five, or six times weekly.

9. The method of claim 7, wherein the treatment regimen is repeated two to twenty times.

10. The method of claim 1, wherein the contacting step (a) and the detecting step (b) occur prior to, concurrent with, or after administration of the anthracycline to the patient, and/or wherein the contacting step (a) and the detecting step (b) occur two or more times.

11. The method of claim 1, wherein the anthracycline is selected from the group consisting of doxorubicin, epirubicin, daunorubicin, idarubicin, aclarubicin, nemorubicin, pixantrone, and valrubicin or a derivative thereof.

12. The method of claim 1, wherein the anthracycline is in a liposomal formulation.

13. The method of claim 12, wherein said liposomal formulation comprises a liposome containing doxorubicin or a derivative thereof.

14. The method of claim 1, wherein the patient is resistant to one or more cancer therapies other than anthracycline.

15. The method of claim 1, wherein the cancer is selected from a solid tumor cancer and a hematological cancer.

16. The method of claim 1, wherein the cancer is selected from the group consisting of brain cancer, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN).

17. The method of claim 16, wherein the breast cancer is an estrogen receptor-positive (ERpos) breast cancer and/or a metastatic form of breast cancer.

18. The method of claim 1, wherein the patient exhibits cancer relapse after treatment with one or more cancer therapies other than the anthracycline.

19. The method of claim 1, wherein the patient exhibits cancer relapse after a first cancer treatment and prior to treatment with the anthracycline.

20. The method of claim 1, wherein the patient has not been administered a treatment for cancer.

21. The method of claim 1, wherein the patient has an unknown responsiveness to the anthracycline prior to steps a)-c).

22. The method of claim 1, wherein the device comprises at least three, at least four, at least five, at least six, at least seven, at least eight, at least nine, at least ten, or more single-stranded nucleic acid molecules of i) and/or ii).

23. The method of claim 1, wherein the single-stranded nucleic acid molecules of the device are 10 to 100 nucleotides in length.

24. The method of claim 1, wherein the single-stranded nucleic acid molecules are labeled or immobilized on a solid substrate.

25. The method of claim 1, wherein the device is a microarray or is for performing a quantitative reverse transcriptase polymerase chain reaction (qRT-PCR) reaction.

26. The method of claim 1, wherein the level of the biomarkers of sensitivity and/or the biomarkers of resistance are detected by performing microarray analysis or qRT-PCR.

27. The method of claim 1, wherein the nucleic acid molecules of the sample comprise mRNA or a cDNA thereof.

28. The method of claim 1, wherein the cutoff value is above a $50^{th}$ percentile of a reference population having the same diagnosis as the patient.

29. The method of claim 14, wherein the one or more therapies other than the anthracycline are selected from the group consisting of surgery, radiation, and a therapeutic agent, wherein the therapeutic agent is selected from the group consisting of irofulven, cisplatin, docetaxel, cabazitaxel, mitoxantrone, estramustine, prednisone, carboplatin, bevacizumab, paclitaxel, gemcitabine, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, arsenic trioxide, bendamustine, fulvestrant, teniposide, decitabine, estramustine, azaguanine, mitomycin, paclitaxel, taxotere, AP0010, ara-c, methylprednisolone, methotrexate, methyl-gag, belinostat, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

30. The method of claim 23, wherein the single-stranded nucleic acid molecules have a length in the range of 20 to 60 nucleotides.

\* \* \* \* \*

```
                        SEQUENCE LISTING

<160> NUMBER OF SEQ ID NOS: 528

<210> SEQ ID NO 1
<211> LENGTH: 25
<212> TYPE: DNA
<213> ORGANISM: Homo sapiens

<400> SEQUENCE: 1
tgatgagctt tcctttgatc cggac                                         25

<210> SEQ ID NO 2
<211> LENGTH: 25
<212> TYPE: DNA
<213> ORGANISM: Homo sapiens

<400> SEQUENCE: 2
cctccatgtc accgcactgt agagg                                         25

<210> SEQ ID NO 3
<211> LENGTH: 25
<212> TYPE: DNA
<213> ORGANISM: Homo sapiens

<400> SEQUENCE: 3
attctctggc atttagtctc ttcaa                                         25

<210> SEQ ID NO 4
<211> LENGTH: 25
<212> TYPE: DNA
<213> ORGANISM: Homo sapiens

<400> SEQUENCE: 4
aagtgtgcag aatactggcc gtcaa                                         25

<210> SEQ ID NO 5
<211> LENGTH: 25
<212> TYPE: DNA
<213> ORGANISM: Homo sapiens

<400> SEQUENCE: 5
ccctccacaa gcagcactgt caaaa                                         25

<210> SEQ ID NO 6
<211> LENGTH: 25
<212> TYPE: DNA
<213> ORGANISM: Homo sapiens

<400> SEQUENCE: 6
ctacaagtga actccttgcc caggc                                         25
```

```
<210> SEQ ID NO 7
<211> LENGTH: 25
<212> TYPE: DNA
<213> ORGANISM: Homo sapiens

<400> SEQUENCE: 7
acacatacat acattgaccc acagg                                          25

<210> SEQ ID NO 8
<211> LENGTH: 25
<212> TYPE: DNA
<213> ORGANISM: Homo sapiens

<400> SEQUENCE: 8
tcccctctca ggtcatgtgt agatg                                          25

<210> SEQ ID NO 9
<211> LENGTH: 25
<212> TYPE: DNA
<213> ORGANISM: Homo sapiens

<400> SEQUENCE: 9
attctttttt ggcaggtagg ctata                                          25

<210> SEQ ID NO 10
<211> LENGTH: 25
<212> TYPE: DNA
<213> ORGANISM: Homo sapiens

<400> SEQUENCE: 10
acctcatgtc cacgcaaagc ttggg                                          25

<210> SEQ ID NO 11
<211> LENGTH: 25
<212> TYPE: DNA
<213> ORGANISM: Homo sapiens

<400> SEQUENCE: 11
gcaggttgca cacagttttg tttat                                          25

<210> SEQ ID NO 12
<211> LENGTH: 25
<212> TYPE: DNA
<213> ORGANISM: Homo sapiens

<400> SEQUENCE: 12
tggagaaaat gacgacccac gacca                                          25

<210> SEQ ID NO 13
<211> LENGTH: 25
<212> TYPE: DNA
<213> ORGANISM: Homo sapiens

<400> SEQUENCE: 13
atcatgctga ggcgccttgc aaatc                                          25

<210> SEQ ID NO 14
<211> LENGTH: 25
<212> TYPE: DNA
<213> ORGANISM: Homo sapiens

<400> SEQUENCE: 14
agagagcctc agtcttactg atttc                                          25
```

```
<210> SEQ ID NO 15
<211> LENGTH: 25
<212> TYPE: DNA
<213> ORGANISM: Homo sapiens

<400> SEQUENCE: 15
tccatctagt gacaagtgac cccca                                           25

<210> SEQ ID NO 16
<211> LENGTH: 25
<212> TYPE: DNA
<213> ORGANISM: Homo sapiens

<400> SEQUENCE: 16
agagatttgg agatgtctct gtgtg                                           25

<210> SEQ ID NO 17
<211> LENGTH: 25
<212> TYPE: DNA
<213> ORGANISM: Homo sapiens

<400> SEQUENCE: 17
gtttaatagc ttttccttct ggact                                           25

<210> SEQ ID NO 18
<211> LENGTH: 25
<212> TYPE: DNA
<213> ORGANISM: Homo sapiens

<400> SEQUENCE: 18
cctgcttcga aatgcctatc gggag                                           25

<210> SEQ ID NO 19
<211> LENGTH: 25
<212> TYPE: DNA
<213> ORGANISM: Homo sapiens

<400> SEQUENCE: 19
ggtgacatat ttacgcttgt gatca                                           25

<210> SEQ ID NO 20
<211> LENGTH: 25
<212> TYPE: DNA
<213> ORGANISM: Homo sapiens

<400> SEQUENCE: 20
gaacagtttg tacagacgta tgctt                                           25

<210> SEQ ID NO 21
<211> LENGTH: 25
<212> TYPE: DNA
<213> ORGANISM: Homo sapiens

<400> SEQUENCE: 21
gaatctaccg tgcaagttca ttatc                                           25

<210> SEQ ID NO 22
<211> LENGTH: 25
<212> TYPE: DNA
<213> ORGANISM: Homo sapiens

<400> SEQUENCE: 22
ggatccaact ggacaacgtg tggga                                           25
```

<210> SEQ ID NO 23
<211> LENGTH: 25
<212> TYPE: DNA
<213> ORGANISM: Homo sapiens

<400> SEQUENCE: 23
ctcatcacat tatcattgca tatca                                    25

<210> SEQ ID NO 24
<211> LENGTH: 25
<212> TYPE: DNA
<213> ORGANISM: Homo sapiens

<400> SEQUENCE: 24
gtctgtgctt cttccataga cagaa                                    25

<210> SEQ ID NO 25
<211> LENGTH: 25
<212> TYPE: DNA
<213> ORGANISM: Homo sapiens

<400> SEQUENCE: 25
aaagggcaag atctcatttc aattt                                    25

<210> SEQ ID NO 26
<211> LENGTH: 25
<212> TYPE: DNA
<213> ORGANISM: Homo sapiens

<400> SEQUENCE: 26
taaccatgct tacacactaa actat                                    25

<210> SEQ ID NO 27
<211> LENGTH: 25
<212> TYPE: DNA
<213> ORGANISM: Homo sapiens

<400> SEQUENCE: 27
attgcatatg catagttccc atgtt                                    25

<210> SEQ ID NO 28
<211> LENGTH: 25
<212> TYPE: DNA
<213> ORGANISM: Homo sapiens

<400> SEQUENCE: 28
gactgacctt gatgagctgt gcaca                                    25

<210> SEQ ID NO 29
<211> LENGTH: 25
<212> TYPE: DNA
<213> ORGANISM: Homo sapiens

<400> SEQUENCE: 29
gtccactaga actctgctgt gtgtc                                    25

<210> SEQ ID NO 30
<211> LENGTH: 25
<212> TYPE: DNA
<213> ORGANISM: Homo sapiens

<400> SEQUENCE: 30
taacatcagc tgcctatgcc tatga                                    25

<210> SEQ ID NO 31
<211> LENGTH: 25
<212> TYPE: DNA
<213> ORGANISM: Homo sapiens

<400> SEQUENCE: 31
gtccctgtaa ctcaaatgtc aaccc                                    25

<210> SEQ ID NO 32
<211> LENGTH: 25
<212> TYPE: DNA
<213> ORGANISM: Homo sapiens

<400> SEQUENCE: 32
ccctgctacg actggcaaag atgag                                    25

<210> SEQ ID NO 33
<211> LENGTH: 25
<212> TYPE: DNA
<213> ORGANISM: Homo sapiens

<400> SEQUENCE: 33
ctaggcacag ctttcataac ccagt                                    25

<210> SEQ ID NO 34
<211> LENGTH: 25
<212> TYPE: DNA
<213> ORGANISM: Homo sapiens

<400> SEQUENCE: 34
aatgccagct gcgtgtctag ttttg                                    25

<210> SEQ ID NO 35
<211> LENGTH: 25
<212> TYPE: DNA
<213> ORGANISM: Homo sapiens

<400> SEQUENCE: 35
tcatcacaga tctgcggaac cagcc                                    25

<210> SEQ ID NO 36
<211> LENGTH: 25
<212> TYPE: DNA
<213> ORGANISM: Homo sapiens

<400> SEQUENCE: 36
gcccagggcc atggaaggac cctta                                    25

<210> SEQ ID NO 37
<211> LENGTH: 25
<212> TYPE: DNA
<213> ORGANISM: Homo sapiens

<400> SEQUENCE: 37
cctcaatgac tccagatact gcctg                                    25

<210> SEQ ID NO 38
<211> LENGTH: 25
<212> TYPE: DNA
<213> ORGANISM: Homo sapiens

<400> SEQUENCE: 38

-continued ggcaggtcgg tgacgtttag cacag                                       25

<210> SEQ ID NO 39
<211> LENGTH: 25
<212> TYPE: DNA
<213> ORGANISM: Homo sapiens

<400> SEQUENCE: 39
gtggtctatg ttggcgtctg gatcc                                       25

<210> SEQ ID NO 40
<211> LENGTH: 25
<212> TYPE: DNA
<213> ORGANISM: Homo sapiens

<400> SEQUENCE: 40
aaacatcttg tctacatcct ttggc                                       25

<210> SEQ ID NO 41
<211> LENGTH: 25
<212> TYPE: DNA
<213> ORGANISM: Homo sapiens

<400> SEQUENCE: 41
tgccgctgtc taacttggtg tgcag                                       25

<210> SEQ ID NO 42
<211> LENGTH: 25
<212> TYPE: DNA
<213> ORGANISM: Homo sapiens

<400> SEQUENCE: 42
acggacatgc ggataaggcc ctgct                                       25

<210> SEQ ID NO 43
<211> LENGTH: 25
<212> TYPE: DNA
<213> ORGANISM: Homo sapiens

<400> SEQUENCE: 43
taagcattcc gtccatctaa gctca                                       25

<210> SEQ ID NO 44
<211> LENGTH: 25
<212> TYPE: DNA
<213> ORGANISM: Homo sapiens

<400> SEQUENCE: 44
gttacaccct aaagcctgaa acctg                                       25

<210> SEQ ID NO 45
<211> LENGTH: 25
<212> TYPE: DNA
<213> ORGANISM: Homo sapiens

<400> SEQUENCE: 45
gcctttcttg ctgttagggg ctacc                                       25

<210> SEQ ID NO 46
<211> LENGTH: 25
<212> TYPE: DNA
<213> ORGANISM: Homo sapiens

```
<400> SEQUENCE: 46
aagaccggca gatggtggtg ctgga                                         25

<210> SEQ ID NO 47
<211> LENGTH: 25
<212> TYPE: DNA
<213> ORGANISM: Homo sapiens

<400> SEQUENCE: 47
cttctccggt ggcatggtgg tagac                                         25

<210> SEQ ID NO 48
<211> LENGTH: 25
<212> TYPE: DNA
<213> ORGANISM: Homo sapiens

<400> SEQUENCE: 48
acacacctag ccagctgtca agggc                                         25

<210> SEQ ID NO 49
<211> LENGTH: 25
<212> TYPE: DNA
<213> ORGANISM: Homo sapiens

<400> SEQUENCE: 49
caagggagct tgcacggtac tgacc                                         25

<210> SEQ ID NO 50
<211> LENGTH: 25
<212> TYPE: DNA
<213> ORGANISM: Homo sapiens

<400> SEQUENCE: 50
agatcctgct agggaaggcc accat                                         25

<210> SEQ ID NO 51
<211> LENGTH: 25
<212> TYPE: DNA
<213> ORGANISM: Homo sapiens

<400> SEQUENCE: 51
ctgacacgga acaccaggtc tgctc                                         25

<210> SEQ ID NO 52
<211> LENGTH: 25
<212> TYPE: DNA
<213> ORGANISM: Homo sapiens

<400> SEQUENCE: 52
tcatgagtga ctgctggatc tacaa                                         25

<210> SEQ ID NO 53
<211> LENGTH: 25
<212> TYPE: DNA
<213> ORGANISM: Homo sapiens

<400> SEQUENCE: 53
tctttagaac tagtcgtctc ctctt                                         25

<210> SEQ ID NO 54
<211> LENGTH: 25
<212> TYPE: DNA
<213> ORGANISM: Homo sapiens
```

```
<400> SEQUENCE: 54
agctgctcac aactgggtca acgct                                             25

<210> SEQ ID NO 55
<211> LENGTH: 25
<212> TYPE: DNA
<213> ORGANISM: Homo sapiens

<400> SEQUENCE: 55
gtctgtggct accagttaca ctgag                                             25

<210> SEQ ID NO 56
<211> LENGTH: 25
<212> TYPE: DNA
<213> ORGANISM: Homo sapiens

<400> SEQUENCE: 56
caaggggcag acagctagga ctcag                                             25

<210> SEQ ID NO 57
<211> LENGTH: 25
<212> TYPE: DNA
<213> ORGANISM: Homo sapiens

<400> SEQUENCE: 57
cttttccgca cagctgtgtt gactt                                             25

<210> SEQ ID NO 58
<211> LENGTH: 25
<212> TYPE: DNA
<213> ORGANISM: Homo sapiens

<400> SEQUENCE: 58
gaggcagcgg gatggactac atgac                                             25

<210> SEQ ID NO 59
<211> LENGTH: 25
<212> TYPE: DNA
<213> ORGANISM: Homo sapiens

<400> SEQUENCE: 59
acagtgtcct acagagaaca tggct                                             25

<210> SEQ ID NO 60
<211> LENGTH: 25
<212> TYPE: DNA
<213> ORGANISM: Homo sapiens

<400> SEQUENCE: 60
atcccagagg acccataagt gccgg                                             25

<210> SEQ ID NO 61
<211> LENGTH: 25
<212> TYPE: DNA
<213> ORGANISM: Homo sapiens

<400> SEQUENCE: 61
gaagggagca ttgtagcctg ctgta                                             25

<210> SEQ ID NO 62
<211> LENGTH: 25
<212> TYPE: DNA
```

<213> ORGANISM: Homo sapiens

<400> SEQUENCE: 62
ggttggactg ctcatggatt ttgta                                25

<210> SEQ ID NO 63
<211> LENGTH: 25
<212> TYPE: DNA
<213> ORGANISM: Homo sapiens

<400> SEQUENCE: 63
caatacacat tcttcttttg ccagc                                25

<210> SEQ ID NO 64
<211> LENGTH: 25
<212> TYPE: DNA
<213> ORGANISM: Homo sapiens

<400> SEQUENCE: 64
gaccccacca ctgtgggttg caggc                                25

<210> SEQ ID NO 65
<211> LENGTH: 25
<212> TYPE: DNA
<213> ORGANISM: Homo sapiens

<400> SEQUENCE: 65
acaatgttga gttcagcatg tgtct                                25

<210> SEQ ID NO 66
<211> LENGTH: 25
<212> TYPE: DNA
<213> ORGANISM: Homo sapiens

<400> SEQUENCE: 66
gccatccatt cagtcgattc agtca                                25

<210> SEQ ID NO 67
<211> LENGTH: 25
<212> TYPE: DNA
<213> ORGANISM: Homo sapiens

<400> SEQUENCE: 67
ggcagctatc ttacagacgc atgaa                                25

<210> SEQ ID NO 68
<211> LENGTH: 25
<212> TYPE: DNA
<213> ORGANISM: Homo sapiens

<400> SEQUENCE: 68
taggaaatga cagacccaac cacca                                25

<210> SEQ ID NO 69
<211> LENGTH: 25
<212> TYPE: DNA
<213> ORGANISM: Homo sapiens

<400> SEQUENCE: 69
cacgcactca cctctgtgag cagag                                25

<210> SEQ ID NO 70
<211> LENGTH: 25

```
<212> TYPE: DNA
<213> ORGANISM: Homo sapiens

<400> SEQUENCE: 70
tctcacattg gtgcatctct tcatg                                          25

<210> SEQ ID NO 71
<211> LENGTH: 25
<212> TYPE: DNA
<213> ORGANISM: Homo sapiens

<400> SEQUENCE: 71
ccggcagagc ggactgtacg acagc                                          25

<210> SEQ ID NO 72
<211> LENGTH: 25
<212> TYPE: DNA
<213> ORGANISM: Homo sapiens

<400> SEQUENCE: 72
aaaggctgca gtatgtctat attct                                          25

<210> SEQ ID NO 73
<211> LENGTH: 25
<212> TYPE: DNA
<213> ORGANISM: Homo sapiens

<400> SEQUENCE: 73
gctgtccaat atgtagccgc tagcc                                          25

<210> SEQ ID NO 74
<211> LENGTH: 25
<212> TYPE: DNA
<213> ORGANISM: Homo sapiens

<400> SEQUENCE: 74
ttcttgcact acaggcactc aataa                                          25

<210> SEQ ID NO 75
<211> LENGTH: 25
<212> TYPE: DNA
<213> ORGANISM: Homo sapiens

<400> SEQUENCE: 75
gtctcttgag agagcctctt tgcat                                          25

<210> SEQ ID NO 76
<211> LENGTH: 25
<212> TYPE: DNA
<213> ORGANISM: Homo sapiens

<400> SEQUENCE: 76
gtaccggtta cagtacttgg cctct                                          25

<210> SEQ ID NO 77
<211> LENGTH: 25
<212> TYPE: DNA
<213> ORGANISM: Homo sapiens

<400> SEQUENCE: 77
atgtccttcg gagttaccta gcgga                                          25

<210> SEQ ID NO 78
```

```
<211> LENGTH: 25
<212> TYPE: DNA
<213> ORGANISM: Homo sapiens

<400> SEQUENCE: 78
gttaagttat gcctgtgcaa agaag                                              25

<210> SEQ ID NO 79
<211> LENGTH: 25
<212> TYPE: DNA
<213> ORGANISM: Homo sapiens

<400> SEQUENCE: 79
ctatctgtgt ccatgaagtc ttact                                              25

<210> SEQ ID NO 80
<211> LENGTH: 25
<212> TYPE: DNA
<213> ORGANISM: Homo sapiens

<400> SEQUENCE: 80
tttagaacct gcttctctga tctgt                                              25

<210> SEQ ID NO 81
<211> LENGTH: 25
<212> TYPE: DNA
<213> ORGANISM: Homo sapiens

<400> SEQUENCE: 81
aaaccgctgc ggcggtatct gacct                                              25

<210> SEQ ID NO 82
<211> LENGTH: 25
<212> TYPE: DNA
<213> ORGANISM: Homo sapiens

<400> SEQUENCE: 82
gcctgagtgc ttgggttacc atgga                                              25

<210> SEQ ID NO 83
<211> LENGTH: 25
<212> TYPE: DNA
<213> ORGANISM: Homo sapiens

<400> SEQUENCE: 83
ccaaacctcg ccagagaagc tcttc                                              25

<210> SEQ ID NO 84
<211> LENGTH: 25
<212> TYPE: DNA
<213> ORGANISM: Homo sapiens

<400> SEQUENCE: 84
tgtggttgat agccagtcac tgcct                                              25

<210> SEQ ID NO 85
<211> LENGTH: 25
<212> TYPE: DNA
<213> ORGANISM: Homo sapiens

<400> SEQUENCE: 85
cagccgtgtc aaagtcacag tgtct                                              25
```

```
<210> SEQ ID NO 86
<211> LENGTH: 25
<212> TYPE: DNA
<213> ORGANISM: Homo sapiens

<400> SEQUENCE: 86
accgaaactg gcatcttact cttgg                                          25

<210> SEQ ID NO 87
<211> LENGTH: 25
<212> TYPE: DNA
<213> ORGANISM: Homo sapiens

<400> SEQUENCE: 87
aaatcttagg tttgcttatg cccag                                          25

<210> SEQ ID NO 88
<211> LENGTH: 25
<212> TYPE: DNA
<213> ORGANISM: Homo sapiens

<400> SEQUENCE: 88
cgccacattt tagccgtact ttgct                                          25

<210> SEQ ID NO 89
<211> LENGTH: 25
<212> TYPE: DNA
<213> ORGANISM: Homo sapiens

<400> SEQUENCE: 89
gctcatcggc tatcgttagt gctag                                          25

<210> SEQ ID NO 90
<211> LENGTH: 25
<212> TYPE: DNA
<213> ORGANISM: Homo sapiens

<400> SEQUENCE: 90
attgatgtgt gtctaggcag gacct                                          25

<210> SEQ ID NO 91
<211> LENGTH: 25
<212> TYPE: DNA
<213> ORGANISM: Homo sapiens

<400> SEQUENCE: 91
taaaggtagt ggtgtgtctc gaccc                                          25

<210> SEQ ID NO 92
<211> LENGTH: 25
<212> TYPE: DNA
<213> ORGANISM: Homo sapiens

<400> SEQUENCE: 92
aacagtcatg tggctcgcag atgca                                          25

<210> SEQ ID NO 93
<211> LENGTH: 25
<212> TYPE: DNA
<213> ORGANISM: Homo sapiens

<400> SEQUENCE: 93
ccgtcgactc tccatttaaa ttgtt                                          25
```

<210> SEQ ID NO 94
<211> LENGTH: 25
<212> TYPE: DNA
<213> ORGANISM: Homo sapiens

<400> SEQUENCE: 94
catgagccat catcatgtct cctct                                              25

<210> SEQ ID NO 95
<211> LENGTH: 25
<212> TYPE: DNA
<213> ORGANISM: Homo sapiens

<400> SEQUENCE: 95
tatctctcca tgttcagttc caagg                                              25

<210> SEQ ID NO 96
<211> LENGTH: 25
<212> TYPE: DNA
<213> ORGANISM: Homo sapiens

<400> SEQUENCE: 96
cacccaccag attgttacta cagtg                                              25

<210> SEQ ID NO 97
<211> LENGTH: 25
<212> TYPE: DNA
<213> ORGANISM: Homo sapiens

<400> SEQUENCE: 97
gaagctcata tcttatctct gttct                                              25

<210> SEQ ID NO 98
<211> LENGTH: 25
<212> TYPE: DNA
<213> ORGANISM: Homo sapiens

<400> SEQUENCE: 98
ttcaacaggc acattatttc cccct                                              25

<210> SEQ ID NO 99
<211> LENGTH: 25
<212> TYPE: DNA
<213> ORGANISM: Homo sapiens

<400> SEQUENCE: 99
ggtaaatcca tccttattgt ataga                                              25

<210> SEQ ID NO 100
<211> LENGTH: 25
<212> TYPE: DNA
<213> ORGANISM: Homo sapiens

<400> SEQUENCE: 100
gagaattttt tgtacgatca gcctt                                              25

<210> SEQ ID NO 101
<211> LENGTH: 25
<212> TYPE: DNA
<213> ORGANISM: Homo sapiens

<400> SEQUENCE: 101
gtgctgttgc tcttatctgc aaggt                                              25

<210> SEQ ID NO 102
<211> LENGTH: 25
<212> TYPE: DNA
<213> ORGANISM: Homo sapiens

<400> SEQUENCE: 102
cagtacttac ccttggctaa gaact                                              25

<210> SEQ ID NO 103
<211> LENGTH: 25
<212> TYPE: DNA
<213> ORGANISM: Homo sapiens

<400> SEQUENCE: 103
tggcagtggc tacggtggag accga                                              25

<210> SEQ ID NO 104
<211> LENGTH: 25
<212> TYPE: DNA
<213> ORGANISM: Homo sapiens

<400> SEQUENCE: 104
cttccttcaa gatcctggct gggga                                              25

<210> SEQ ID NO 105
<211> LENGTH: 25
<212> TYPE: DNA
<213> ORGANISM: Homo sapiens

<400> SEQUENCE: 105
cactcttctt gcagctgttg agcgc                                              25

<210> SEQ ID NO 106
<211> LENGTH: 25
<212> TYPE: DNA
<213> ORGANISM: Homo sapiens

<400> SEQUENCE: 106
tgaccatgtt tcctctcaat aaagt                                              25

<210> SEQ ID NO 107
<211> LENGTH: 25
<212> TYPE: DNA
<213> ORGANISM: Homo sapiens

<400> SEQUENCE: 107
aaactgtttg cctgtggtag acacc                                              25

<210> SEQ ID NO 108
<211> LENGTH: 25
<212> TYPE: DNA
<213> ORGANISM: Homo sapiens

<400> SEQUENCE: 108
tgggtgtgac catgtttcct ctcaa                                              25

<210> SEQ ID NO 109
<211> LENGTH: 25
<212> TYPE: DNA
<213> ORGANISM: Homo sapiens

<400> SEQUENCE: 109
ctcacccagg caatcttgcc ttctg                                              25

<210> SEQ ID NO 110
<211> LENGTH: 25
<212> TYPE: DNA
<213> ORGANISM: Homo sapiens

<400> SEQUENCE: 110
aaatcccctc agaggtgtga ctagt                                              25

<210> SEQ ID NO 111
<211> LENGTH: 25
<212> TYPE: DNA
<213> ORGANISM: Homo sapiens

<400> SEQUENCE: 111
gtgcagatgt gataagtccc cgagg                                              25

<210> SEQ ID NO 112
<211> LENGTH: 25
<212> TYPE: DNA
<213> ORGANISM: Homo sapiens

<400> SEQUENCE: 112
gtaacgtgat tgattcagta tctta                                              25

<210> SEQ ID NO 113
<211> LENGTH: 25
<212> TYPE: DNA
<213> ORGANISM: Homo sapiens

<400> SEQUENCE: 113
tgatgccagt tatcatgctg ccact                                              25

<210> SEQ ID NO 114
<211> LENGTH: 25
<212> TYPE: DNA
<213> ORGANISM: Homo sapiens

<400> SEQUENCE: 114
caagcccctg tattttgctg atcgg                                              25

<210> SEQ ID NO 115
<211> LENGTH: 25
<212> TYPE: DNA
<213> ORGANISM: Homo sapiens

<400> SEQUENCE: 115
aagtatccct actgtaattt gtgat                                              25

<210> SEQ ID NO 116
<211> LENGTH: 25
<212> TYPE: DNA
<213> ORGANISM: Homo sapiens

<400> SEQUENCE: 116
tcaaggcgct gcacgttgac tcagc                                              25

<210> SEQ ID NO 117
<211> LENGTH: 25
<212> TYPE: DNA
<213> ORGANISM: Homo sapiens

<400> SEQUENCE: 117
ctcaccatgc ttccagctaa caggt                                          25

<210> SEQ ID NO 118
<211> LENGTH: 25
<212> TYPE: DNA
<213> ORGANISM: Homo sapiens

<400> SEQUENCE: 118
agctacctca ggtgttttta cctca                                          25

<210> SEQ ID NO 119
<211> LENGTH: 25
<212> TYPE: DNA
<213> ORGANISM: Homo sapiens

<400> SEQUENCE: 119
aagtctacag gggctggtga cctct                                          25

<210> SEQ ID NO 120
<211> LENGTH: 25
<212> TYPE: DNA
<213> ORGANISM: Homo sapiens

<400> SEQUENCE: 120
agcaagctgc cgaaccaaaa gaatt                                          25

<210> SEQ ID NO 121
<211> LENGTH: 25
<212> TYPE: DNA
<213> ORGANISM: Homo sapiens

<400> SEQUENCE: 121
gcacatttga tatagctctt tttct                                          25

<210> SEQ ID NO 122
<211> LENGTH: 25
<212> TYPE: DNA
<213> ORGANISM: Homo sapiens

<400> SEQUENCE: 122
tttttgtgct gtgaacattt tctgc                                          25

<210> SEQ ID NO 123
<211> LENGTH: 25
<212> TYPE: DNA
<213> ORGANISM: Homo sapiens

<400> SEQUENCE: 123
ctctcacact gttgtctgtt actga                                          25

<210> SEQ ID NO 124
<211> LENGTH: 25
<212> TYPE: DNA
<213> ORGANISM: Homo sapiens

<400> SEQUENCE: 124
gacgttttct acgtagcttt tgtat                                          25

<210> SEQ ID NO 125
<211> LENGTH: 25
<212> TYPE: DNA
<213> ORGANISM: Homo sapiens

```
<400> SEQUENCE: 125
agaggcagta accatgcccg catag                                  25

<210> SEQ ID NO 126
<211> LENGTH: 25
<212> TYPE: DNA
<213> ORGANISM: Homo sapiens

<400> SEQUENCE: 126
accagcttgc gaataacagt ccccg                                  25

<210> SEQ ID NO 127
<211> LENGTH: 25
<212> TYPE: DNA
<213> ORGANISM: Homo sapiens

<400> SEQUENCE: 127
tccccaaact tgctgtcaat tccga                                  25

<210> SEQ ID NO 128
<211> LENGTH: 25
<212> TYPE: DNA
<213> ORGANISM: Homo sapiens

<400> SEQUENCE: 128
agagcatacc cttgtatagc ttcag                                  25

<210> SEQ ID NO 129
<211> LENGTH: 25
<212> TYPE: DNA
<213> ORGANISM: Homo sapiens

<400> SEQUENCE: 129
tccttgtatg cgcttttttac cttga                                 25

<210> SEQ ID NO 130
<211> LENGTH: 25
<212> TYPE: DNA
<213> ORGANISM: Homo sapiens

<400> SEQUENCE: 130
ctgatcagaa tcatggtctc ccgca                                  25

<210> SEQ ID NO 131
<211> LENGTH: 25
<212> TYPE: DNA
<213> ORGANISM: Homo sapiens

<400> SEQUENCE: 131
agaatccctt cagttttagc tacca                                  25

<210> SEQ ID NO 132
<211> LENGTH: 25
<212> TYPE: DNA
<213> ORGANISM: Homo sapiens

<400> SEQUENCE: 132
agtactggtt gaacctgacc acttc                                  25

<210> SEQ ID NO 133
<211> LENGTH: 25
<212> TYPE: DNA
<213> ORGANISM: Homo sapiens
```

```
<400> SEQUENCE: 133
tggagcctgc agctagcagt gggcc                                          25

<210> SEQ ID NO 134
<211> LENGTH: 25
<212> TYPE: DNA
<213> ORGANISM: Homo sapiens

<400> SEQUENCE: 134
ggatgccttt tcacatcatt tcagt                                          25

<210> SEQ ID NO 135
<211> LENGTH: 25
<212> TYPE: DNA
<213> ORGANISM: Homo sapiens

<400> SEQUENCE: 135
tcctgctgca ccttgagtca gagct                                          25

<210> SEQ ID NO 136
<211> LENGTH: 25
<212> TYPE: DNA
<213> ORGANISM: Homo sapiens

<400> SEQUENCE: 136
cagagctctg ggttgtgcac atttc                                          25

<210> SEQ ID NO 137
<211> LENGTH: 25
<212> TYPE: DNA
<213> ORGANISM: Homo sapiens

<400> SEQUENCE: 137
gtagaattct tcctgtacga ttggg                                          25

<210> SEQ ID NO 138
<211> LENGTH: 25
<212> TYPE: DNA
<213> ORGANISM: Homo sapiens

<400> SEQUENCE: 138
aatcgttctc cttacaatca agttc                                          25

<210> SEQ ID NO 139
<211> LENGTH: 25
<212> TYPE: DNA
<213> ORGANISM: Homo sapiens

<400> SEQUENCE: 139
aacagtgtgc aaatggcagc tagag                                          25

<210> SEQ ID NO 140
<211> LENGTH: 25
<212> TYPE: DNA
<213> ORGANISM: Homo sapiens

<400> SEQUENCE: 140
acatggggtg acatgcctcg tatgt                                          25

<210> SEQ ID NO 141
<211> LENGTH: 25
<212> TYPE: DNA
```

```
<213> ORGANISM: Homo sapiens

<400> SEQUENCE: 141
gaatggtatt cgtttcacct gttgt                                              25

<210> SEQ ID NO 142
<211> LENGTH: 25
<212> TYPE: DNA
<213> ORGANISM: Homo sapiens

<400> SEQUENCE: 142
caggggaacc ttccaaggtg tctgg                                              25

<210> SEQ ID NO 143
<211> LENGTH: 25
<212> TYPE: DNA
<213> ORGANISM: Homo sapiens

<400> SEQUENCE: 143
atatgcctgt tagaccttag ctgtg                                              25

<210> SEQ ID NO 144
<211> LENGTH: 25
<212> TYPE: DNA
<213> ORGANISM: Homo sapiens

<400> SEQUENCE: 144
gactaaatgc tacctgggtt tccag                                              25

<210> SEQ ID NO 145
<211> LENGTH: 25
<212> TYPE: DNA
<213> ORGANISM: Homo sapiens

<400> SEQUENCE: 145
ttctggaaca cattgctgca ctttg                                              25

<210> SEQ ID NO 146
<211> LENGTH: 25
<212> TYPE: DNA
<213> ORGANISM: Homo sapiens

<400> SEQUENCE: 146
gccagcgctt ctggtctggt aaata                                              25

<210> SEQ ID NO 147
<211> LENGTH: 25
<212> TYPE: DNA
<213> ORGANISM: Homo sapiens

<400> SEQUENCE: 147
gttactggct tctcttgagt cacac                                              25

<210> SEQ ID NO 148
<211> LENGTH: 25
<212> TYPE: DNA
<213> ORGANISM: Homo sapiens

<400> SEQUENCE: 148
attgttgaat ggtgtcatgc aaagg                                              25

<210> SEQ ID NO 149
<211> LENGTH: 25
```

<212> TYPE: DNA
<213> ORGANISM: Homo sapiens

<400> SEQUENCE: 149
gataagtttc tattctgtca gtgtt                                              25

<210> SEQ ID NO 150
<211> LENGTH: 25
<212> TYPE: DNA
<213> ORGANISM: Homo sapiens

<400> SEQUENCE: 150
cacgtaaatg cgtccctgta cagat                                              25

<210> SEQ ID NO 151
<211> LENGTH: 25
<212> TYPE: DNA
<213> ORGANISM: Homo sapiens

<400> SEQUENCE: 151
gagtgggagc cgtgaatatc tctgt                                              25

<210> SEQ ID NO 152
<211> LENGTH: 25
<212> TYPE: DNA
<213> ORGANISM: Homo sapiens

<400> SEQUENCE: 152
tttatagtga cccaccctag atctt                                              25

<210> SEQ ID NO 153
<211> LENGTH: 25
<212> TYPE: DNA
<213> ORGANISM: Homo sapiens

<400> SEQUENCE: 153
agtcccaact ccagtaaaga cactc                                              25

<210> SEQ ID NO 154
<211> LENGTH: 25
<212> TYPE: DNA
<213> ORGANISM: Homo sapiens

<400> SEQUENCE: 154
gtgttattgc tgttattgtg gttgt                                              25

<210> SEQ ID NO 155
<211> LENGTH: 25
<212> TYPE: DNA
<213> ORGANISM: Homo sapiens

<400> SEQUENCE: 155
aggccaagaa gcctgcactg gtggc                                              25

<210> SEQ ID NO 156
<211> LENGTH: 25
<212> TYPE: DNA
<213> ORGANISM: Homo sapiens

<400> SEQUENCE: 156
gcttttattc gtcctttgac aaaag                                              25

<210> SEQ ID NO 157

```
<211> LENGTH: 25
<212> TYPE: DNA
<213> ORGANISM: Homo sapiens

<400> SEQUENCE: 157
gagcagatca ggacacttag caaat                                              25

<210> SEQ ID NO 158
<211> LENGTH: 25
<212> TYPE: DNA
<213> ORGANISM: Homo sapiens

<400> SEQUENCE: 158
gctgcagatc gaggactttc tggag                                              25

<210> SEQ ID NO 159
<211> LENGTH: 25
<212> TYPE: DNA
<213> ORGANISM: Homo sapiens

<400> SEQUENCE: 159
atgagtatcc ctgtaggtca cctgc                                              25

<210> SEQ ID NO 160
<211> LENGTH: 25
<212> TYPE: DNA
<213> ORGANISM: Homo sapiens

<400> SEQUENCE: 160
acaagggtca gtctgtcggg tgggg                                              25

<210> SEQ ID NO 161
<211> LENGTH: 25
<212> TYPE: DNA
<213> ORGANISM: Homo sapiens

<400> SEQUENCE: 161
gatgcaggcc tgagtgtgtg cggga                                              25

<210> SEQ ID NO 162
<211> LENGTH: 25
<212> TYPE: DNA
<213> ORGANISM: Homo sapiens

<400> SEQUENCE: 162
aagccttcag agggtttgga ccaca                                              25

<210> SEQ ID NO 163
<211> LENGTH: 25
<212> TYPE: DNA
<213> ORGANISM: Homo sapiens

<400> SEQUENCE: 163
ccaccgctct catttcatgg agtct                                              25

<210> SEQ ID NO 164
<211> LENGTH: 25
<212> TYPE: DNA
<213> ORGANISM: Homo sapiens

<400> SEQUENCE: 164
ctgagcttcg gttctccaga atgta                                              25
```

```
<210> SEQ ID NO 165
<211> LENGTH: 25
<212> TYPE: DNA
<213> ORGANISM: Homo sapiens

<400> SEQUENCE: 165
aaaggcttcc aggctgagag ccggc                                              25

<210> SEQ ID NO 166
<211> LENGTH: 25
<212> TYPE: DNA
<213> ORGANISM: Homo sapiens

<400> SEQUENCE: 166
aggtggcagg gatggctccg aagcc                                              25

<210> SEQ ID NO 167
<211> LENGTH: 25
<212> TYPE: DNA
<213> ORGANISM: Homo sapiens

<400> SEQUENCE: 167
gtaacccaag cctatttcac agcaa                                              25

<210> SEQ ID NO 168
<211> LENGTH: 25
<212> TYPE: DNA
<213> ORGANISM: Homo sapiens

<400> SEQUENCE: 168
ttaaaagtca tggatctcaa tctca                                              25

<210> SEQ ID NO 169
<211> LENGTH: 25
<212> TYPE: DNA
<213> ORGANISM: Homo sapiens

<400> SEQUENCE: 169
gtattggcaa tcatgacacc tgtaa                                              25

<210> SEQ ID NO 170
<211> LENGTH: 25
<212> TYPE: DNA
<213> ORGANISM: Homo sapiens

<400> SEQUENCE: 170
ggtgattctg agcgagatct tcctg                                              25

<210> SEQ ID NO 171
<211> LENGTH: 25
<212> TYPE: DNA
<213> ORGANISM: Homo sapiens

<400> SEQUENCE: 171
gtacagccag ttcttttatg caaaa                                              25

<210> SEQ ID NO 172
<211> LENGTH: 25
<212> TYPE: DNA
<213> ORGANISM: Homo sapiens

<400> SEQUENCE: 172
acttttcact tatctcatgt tagct                                              25
```

```
<210> SEQ ID NO 173
<211> LENGTH: 25
<212> TYPE: DNA
<213> ORGANISM: Homo sapiens

<400> SEQUENCE: 173
cagtggaacc aaattttgc catta                                  25

<210> SEQ ID NO 174
<211> LENGTH: 25
<212> TYPE: DNA
<213> ORGANISM: Homo sapiens

<400> SEQUENCE: 174
cagcaaccta catgaacttg ggccc                                 25

<210> SEQ ID NO 175
<211> LENGTH: 25
<212> TYPE: DNA
<213> ORGANISM: Homo sapiens

<400> SEQUENCE: 175
gaaatcgcca gcttcgataa ggcca                                 25

<210> SEQ ID NO 176
<211> LENGTH: 25
<212> TYPE: DNA
<213> ORGANISM: Homo sapiens

<400> SEQUENCE: 176
tacagaccat attacctgga ttacc                                 25

<210> SEQ ID NO 177
<211> LENGTH: 25
<212> TYPE: DNA
<213> ORGANISM: Homo sapiens

<400> SEQUENCE: 177
ctgacccagg acccaacatg gtcta                                 25

<210> SEQ ID NO 178
<211> LENGTH: 25
<212> TYPE: DNA
<213> ORGANISM: Homo sapiens

<400> SEQUENCE: 178
tgctatagcg ccattcccaa ggcat                                 25

<210> SEQ ID NO 179
<211> LENGTH: 25
<212> TYPE: DNA
<213> ORGANISM: Homo sapiens

<400> SEQUENCE: 179
atttgctcaa taactctact cattt                                 25

<210> SEQ ID NO 180
<211> LENGTH: 25
<212> TYPE: DNA
<213> ORGANISM: Homo sapiens

<400> SEQUENCE: 180
tacacacagt ttttccgact tttca                                 25
```

<210> SEQ ID NO 181
<211> LENGTH: 25
<212> TYPE: DNA
<213> ORGANISM: Homo sapiens

<400> SEQUENCE: 181
agagccagat tgtgccaact atcca                                           25

<210> SEQ ID NO 182
<211> LENGTH: 25
<212> TYPE: DNA
<213> ORGANISM: Homo sapiens

<400> SEQUENCE: 182
ccagggcaag ttcccagatc ctatg                                           25

<210> SEQ ID NO 183
<211> LENGTH: 25
<212> TYPE: DNA
<213> ORGANISM: Homo sapiens

<400> SEQUENCE: 183
gacagttgca ctacatcaaa tcttt                                           25

<210> SEQ ID NO 184
<211> LENGTH: 25
<212> TYPE: DNA
<213> ORGANISM: Homo sapiens

<400> SEQUENCE: 184
caaccccgag tatctcaaca ctgtc                                           25

<210> SEQ ID NO 185
<211> LENGTH: 25
<212> TYPE: DNA
<213> ORGANISM: Homo sapiens

<400> SEQUENCE: 185
ttatgctcaa tattcccaga atagt                                           25

<210> SEQ ID NO 186
<211> LENGTH: 25
<212> TYPE: DNA
<213> ORGANISM: Homo sapiens

<400> SEQUENCE: 186
cagacggagg tcaggtcttc ctctt                                           25

<210> SEQ ID NO 187
<211> LENGTH: 25
<212> TYPE: DNA
<213> ORGANISM: Homo sapiens

<400> SEQUENCE: 187
acatccagaa agagtccacc ctgca                                           25

<210> SEQ ID NO 188
<211> LENGTH: 25
<212> TYPE: DNA
<213> ORGANISM: Homo sapiens

<400> SEQUENCE: 188

-continued gcttgttcgt ctcactggtg tgagc                                      25

<210> SEQ ID NO 189
<211> LENGTH: 25
<212> TYPE: DNA
<213> ORGANISM: Homo sapiens

<400> SEQUENCE: 189
ggaagaagat caacgcctca ctgaa                                      25

<210> SEQ ID NO 190
<211> LENGTH: 25
<212> TYPE: DNA
<213> ORGANISM: Homo sapiens

<400> SEQUENCE: 190
tcttggtctg gcactaaatt tctca                                      25

<210> SEQ ID NO 191
<211> LENGTH: 25
<212> TYPE: DNA
<213> ORGANISM: Homo sapiens

<400> SEQUENCE: 191
gcttgatctg ttgatgcttt ctctc                                      25

<210> SEQ ID NO 192
<211> LENGTH: 25
<212> TYPE: DNA
<213> ORGANISM: Homo sapiens

<400> SEQUENCE: 192
ggctgctgtg tcatctttga agtca                                      25

<210> SEQ ID NO 193
<211> LENGTH: 25
<212> TYPE: DNA
<213> ORGANISM: Homo sapiens

<400> SEQUENCE: 193
ttaagggctt tatgtgaact atgat                                      25

<210> SEQ ID NO 194
<211> LENGTH: 25
<212> TYPE: DNA
<213> ORGANISM: Homo sapiens

<400> SEQUENCE: 194
agctggctgc catgattgtt tccat                                      25

<210> SEQ ID NO 195
<211> LENGTH: 25
<212> TYPE: DNA
<213> ORGANISM: Homo sapiens

<400> SEQUENCE: 195
aagtgggctt gattctgcag taaat                                      25

<210> SEQ ID NO 196
<211> LENGTH: 25
<212> TYPE: DNA
<213> ORGANISM: Homo sapiens

<400> SEQUENCE: 196
tgaaaacgag ctttctttcc catga                                          25

<210> SEQ ID NO 197
<211> LENGTH: 25
<212> TYPE: DNA
<213> ORGANISM: Homo sapiens

<400> SEQUENCE: 197
atgagttatc atcttagctg tgtta                                          25

<210> SEQ ID NO 198
<211> LENGTH: 25
<212> TYPE: DNA
<213> ORGANISM: Homo sapiens

<400> SEQUENCE: 198
gatgccagaa ggaaagccga aatgc                                          25

<210> SEQ ID NO 199
<211> LENGTH: 25
<212> TYPE: DNA
<213> ORGANISM: Homo sapiens

<400> SEQUENCE: 199
gctgtggatc tgtttggcca gggtc                                          25

<210> SEQ ID NO 200
<211> LENGTH: 25
<212> TYPE: DNA
<213> ORGANISM: Homo sapiens

<400> SEQUENCE: 200
accaagaagc tactggacct cgttc                                          25

<210> SEQ ID NO 201
<211> LENGTH: 25
<212> TYPE: DNA
<213> ORGANISM: Homo sapiens

<400> SEQUENCE: 201
ggccctgcat gtcagatggc gtggt                                          25

<210> SEQ ID NO 202
<211> LENGTH: 25
<212> TYPE: DNA
<213> ORGANISM: Homo sapiens

<400> SEQUENCE: 202
tcgccaccta caggaagctg ctgga                                          25

<210> SEQ ID NO 203
<211> LENGTH: 25
<212> TYPE: DNA
<213> ORGANISM: Homo sapiens

<400> SEQUENCE: 203
gtctctgagt tacaaaagtg ctaat                                          25

<210> SEQ ID NO 204
<211> LENGTH: 25
<212> TYPE: DNA
<213> ORGANISM: Homo sapiens

```
<400> SEQUENCE: 204
acttggctca gtggaagccc tcttt                                    25

<210> SEQ ID NO 205
<211> LENGTH: 25
<212> TYPE: DNA
<213> ORGANISM: Homo sapiens

<400> SEQUENCE: 205
acattgcccg gaaactcagt ctatt                                    25

<210> SEQ ID NO 206
<211> LENGTH: 25
<212> TYPE: DNA
<213> ORGANISM: Homo sapiens

<400> SEQUENCE: 206
tgtaatcacc tgtgcagcct tttgt                                    25

<210> SEQ ID NO 207
<211> LENGTH: 25
<212> TYPE: DNA
<213> ORGANISM: Homo sapiens

<400> SEQUENCE: 207
gcttttaatt atctacagct atttt                                    25

<210> SEQ ID NO 208
<211> LENGTH: 25
<212> TYPE: DNA
<213> ORGANISM: Homo sapiens

<400> SEQUENCE: 208
ttccacaagt actcctgcca agagg                                    25

<210> SEQ ID NO 209
<211> LENGTH: 25
<212> TYPE: DNA
<213> ORGANISM: Homo sapiens

<400> SEQUENCE: 209
tgggcctgtc tactggcgag aagga                                    25

<210> SEQ ID NO 210
<211> LENGTH: 25
<212> TYPE: DNA
<213> ORGANISM: Homo sapiens

<400> SEQUENCE: 210
gaagctctgg aggaactgca actgg                                    25

<210> SEQ ID NO 211
<211> LENGTH: 25
<212> TYPE: DNA
<213> ORGANISM: Homo sapiens

<400> SEQUENCE: 211
gaatgcagaa gcgctccagt atctc                                    25

<210> SEQ ID NO 212
<211> LENGTH: 25
<212> TYPE: DNA
<213> ORGANISM: Homo sapiens
```

-continued

<400> SEQUENCE: 212
atcaccattg atatctcctt gtgga                                              25

<210> SEQ ID NO 213
<211> LENGTH: 25
<212> TYPE: DNA
<213> ORGANISM: Homo sapiens

<400> SEQUENCE: 213
gagtgtccac tattgattgt attat                                              25

<210> SEQ ID NO 214
<211> LENGTH: 25
<212> TYPE: DNA
<213> ORGANISM: Homo sapiens

<400> SEQUENCE: 214
gacagtagcg actacagcat tcctt                                              25

<210> SEQ ID NO 215
<211> LENGTH: 25
<212> TYPE: DNA
<213> ORGANISM: Homo sapiens

<400> SEQUENCE: 215
aacagcaacg cttcggtcag ggtat                                              25

<210> SEQ ID NO 216
<211> LENGTH: 25
<212> TYPE: DNA
<213> ORGANISM: Homo sapiens

<400> SEQUENCE: 216
cccgactcct gctgcattaa tgtta                                              25

<210> SEQ ID NO 217
<211> LENGTH: 25
<212> TYPE: DNA
<213> ORGANISM: Homo sapiens

<400> SEQUENCE: 217
cacacatgcc actatgagct ttcag                                              25

<210> SEQ ID NO 218
<211> LENGTH: 25
<212> TYPE: DNA
<213> ORGANISM: Homo sapiens

<400> SEQUENCE: 218
aatgcaggtc tcttggtatt tattg                                              25

<210> SEQ ID NO 219
<211> LENGTH: 25
<212> TYPE: DNA
<213> ORGANISM: Homo sapiens

<400> SEQUENCE: 219
agtgagtcac atcctgggat ccagt                                              25

<210> SEQ ID NO 220
<211> LENGTH: 25
<212> TYPE: DNA

```
<213> ORGANISM: Homo sapiens

<400> SEQUENCE: 220
aaaagagcat gatcctgtag gtcaa                                        25

<210> SEQ ID NO 221
<211> LENGTH: 25
<212> TYPE: DNA
<213> ORGANISM: Homo sapiens

<400> SEQUENCE: 221
gcatttctag gacttttcta acata                                        25

<210> SEQ ID NO 222
<211> LENGTH: 25
<212> TYPE: DNA
<213> ORGANISM: Homo sapiens

<400> SEQUENCE: 222
ggattttacg agtctcttgc caagg                                        25

<210> SEQ ID NO 223
<211> LENGTH: 25
<212> TYPE: DNA
<213> ORGANISM: Homo sapiens

<400> SEQUENCE: 223
ccattgtgga ccacccacac tgaga                                        25

<210> SEQ ID NO 224
<211> LENGTH: 25
<212> TYPE: DNA
<213> ORGANISM: Homo sapiens

<400> SEQUENCE: 224
caggactttt gttccaggtt gccag                                        25

<210> SEQ ID NO 225
<211> LENGTH: 25
<212> TYPE: DNA
<213> ORGANISM: Homo sapiens

<400> SEQUENCE: 225
cccctagacg ttgccaacca gaact                                        25

<210> SEQ ID NO 226
<211> LENGTH: 25
<212> TYPE: DNA
<213> ORGANISM: Homo sapiens

<400> SEQUENCE: 226
gcatcatgta atctgggacc tgcca                                        25

<210> SEQ ID NO 227
<211> LENGTH: 25
<212> TYPE: DNA
<213> ORGANISM: Homo sapiens

<400> SEQUENCE: 227
tgatgagctt tcctttgatc cggac                                        25

<210> SEQ ID NO 228
<211> LENGTH: 25
```

```
<212> TYPE: DNA
<213> ORGANISM: Homo sapiens

<400> SEQUENCE: 228
gaacagtttg tacagacgta tgctt                                         25

<210> SEQ ID NO 229
<211> LENGTH: 25
<212> TYPE: DNA
<213> ORGANISM: Homo sapiens

<400> SEQUENCE: 229
tccatacccc ttcaaacatg ttgct                                         25

<210> SEQ ID NO 230
<211> LENGTH: 25
<212> TYPE: DNA
<213> ORGANISM: Homo sapiens

<400> SEQUENCE: 230
caaccacagg catcaggcaa ccatt                                         25

<210> SEQ ID NO 231
<211> LENGTH: 25
<212> TYPE: DNA
<213> ORGANISM: Homo sapiens

<400> SEQUENCE: 231
gaaagcagag tactatggtt gtcca                                         25

<210> SEQ ID NO 232
<211> LENGTH: 25
<212> TYPE: DNA
<213> ORGANISM: Homo sapiens

<400> SEQUENCE: 232
gcctttcaag cgacagatgc ctcat                                         25

<210> SEQ ID NO 233
<211> LENGTH: 25
<212> TYPE: DNA
<213> ORGANISM: Homo sapiens

<400> SEQUENCE: 233
gttctactca tatatatcta tctta                                         25

<210> SEQ ID NO 234
<211> LENGTH: 25
<212> TYPE: DNA
<213> ORGANISM: Homo sapiens

<400> SEQUENCE: 234
ggccaaagag ggtcgacctg caaac                                         25

<210> SEQ ID NO 235
<211> LENGTH: 25
<212> TYPE: DNA
<213> ORGANISM: Homo sapiens

<400> SEQUENCE: 235
gaagcttgtg cagagtggta accat                                         25

<210> SEQ ID NO 236
```

```
<211> LENGTH: 25
<212> TYPE: DNA
<213> ORGANISM: Homo sapiens

<400> SEQUENCE: 236
cacaatttcc aggggacctc aggtc                                            25

<210> SEQ ID NO 237
<211> LENGTH: 25
<212> TYPE: DNA
<213> ORGANISM: Homo sapiens

<400> SEQUENCE: 237
tgtggaaagc ctggatctca gctcc                                            25

<210> SEQ ID NO 238
<211> LENGTH: 25
<212> TYPE: DNA
<213> ORGANISM: Homo sapiens

<400> SEQUENCE: 238
ttgtcttttg gttgccatgg tcacc                                            25

<210> SEQ ID NO 239
<211> LENGTH: 25
<212> TYPE: DNA
<213> ORGANISM: Homo sapiens

<400> SEQUENCE: 239
gcgtttctgg agattacaac atcct                                            25

<210> SEQ ID NO 240
<211> LENGTH: 25
<212> TYPE: DNA
<213> ORGANISM: Homo sapiens

<400> SEQUENCE: 240
acagaattcc actgttctgc tcggt                                            25

<210> SEQ ID NO 241
<211> LENGTH: 25
<212> TYPE: DNA
<213> ORGANISM: Homo sapiens

<400> SEQUENCE: 241
tctaaataat gcccagtctt ctccc                                            25

<210> SEQ ID NO 242
<211> LENGTH: 25
<212> TYPE: DNA
<213> ORGANISM: Homo sapiens

<400> SEQUENCE: 242
cacaacactt atgtatgcac cccaa                                            25

<210> SEQ ID NO 243
<211> LENGTH: 25
<212> TYPE: DNA
<213> ORGANISM: Homo sapiens

<400> SEQUENCE: 243
aagtgtgcag aatactggcc gtcaa                                            25
```

```
<210> SEQ ID NO 244
<211> LENGTH: 25
<212> TYPE: DNA
<213> ORGANISM: Homo sapiens

<400> SEQUENCE: 244
gactgacctt gatgagctgt gcaca                                    25

<210> SEQ ID NO 245
<211> LENGTH: 25
<212> TYPE: DNA
<213> ORGANISM: Homo sapiens

<400> SEQUENCE: 245
gctgtccttt tgaggcttag tcagt                                    25

<210> SEQ ID NO 246
<211> LENGTH: 25
<212> TYPE: DNA
<213> ORGANISM: Homo sapiens

<400> SEQUENCE: 246
gactcatgtt tccctgtttc aaagg                                    25

<210> SEQ ID NO 247
<211> LENGTH: 25
<212> TYPE: DNA
<213> ORGANISM: Homo sapiens

<400> SEQUENCE: 247
ctgaccatcg ccatggaaac agcca                                    25

<210> SEQ ID NO 248
<211> LENGTH: 25
<212> TYPE: DNA
<213> ORGANISM: Homo sapiens

<400> SEQUENCE: 248
gactggacct gggaaaacgc atcct                                    25

<210> SEQ ID NO 249
<211> LENGTH: 25
<212> TYPE: DNA
<213> ORGANISM: Homo sapiens

<400> SEQUENCE: 249
cttcctaaac ccttgccata gtgga                                    25

<210> SEQ ID NO 250
<211> LENGTH: 25
<212> TYPE: DNA
<213> ORGANISM: Homo sapiens

<400> SEQUENCE: 250
tggcagatca tgatttccag cccac                                    25

<210> SEQ ID NO 251
<211> LENGTH: 25
<212> TYPE: DNA
<213> ORGANISM: Homo sapiens

<400> SEQUENCE: 251
atcaccagaa taaacccagc ttccc                                    25
```

-continued

```
<210> SEQ ID NO 252
<211> LENGTH: 25
<212> TYPE: DNA
<213> ORGANISM: Homo sapiens

<400> SEQUENCE: 252
accccttgcg aacaggacca gattt                                              25

<210> SEQ ID NO 253
<211> LENGTH: 25
<212> TYPE: DNA
<213> ORGANISM: Homo sapiens

<400> SEQUENCE: 253 aaacagggt tcttagtctc agcac                                               25

<210> SEQ ID NO 254
<211> LENGTH: 25
<212> TYPE: DNA
<213> ORGANISM: Homo sapiens

<400> SEQUENCE: 254
cagcctgcca taggatccaa ctgga                                              25

<210> SEQ ID NO 255
<211> LENGTH: 25
<212> TYPE: DNA
<213> ORGANISM: Homo sapiens

<400> SEQUENCE: 255
tcagacttgg ctcagctcgg ggagc                                              25

<210> SEQ ID NO 256
<211> LENGTH: 25
<212> TYPE: DNA
<213> ORGANISM: Homo sapiens

<400> SEQUENCE: 256
aatcaagcca ctcggcaggc atgga                                              25

<210> SEQ ID NO 257
<211> LENGTH: 25
<212> TYPE: DNA
<213> ORGANISM: Homo sapiens

<400> SEQUENCE: 257
gaacgttcta tgtatttcat cggat                                              25

<210> SEQ ID NO 258
<211> LENGTH: 25
<212> TYPE: DNA
<213> ORGANISM: Homo sapiens

<400> SEQUENCE: 258
aggacttgaa tcgtatcttc ccact                                              25

<210> SEQ ID NO 259
<211> LENGTH: 25
<212> TYPE: DNA
<213> ORGANISM: Homo sapiens

<400> SEQUENCE: 259
ataagcttat ctcagctgac tcctc                                              25
```

<210> SEQ ID NO 260
<211> LENGTH: 25
<212> TYPE: DNA
<213> ORGANISM: Homo sapiens

<400> SEQUENCE: 260
gaacccttgg atttatgtga ggtca                                    25

<210> SEQ ID NO 261
<211> LENGTH: 25
<212> TYPE: DNA
<213> ORGANISM: Homo sapiens

<400> SEQUENCE: 261 cccccccagcc aagaaagcta tctct                                   25

<210> SEQ ID NO 262
<211> LENGTH: 25
<212> TYPE: DNA
<213> ORGANISM: Homo sapiens

<400> SEQUENCE: 262
gtgtttttgt gaattgcttg gttgt                                    25

<210> SEQ ID NO 263
<211> LENGTH: 25
<212> TYPE: DNA
<213> ORGANISM: Homo sapiens

<400> SEQUENCE: 263
ttgtggctta tgggtattgc tgtct                                    25

<210> SEQ ID NO 264
<211> LENGTH: 25
<212> TYPE: DNA
<213> ORGANISM: Homo sapiens

<400> SEQUENCE: 264
tgcattatca tctccaagct gtcac                                    25

<210> SEQ ID NO 265
<211> LENGTH: 25
<212> TYPE: DNA
<213> ORGANISM: Homo sapiens

<400> SEQUENCE: 265
tgaaaaaggg tttctattct ctctg                                    25

<210> SEQ ID NO 266
<211> LENGTH: 25
<212> TYPE: DNA
<213> ORGANISM: Homo sapiens

<400> SEQUENCE: 266
gactctgcct cgtcagtgag attcc                                    25

<210> SEQ ID NO 267
<211> LENGTH: 25
<212> TYPE: DNA
<213> ORGANISM: Homo sapiens

<400> SEQUENCE: 267
gcaggacaat ctgcttgtgt ctccc                                              25

<210> SEQ ID NO 268
<211> LENGTH: 25
<212> TYPE: DNA
<213> ORGANISM: Homo sapiens

<400> SEQUENCE: 268
gagacagccc aggttcgtgg tttac                                              25

<210> SEQ ID NO 269
<211> LENGTH: 25
<212> TYPE: DNA
<213> ORGANISM: Homo sapiens

<400> SEQUENCE: 269
ttttcctgga tatctgtgta ttttc                                              25

<210> SEQ ID NO 270
<211> LENGTH: 25
<212> TYPE: DNA
<213> ORGANISM: Homo sapiens

<400> SEQUENCE: 270 cccccctccaa atagccatac ttagc                                             25

<210> SEQ ID NO 271
<211> LENGTH: 25
<212> TYPE: DNA
<213> ORGANISM: Homo sapiens

<400> SEQUENCE: 271
acattgaccc acaggacatt gtaaa                                              25

<210> SEQ ID NO 272
<211> LENGTH: 25
<212> TYPE: DNA
<213> ORGANISM: Homo sapiens

<400> SEQUENCE: 272
gacagtgcct cgaaagtcgg acctg                                              25

<210> SEQ ID NO 273
<211> LENGTH: 25
<212> TYPE: DNA
<213> ORGANISM: Homo sapiens

<400> SEQUENCE: 273
gtctctgcac ctacttttgc agaat                                              25

<210> SEQ ID NO 274
<211> LENGTH: 25
<212> TYPE: DNA
<213> ORGANISM: Homo sapiens

<400> SEQUENCE: 274
actgagccag cctttagat ctaca                                               25

<210> SEQ ID NO 275
<211> LENGTH: 25
<212> TYPE: DNA
<213> ORGANISM: Homo sapiens

<400> SEQUENCE: 275
gacagagagg cacctgggtc agtat                                              25

<210> SEQ ID NO 276
<211> LENGTH: 25
<212> TYPE: DNA
<213> ORGANISM: Homo sapiens

<400> SEQUENCE: 276
gtctgggttt gcagatgggt gccct                                              25

<210> SEQ ID NO 277
<211> LENGTH: 25
<212> TYPE: DNA
<213> ORGANISM: Homo sapiens

<400> SEQUENCE: 277
aaagagaacc atcagcaggc cagca                                              25

<210> SEQ ID NO 278
<211> LENGTH: 25
<212> TYPE: DNA
<213> ORGANISM: Homo sapiens

<400> SEQUENCE: 278
tgactccaga tactgcctga gcagc                                              25

<210> SEQ ID NO 279
<211> LENGTH: 25
<212> TYPE: DNA
<213> ORGANISM: Homo sapiens

<400> SEQUENCE: 279
gagctataca ttcttctttc tggtc                                              25

<210> SEQ ID NO 280
<211> LENGTH: 25
<212> TYPE: DNA
<213> ORGANISM: Homo sapiens

<400> SEQUENCE: 280
gaggtgtggt cagaggtgac ttgtt                                              25

<210> SEQ ID NO 281
<211> LENGTH: 25
<212> TYPE: DNA
<213> ORGANISM: Homo sapiens

<400> SEQUENCE: 281
ctgtcaagtc cagttctacg ggctc                                              25

<210> SEQ ID NO 282
<211> LENGTH: 25
<212> TYPE: DNA
<213> ORGANISM: Homo sapiens

<400> SEQUENCE: 282
agattggata cgcatcagac agatg                                              25

<210> SEQ ID NO 283
<211> LENGTH: 25
<212> TYPE: DNA
<213> ORGANISM: Homo sapiens

<400> SEQUENCE: 283
ccaatgctca cctattcagt tgctc                                          25

<210> SEQ ID NO 284
<211> LENGTH: 25
<212> TYPE: DNA
<213> ORGANISM: Homo sapiens

<400> SEQUENCE: 284
cctctatgct ttccttggag ccaaa                                          25

<210> SEQ ID NO 285
<211> LENGTH: 25
<212> TYPE: DNA
<213> ORGANISM: Homo sapiens

<400> SEQUENCE: 285
tcccagcacc tagtatgctc agtaa                                          25

<210> SEQ ID NO 286
<211> LENGTH: 25
<212> TYPE: DNA
<213> ORGANISM: Homo sapiens

<400> SEQUENCE: 286
tctagcttca ttgcttacca gaaaa                                          25

<210> SEQ ID NO 287
<211> LENGTH: 25
<212> TYPE: DNA
<213> ORGANISM: Homo sapiens

<400> SEQUENCE: 287
gtatgtctcg tggtaggact gtaga                                          25

<210> SEQ ID NO 288
<211> LENGTH: 25
<212> TYPE: DNA
<213> ORGANISM: Homo sapiens

<400> SEQUENCE: 288
cccgtgtgga cacagatccc actgg                                          25

<210> SEQ ID NO 289
<211> LENGTH: 25
<212> TYPE: DNA
<213> ORGANISM: Homo sapiens

<400> SEQUENCE: 289
catttggcat tcacatgtgg ctgtt                                          25

<210> SEQ ID NO 290
<211> LENGTH: 25
<212> TYPE: DNA
<213> ORGANISM: Homo sapiens

<400> SEQUENCE: 290
ttgagttctc cttttaagta ccaat                                          25

<210> SEQ ID NO 291
<211> LENGTH: 25
<212> TYPE: DNA
<213> ORGANISM: Homo sapiens

```
<400> SEQUENCE: 291
catttcccta ccaaagctgt gtatt                                              25

<210> SEQ ID NO 292
<211> LENGTH: 25
<212> TYPE: DNA
<213> ORGANISM: Homo sapiens

<400> SEQUENCE: 292
ccttctacaa tcgagcagct ccttg                                              25

<210> SEQ ID NO 293
<211> LENGTH: 25
<212> TYPE: DNA
<213> ORGANISM: Homo sapiens

<400> SEQUENCE: 293
gtgcaccaga gcacgcacag gagcc                                              25

<210> SEQ ID NO 294
<211> LENGTH: 25
<212> TYPE: DNA
<213> ORGANISM: Homo sapiens

<400> SEQUENCE: 294
gtgtgtaccc cgtaagcatg aaacc                                              25

<210> SEQ ID NO 295
<211> LENGTH: 25
<212> TYPE: DNA
<213> ORGANISM: Homo sapiens

<400> SEQUENCE: 295
aatagatttg tttgactgct tgtgt                                              25

<210> SEQ ID NO 296
<211> LENGTH: 25
<212> TYPE: DNA
<213> ORGANISM: Homo sapiens

<400> SEQUENCE: 296
acagccaatt tctaagcaga cagga                                              25

<210> SEQ ID NO 297
<211> LENGTH: 25
<212> TYPE: DNA
<213> ORGANISM: Homo sapiens

<400> SEQUENCE: 297
accccacatt catatcccta aattt                                              25

<210> SEQ ID NO 298
<211> LENGTH: 25
<212> TYPE: DNA
<213> ORGANISM: Homo sapiens

<400> SEQUENCE: 298
gaatgacaag ctgtaccttta aacca                                             25

<210> SEQ ID NO 299
<211> LENGTH: 25
<212> TYPE: DNA
```

```
<213> ORGANISM: Homo sapiens

<400> SEQUENCE: 299
tgaggcgccg gtcatatcag aatat                                  25

<210> SEQ ID NO 300
<211> LENGTH: 25
<212> TYPE: DNA
<213> ORGANISM: Homo sapiens

<400> SEQUENCE: 300
gtaactgcac tcaagctgtg ctcaa                                  25

<210> SEQ ID NO 301
<211> LENGTH: 25
<212> TYPE: DNA
<213> ORGANISM: Homo sapiens

<400> SEQUENCE: 301
gttgactgtc tacagccact gttaa                                  25

<210> SEQ ID NO 302
<211> LENGTH: 25
<212> TYPE: DNA
<213> ORGANISM: Homo sapiens

<400> SEQUENCE: 302
gtagtctgtt ggttcagtgc atgct                                  25

<210> SEQ ID NO 303
<211> LENGTH: 25
<212> TYPE: DNA
<213> ORGANISM: Homo sapiens

<400> SEQUENCE: 303
gggggacctt agcatgccta agtga                                  25

<210> SEQ ID NO 304
<211> LENGTH: 25
<212> TYPE: DNA
<213> ORGANISM: Homo sapiens

<400> SEQUENCE: 304
gatggctctg tgaagctggt gaccc                                  25

<210> SEQ ID NO 305
<211> LENGTH: 25
<212> TYPE: DNA
<213> ORGANISM: Homo sapiens

<400> SEQUENCE: 305
tgtgagtgac agttacccca tttca                                  25

<210> SEQ ID NO 306
<211> LENGTH: 25
<212> TYPE: DNA
<213> ORGANISM: Homo sapiens

<400> SEQUENCE: 306
gcttaagctt gaattagatc cctgc                                  25

<210> SEQ ID NO 307
<211> LENGTH: 25
```

```
<212> TYPE: DNA
<213> ORGANISM: Homo sapiens

<400> SEQUENCE: 307
atggggttca ttggacacta tcttg                                      25

<210> SEQ ID NO 308
<211> LENGTH: 25
<212> TYPE: DNA
<213> ORGANISM: Homo sapiens

<400> SEQUENCE: 308
tttcctgctt tggctacata tccat                                      25

<210> SEQ ID NO 309
<211> LENGTH: 25
<212> TYPE: DNA
<213> ORGANISM: Homo sapiens

<400> SEQUENCE: 309
agctgtccaa catgatcgtg cgctc                                      25

<210> SEQ ID NO 310
<211> LENGTH: 25
<212> TYPE: DNA
<213> ORGANISM: Homo sapiens

<400> SEQUENCE: 310
tacaacacta tacatacaca ccacc                                      25

<210> SEQ ID NO 311
<211> LENGTH: 25
<212> TYPE: DNA
<213> ORGANISM: Homo sapiens

<400> SEQUENCE: 311
tggaaagata cctggccgca tgact                                      25

<210> SEQ ID NO 312
<211> LENGTH: 25
<212> TYPE: DNA
<213> ORGANISM: Homo sapiens

<400> SEQUENCE: 312
gagacacgcc cagtggatga tccta                                      25

<210> SEQ ID NO 313
<211> LENGTH: 25
<212> TYPE: DNA
<213> ORGANISM: Homo sapiens

<400> SEQUENCE: 313
tctgctgctt tgtttcttct aagta                                      25

<210> SEQ ID NO 314
<211> LENGTH: 25
<212> TYPE: DNA
<213> ORGANISM: Homo sapiens

<400> SEQUENCE: 314
gtacatattt tggttcttct atctc                                      25

<210> SEQ ID NO 315
```

```
<211> LENGTH: 25
<212> TYPE: DNA
<213> ORGANISM: Homo sapiens

<400> SEQUENCE: 315
gtaccccgag ctgcggtgtt tgaag                                              25

<210> SEQ ID NO 316
<211> LENGTH: 25
<212> TYPE: DNA
<213> ORGANISM: Homo sapiens

<400> SEQUENCE: 316
cctttgtgct tgcagaaagt ttgcc                                              25

<210> SEQ ID NO 317
<211> LENGTH: 25
<212> TYPE: DNA
<213> ORGANISM: Homo sapiens

<400> SEQUENCE: 317
gattcctgaa ctcaaggtac cagca                                              25

<210> SEQ ID NO 318
<211> LENGTH: 25
<212> TYPE: DNA
<213> ORGANISM: Homo sapiens

<400> SEQUENCE: 318
aagggacgtg ggacagttcg tactg                                              25

<210> SEQ ID NO 319
<211> LENGTH: 25
<212> TYPE: DNA
<213> ORGANISM: Homo sapiens

<400> SEQUENCE: 319
gtagaagtgt ccaaacaggt tgtgt                                              25

<210> SEQ ID NO 320
<211> LENGTH: 25
<212> TYPE: DNA
<213> ORGANISM: Homo sapiens

<400> SEQUENCE: 320
gaaatcgtca gcattttcgt ccttg                                              25

<210> SEQ ID NO 321
<211> LENGTH: 25
<212> TYPE: DNA
<213> ORGANISM: Homo sapiens

<400> SEQUENCE: 321
gacaccttcg cttgttatct tgtca                                              25

<210> SEQ ID NO 322
<211> LENGTH: 25
<212> TYPE: DNA
<213> ORGANISM: Homo sapiens

<400> SEQUENCE: 322
acaggatgca atcttttgtt gtcta                                              25
```

```
<210> SEQ ID NO 323
<211> LENGTH: 25
<212> TYPE: DNA
<213> ORGANISM: Homo sapiens

<400> SEQUENCE: 323
gtggttggat caaggactca ttcct                                   25

<210> SEQ ID NO 324
<211> LENGTH: 25
<212> TYPE: DNA
<213> ORGANISM: Homo sapiens

<400> SEQUENCE: 324
caataacaga aagtccttcc gcctt                                   25

<210> SEQ ID NO 325
<211> LENGTH: 25
<212> TYPE: DNA
<213> ORGANISM: Homo sapiens

<400> SEQUENCE: 325
attggcattg cttgtttttt gaaac                                   25

<210> SEQ ID NO 326
<211> LENGTH: 25
<212> TYPE: DNA
<213> ORGANISM: Homo sapiens

<400> SEQUENCE: 326
gctacccata ttgcactgag cttgc                                   25

<210> SEQ ID NO 327
<211> LENGTH: 25
<212> TYPE: DNA
<213> ORGANISM: Homo sapiens

<400> SEQUENCE: 327
ggcatatgtt tctgctagct atata                                   25

<210> SEQ ID NO 328
<211> LENGTH: 25
<212> TYPE: DNA
<213> ORGANISM: Homo sapiens

<400> SEQUENCE: 328
tcatattgcg aaagccttgg ccctt                                   25

<210> SEQ ID NO 329
<211> LENGTH: 25
<212> TYPE: DNA
<213> ORGANISM: Homo sapiens

<400> SEQUENCE: 329
aatatattct ttactgcctt gtgga                                   25

<210> SEQ ID NO 330
<211> LENGTH: 25
<212> TYPE: DNA
<213> ORGANISM: Homo sapiens

<400> SEQUENCE: 330
accgaaactg gcatcttact cttgg                                   25
```

<210> SEQ ID NO 331
<211> LENGTH: 25
<212> TYPE: DNA
<213> ORGANISM: Homo sapiens

<400> SEQUENCE: 331
caaatgttct gttttggctg ctatt                                              25

<210> SEQ ID NO 332
<211> LENGTH: 25
<212> TYPE: DNA
<213> ORGANISM: Homo sapiens

<400> SEQUENCE: 332
acaatgttga gttcagcatg tgtct                                              25

<210> SEQ ID NO 333
<211> LENGTH: 25
<212> TYPE: DNA
<213> ORGANISM: Homo sapiens

<400> SEQUENCE: 333
atgggtggtt taccatttct tgagg                                              25

<210> SEQ ID NO 334
<211> LENGTH: 25
<212> TYPE: DNA
<213> ORGANISM: Homo sapiens

<400> SEQUENCE: 334
caaccattgg tctgcaggac atcac                                              25

<210> SEQ ID NO 335
<211> LENGTH: 25
<212> TYPE: DNA
<213> ORGANISM: Homo sapiens

<400> SEQUENCE: 335
gccagatggt tgctgccaca acttg                                              25

<210> SEQ ID NO 336
<211> LENGTH: 25
<212> TYPE: DNA
<213> ORGANISM: Homo sapiens

<400> SEQUENCE: 336
ggtaatgagc catggccatt gtccc                                              25

<210> SEQ ID NO 337
<211> LENGTH: 25
<212> TYPE: DNA
<213> ORGANISM: Homo sapiens

<400> SEQUENCE: 337
gtccctgtaa ctcaaatgtc aaccc                                              25

<210> SEQ ID NO 338
<211> LENGTH: 25
<212> TYPE: DNA
<213> ORGANISM: Homo sapiens

<400> SEQUENCE: 338
gcaacctcac aaccttggct gagtc                                              25

```
<210> SEQ ID NO 339
<211> LENGTH: 25
<212> TYPE: DNA
<213> ORGANISM: Homo sapiens

<400> SEQUENCE: 339
atccttgctg cagacttcga aattg                                          25

<210> SEQ ID NO 340
<211> LENGTH: 25
<212> TYPE: DNA
<213> ORGANISM: Homo sapiens

<400> SEQUENCE: 340
aatcgaagct tagcagctcc tcgtg                                          25

<210> SEQ ID NO 341
<211> LENGTH: 25
<212> TYPE: DNA
<213> ORGANISM: Homo sapiens

<400> SEQUENCE: 341
ctaccctaga catctgcatc tttgt                                          25

<210> SEQ ID NO 342
<211> LENGTH: 25
<212> TYPE: DNA
<213> ORGANISM: Homo sapiens

<400> SEQUENCE: 342
cccccatgtg acttttatct gtagc                                          25

<210> SEQ ID NO 343
<211> LENGTH: 25
<212> TYPE: DNA
<213> ORGANISM: Homo sapiens

<400> SEQUENCE: 343
gatgtcatct gtcactatag gtcat                                          25

<210> SEQ ID NO 344
<211> LENGTH: 25
<212> TYPE: DNA
<213> ORGANISM: Homo sapiens

<400> SEQUENCE: 344
gtatcagtgc ctgcctgagt tagga                                          25

<210> SEQ ID NO 345
<211> LENGTH: 25
<212> TYPE: DNA
<213> ORGANISM: Homo sapiens

<400> SEQUENCE: 345
ccagcaaccc aggagcctag tacaa                                          25

<210> SEQ ID NO 346
<211> LENGTH: 25
<212> TYPE: DNA
<213> ORGANISM: Homo sapiens

<400> SEQUENCE: 346
```
acgcaagagt acttactgtc ttccc                                              25

<210> SEQ ID NO 347
<211> LENGTH: 25
<212> TYPE: DNA
<213> ORGANISM: Homo sapiens

<400> SEQUENCE: 347
aactgctccc actgtggcaa gagct                                              25

<210> SEQ ID NO 348
<211> LENGTH: 25
<212> TYPE: DNA
<213> ORGANISM: Homo sapiens

<400> SEQUENCE: 348
acagggctgt ttaagtcact gactt                                              25

<210> SEQ ID NO 349
<211> LENGTH: 25
<212> TYPE: DNA
<213> ORGANISM: Homo sapiens

<400> SEQUENCE: 349
taaaacccag tgacctcact tcttt                                              25

<210> SEQ ID NO 350
<211> LENGTH: 25
<212> TYPE: DNA
<213> ORGANISM: Homo sapiens

<400> SEQUENCE: 350
aaggaatatc ctggagtggt cccca                                              25

<210> SEQ ID NO 351
<211> LENGTH: 25
<212> TYPE: DNA
<213> ORGANISM: Homo sapiens

<400> SEQUENCE: 351
ccctcttgca tctggaacgc caggt                                              25

<210> SEQ ID NO 352
<211> LENGTH: 25
<212> TYPE: DNA
<213> ORGANISM: Homo sapiens

<400> SEQUENCE: 352
ggactctgat gttactcttg agctt                                              25

<210> SEQ ID NO 353
<211> LENGTH: 25
<212> TYPE: DNA
<213> ORGANISM: Homo sapiens

<400> SEQUENCE: 353
gtctcactac aagcagccta tctgc                                              25

<210> SEQ ID NO 354
<211> LENGTH: 25
<212> TYPE: DNA
<213> ORGANISM: Homo sapiens

<400> SEQUENCE: 354
actctggagg ccctcttgtg tgtaa                                                  25

<210> SEQ ID NO 355
<211> LENGTH: 25
<212> TYPE: DNA
<213> ORGANISM: Homo sapiens

<400> SEQUENCE: 355
agagtagggt cgccatgatg cagcc                                                  25

<210> SEQ ID NO 356
<211> LENGTH: 25
<212> TYPE: DNA
<213> ORGANISM: Homo sapiens

<400> SEQUENCE: 356
gctgctatgg tcttagcctg tagac                                                  25

<210> SEQ ID NO 357
<211> LENGTH: 25
<212> TYPE: DNA
<213> ORGANISM: Homo sapiens

<400> SEQUENCE: 357
tctgtcattt acacacgtcg ttcta                                                  25

<210> SEQ ID NO 358
<211> LENGTH: 25
<212> TYPE: DNA
<213> ORGANISM: Homo sapiens

<400> SEQUENCE: 358
tttcgcctta aactctggac actct                                                  25

<210> SEQ ID NO 359
<211> LENGTH: 25
<212> TYPE: DNA
<213> ORGANISM: Homo sapiens

<400> SEQUENCE: 359
caatgcccga gagcgtctgc gggtc                                                  25

<210> SEQ ID NO 360
<211> LENGTH: 25
<212> TYPE: DNA
<213> ORGANISM: Homo sapiens

<400> SEQUENCE: 360
aacctgagag acagctctac ccttc                                                  25

<210> SEQ ID NO 361
<211> LENGTH: 25
<212> TYPE: DNA
<213> ORGANISM: Homo sapiens

<400> SEQUENCE: 361
agcgcagcgc aaaggtctca atgcc                                                  25

<210> SEQ ID NO 362
<211> LENGTH: 25
<212> TYPE: DNA
<213> ORGANISM: Homo sapiens

```
<400> SEQUENCE: 362
gtggttgctg tcatatttgc tctag                                              25

<210> SEQ ID NO 363
<211> LENGTH: 25
<212> TYPE: DNA
<213> ORGANISM: Homo sapiens

<400> SEQUENCE: 363
gatgatttta ctcagcttat ccaaa                                              25

<210> SEQ ID NO 364
<211> LENGTH: 25
<212> TYPE: DNA
<213> ORGANISM: Homo sapiens

<400> SEQUENCE: 364
ttttacattt attccttcca agaag                                              25

<210> SEQ ID NO 365
<211> LENGTH: 25
<212> TYPE: DNA
<213> ORGANISM: Homo sapiens

<400> SEQUENCE: 365
gaagtcctca gctagaagta cacaa                                              25

<210> SEQ ID NO 366
<211> LENGTH: 25
<212> TYPE: DNA
<213> ORGANISM: Homo sapiens

<400> SEQUENCE: 366
attcaggaca agctgcaact tcccc                                              25

<210> SEQ ID NO 367
<211> LENGTH: 25
<212> TYPE: DNA
<213> ORGANISM: Homo sapiens

<400> SEQUENCE: 367
aggtcatgca cgaagggagc accgt                                              25

<210> SEQ ID NO 368
<211> LENGTH: 25
<212> TYPE: DNA
<213> ORGANISM: Homo sapiens

<400> SEQUENCE: 368
ttggggcctc aaatttgact ctgcc                                              25

<210> SEQ ID NO 369
<211> LENGTH: 25
<212> TYPE: DNA
<213> ORGANISM: Homo sapiens

<400> SEQUENCE: 369
aatgtgattt tcctaggcta ctgca                                              25

<210> SEQ ID NO 370
<211> LENGTH: 25
<212> TYPE: DNA
<213> ORGANISM: Homo sapiens
```

```
<400> SEQUENCE: 370
ttgtactttt tgttccagag ctgct                                          25

<210> SEQ ID NO 371
<211> LENGTH: 25
<212> TYPE: DNA
<213> ORGANISM: Homo sapiens

<400> SEQUENCE: 371
aaatcactaa acctcgtttt ctcag                                          25

<210> SEQ ID NO 372
<211> LENGTH: 25
<212> TYPE: DNA
<213> ORGANISM: Homo sapiens

<400> SEQUENCE: 372
atatccctta ctccagaggg ccttc                                          25

<210> SEQ ID NO 373
<211> LENGTH: 25
<212> TYPE: DNA
<213> ORGANISM: Homo sapiens

<400> SEQUENCE: 373
gcggacgaga gaaatcgcgg cccac                                          25

<210> SEQ ID NO 374
<211> LENGTH: 25
<212> TYPE: DNA
<213> ORGANISM: Homo sapiens

<400> SEQUENCE: 374
tatgctactg ggacagactg ttgca                                          25

<210> SEQ ID NO 375
<211> LENGTH: 25
<212> TYPE: DNA
<213> ORGANISM: Homo sapiens

<400> SEQUENCE: 375
aaagaccaac aaatctcaag cccta                                          25

<210> SEQ ID NO 376
<211> LENGTH: 25
<212> TYPE: DNA
<213> ORGANISM: Homo sapiens

<400> SEQUENCE: 376
gagttctcct tttaagtacc aatga                                          25

<210> SEQ ID NO 377
<211> LENGTH: 25
<212> TYPE: DNA
<213> ORGANISM: Homo sapiens

<400> SEQUENCE: 377
aacgtttata tcctgtgatt actct                                          25

<210> SEQ ID NO 378
<211> LENGTH: 25
<212> TYPE: DNA
```

<213> ORGANISM: Homo sapiens

<400> SEQUENCE: 378
gttctcgtct gcatttgtgg accag                                              25

<210> SEQ ID NO 379
<211> LENGTH: 25
<212> TYPE: DNA
<213> ORGANISM: Homo sapiens

<400> SEQUENCE: 379
gcatgatcat gcttgtctag aacac                                              25

<210> SEQ ID NO 380
<211> LENGTH: 25
<212> TYPE: DNA
<213> ORGANISM: Homo sapiens

<400> SEQUENCE: 380
tagagcatgc tgtgaacttc gaaga                                              25

<210> SEQ ID NO 381
<211> LENGTH: 25
<212> TYPE: DNA
<213> ORGANISM: Homo sapiens

<400> SEQUENCE: 381
ggtagggatg gccatggtgc cagcc                                              25

<210> SEQ ID NO 382
<211> LENGTH: 25
<212> TYPE: DNA
<213> ORGANISM: Homo sapiens

<400> SEQUENCE: 382
ttctgtggat ccagtatctt cctcg                                              25

<210> SEQ ID NO 383
<211> LENGTH: 25
<212> TYPE: DNA
<213> ORGANISM: Homo sapiens

<400> SEQUENCE: 383
gtatctgaag acctaccagg gacaa                                              25

<210> SEQ ID NO 384
<211> LENGTH: 25
<212> TYPE: DNA
<213> ORGANISM: Homo sapiens

<400> SEQUENCE: 384
gccaacaagc gctttgtttt ccacc                                              25

<210> SEQ ID NO 385
<211> LENGTH: 25
<212> TYPE: DNA
<213> ORGANISM: Homo sapiens

<400> SEQUENCE: 385
aatcatattg gtattctagt tggca                                              25

<210> SEQ ID NO 386
<211> LENGTH: 25

-continued

<212> TYPE: DNA
<213> ORGANISM: Homo sapiens

<400> SEQUENCE: 386
gaagtcctca gctagaagta cacaa                                              25

<210> SEQ ID NO 387
<211> LENGTH: 25
<212> TYPE: DNA
<213> ORGANISM: Homo sapiens

<400> SEQUENCE: 387
gttatacaaa ccacagatga cacaa                                              25

<210> SEQ ID NO 388
<211> LENGTH: 25
<212> TYPE: DNA
<213> ORGANISM: Homo sapiens

<400> SEQUENCE: 388
cagtaaccac atgcggctgt ttaaa                                              25

<210> SEQ ID NO 389
<211> LENGTH: 25
<212> TYPE: DNA
<213> ORGANISM: Homo sapiens

<400> SEQUENCE: 389
aaactgtttg cctgtggtag acacc                                              25

<210> SEQ ID NO 390
<211> LENGTH: 25
<212> TYPE: DNA
<213> ORGANISM: Homo sapiens

<400> SEQUENCE: 390
gggagatacc gaagcctact gtggt                                              25

<210> SEQ ID NO 391
<211> LENGTH: 25
<212> TYPE: DNA
<213> ORGANISM: Homo sapiens

<400> SEQUENCE: 391
gggctcccaa agcgacaaga tcgtt                                              25

<210> SEQ ID NO 392
<211> LENGTH: 25
<212> TYPE: DNA
<213> ORGANISM: Homo sapiens

<400> SEQUENCE: 392
gtttgcctgt ggtagacacc tgcac                                              25

<210> SEQ ID NO 393
<211> LENGTH: 25
<212> TYPE: DNA
<213> ORGANISM: Homo sapiens

<400> SEQUENCE: 393
gacgacactg aggatccctg tgtgg                                              25

<210> SEQ ID NO 394

```
<211> LENGTH: 25
<212> TYPE: DNA
<213> ORGANISM: Homo sapiens

<400> SEQUENCE: 394
agtactggtt gaacctgacc acttc                                    25

<210> SEQ ID NO 395
<211> LENGTH: 25
<212> TYPE: DNA
<213> ORGANISM: Homo sapiens

<400> SEQUENCE: 395
gaaatcgccg tgttactgtt gcact                                    25

<210> SEQ ID NO 396
<211> LENGTH: 25
<212> TYPE: DNA
<213> ORGANISM: Homo sapiens

<400> SEQUENCE: 396
actgggccta tgtagtagcc tcatt                                    25

<210> SEQ ID NO 397
<211> LENGTH: 25
<212> TYPE: DNA
<213> ORGANISM: Homo sapiens

<400> SEQUENCE: 397
tatacttctg cctaacaaca tggaa                                    25

<210> SEQ ID NO 398
<211> LENGTH: 25
<212> TYPE: DNA
<213> ORGANISM: Homo sapiens

<400> SEQUENCE: 398
gcatacgttt ctttacagca gagga                                    25

<210> SEQ ID NO 399
<211> LENGTH: 25
<212> TYPE: DNA
<213> ORGANISM: Homo sapiens

<400> SEQUENCE: 399
gtgttgattt tatttgaccc ctgga                                    25

<210> SEQ ID NO 400
<211> LENGTH: 25
<212> TYPE: DNA
<213> ORGANISM: Homo sapiens

<400> SEQUENCE: 400
caatgttcct gatgatgtac cccac                                    25

<210> SEQ ID NO 401
<211> LENGTH: 25
<212> TYPE: DNA
<213> ORGANISM: Homo sapiens

<400> SEQUENCE: 401
gtgtgcatta aatatgcttc cacag                                    25
```

```
<210> SEQ ID NO 402
<211> LENGTH: 25
<212> TYPE: DNA
<213> ORGANISM: Homo sapiens

<400> SEQUENCE: 402 cttttttgtgt gcaaccactt accct                                  25

<210> SEQ ID NO 403
<211> LENGTH: 25
<212> TYPE: DNA
<213> ORGANISM: Homo sapiens

<400> SEQUENCE: 403
ggtttggacc acatctcttt ggaaa                                   25

<210> SEQ ID NO 404
<211> LENGTH: 25
<212> TYPE: DNA
<213> ORGANISM: Homo sapiens

<400> SEQUENCE: 404
ggcatcaagt acttcctgac gatgg                                   25

<210> SEQ ID NO 405
<211> LENGTH: 25
<212> TYPE: DNA
<213> ORGANISM: Homo sapiens

<400> SEQUENCE: 405
aaggatgctt gtacataatg cgtgc                                   25

<210> SEQ ID NO 406
<211> LENGTH: 25
<212> TYPE: DNA
<213> ORGANISM: Homo sapiens

<400> SEQUENCE: 406
tcaacacgtc tgtggaggtg ctgcc                                   25

<210> SEQ ID NO 407
<211> LENGTH: 25
<212> TYPE: DNA
<213> ORGANISM: Homo sapiens

<400> SEQUENCE: 407
agaacttggc cctgagtcgg gaaag                                   25

<210> SEQ ID NO 408
<211> LENGTH: 25
<212> TYPE: DNA
<213> ORGANISM: Homo sapiens

<400> SEQUENCE: 408
ccacagcttc ccccatagaa ggatt                                   25

<210> SEQ ID NO 409
<211> LENGTH: 25
<212> TYPE: DNA
<213> ORGANISM: Homo sapiens

<400> SEQUENCE: 409
tctggactaa ccctgtggtt gcctg                                   25
```

<210> SEQ ID NO 410
<211> LENGTH: 25
<212> TYPE: DNA
<213> ORGANISM: Homo sapiens

<400> SEQUENCE: 410
gaaaccttcc caatagagta caaca                                              25

<210> SEQ ID NO 411
<211> LENGTH: 25
<212> TYPE: DNA
<213> ORGANISM: Homo sapiens

<400> SEQUENCE: 411
aaccaggaag gccaacagct cagga                                              25

<210> SEQ ID NO 412
<211> LENGTH: 25
<212> TYPE: DNA
<213> ORGANISM: Homo sapiens

<400> SEQUENCE: 412
cctcattgag ttcggtgcat ctggc                                              25

<210> SEQ ID NO 413
<211> LENGTH: 25
<212> TYPE: DNA
<213> ORGANISM: Homo sapiens

<400> SEQUENCE: 413
gtaaggtctt tgtaaaatct tgcag                                              25

<210> SEQ ID NO 414
<211> LENGTH: 25
<212> TYPE: DNA
<213> ORGANISM: Homo sapiens

<400> SEQUENCE: 414
aatcaagttc ttgaccctat tcggc                                              25

<210> SEQ ID NO 415
<211> LENGTH: 25
<212> TYPE: DNA
<213> ORGANISM: Homo sapiens

<400> SEQUENCE: 415
ggtcctgttg acttgtatga tatcc                                              25

<210> SEQ ID NO 416
<211> LENGTH: 25
<212> TYPE: DNA
<213> ORGANISM: Homo sapiens

<400> SEQUENCE: 416
ctgatcagaa tcatggtctc ccgca                                              25

<210> SEQ ID NO 417
<211> LENGTH: 25
<212> TYPE: DNA
<213> ORGANISM: Homo sapiens

<400> SEQUENCE: 417 cccccttttcc tacagcaata tgttc                                             25

```
<210> SEQ ID NO 418
<211> LENGTH: 25
<212> TYPE: DNA
<213> ORGANISM: Homo sapiens

<400> SEQUENCE: 418
cgtggccatc cctgtgaggg tgacg                                              25

<210> SEQ ID NO 419
<211> LENGTH: 25
<212> TYPE: DNA
<213> ORGANISM: Homo sapiens

<400> SEQUENCE: 419
ctgccctgca cgtcatggga ggggg                                              25

<210> SEQ ID NO 420
<211> LENGTH: 25
<212> TYPE: DNA
<213> ORGANISM: Homo sapiens

<400> SEQUENCE: 420
accagcttgc gaataacagt ccccg                                              25

<210> SEQ ID NO 421
<211> LENGTH: 25
<212> TYPE: DNA
<213> ORGANISM: Homo sapiens

<400> SEQUENCE: 421
cgggaagggc gtgggttgag gagag                                              25

<210> SEQ ID NO 422
<211> LENGTH: 25
<212> TYPE: DNA
<213> ORGANISM: Homo sapiens

<400> SEQUENCE: 422
gcagttcatt attttgtggt tctat                                              25

<210> SEQ ID NO 423
<211> LENGTH: 25
<212> TYPE: DNA
<213> ORGANISM: Homo sapiens

<400> SEQUENCE: 423
gtaacgtgat tgattcagta tctta                                              25

<210> SEQ ID NO 424
<211> LENGTH: 25
<212> TYPE: DNA
<213> ORGANISM: Homo sapiens

<400> SEQUENCE: 424
ggatttatat agtgtgctcc cacta                                              25

<210> SEQ ID NO 425
<211> LENGTH: 25
<212> TYPE: DNA
<213> ORGANISM: Homo sapiens

<400> SEQUENCE: 425
```
aagaccatta gaaagcacca ggccg                                       25

<210> SEQ ID NO 426
<211> LENGTH: 25
<212> TYPE: DNA
<213> ORGANISM: Homo sapiens

<400> SEQUENCE: 426
gggtttcaca gtgcaatctc tgccc                                       25

<210> SEQ ID NO 427
<211> LENGTH: 25
<212> TYPE: DNA
<213> ORGANISM: Homo sapiens

<400> SEQUENCE: 427
gaattgcttt tgtcgaggtt ttggg                                       25

<210> SEQ ID NO 428
<211> LENGTH: 25
<212> TYPE: DNA
<213> ORGANISM: Homo sapiens

<400> SEQUENCE: 428
gtttggctgt tcatgtagtc acggt                                       25

<210> SEQ ID NO 429
<211> LENGTH: 25
<212> TYPE: DNA
<213> ORGANISM: Homo sapiens

<400> SEQUENCE: 429
gcacacacag agactttgc tccga                                        25

<210> SEQ ID NO 430
<211> LENGTH: 25
<212> TYPE: DNA
<213> ORGANISM: Homo sapiens

<400> SEQUENCE: 430
aggtgagaag tgctcccaag cagac                                       25

<210> SEQ ID NO 431
<211> LENGTH: 25
<212> TYPE: DNA
<213> ORGANISM: Homo sapiens

<400> SEQUENCE: 431
agcacaagct tatgcttccc gtagc                                       25

<210> SEQ ID NO 432
<211> LENGTH: 25
<212> TYPE: DNA
<213> ORGANISM: Homo sapiens

<400> SEQUENCE: 432
ggcaccgaag tcagatgagt atccc                                       25

<210> SEQ ID NO 433
<211> LENGTH: 25
<212> TYPE: DNA
<213> ORGANISM: Homo sapiens

<400> SEQUENCE: 433
tacacacagt ttttccgact tttca                                    25

<210> SEQ ID NO 434
<211> LENGTH: 25
<212> TYPE: DNA
<213> ORGANISM: Homo sapiens

<400> SEQUENCE: 434
aatggtactt gtcctagcgt tttgg                                    25

<210> SEQ ID NO 435
<211> LENGTH: 25
<212> TYPE: DNA
<213> ORGANISM: Homo sapiens

<400> SEQUENCE: 435
tggttcacca gccggactga agaat                                    25

<210> SEQ ID NO 436
<211> LENGTH: 25
<212> TYPE: DNA
<213> ORGANISM: Homo sapiens

<400> SEQUENCE: 436
acactctcct aagaggttct ctcca                                    25

<210> SEQ ID NO 437
<211> LENGTH: 25
<212> TYPE: DNA
<213> ORGANISM: Homo sapiens

<400> SEQUENCE: 437
aacttccccc aaatctgatg gacct                                    25

<210> SEQ ID NO 438
<211> LENGTH: 25
<212> TYPE: DNA
<213> ORGANISM: Homo sapiens

<400> SEQUENCE: 438
ctgatcagct gtacgactcc atgaa                                    25

<210> SEQ ID NO 439
<211> LENGTH: 25
<212> TYPE: DNA
<213> ORGANISM: Homo sapiens

<400> SEQUENCE: 439
agctcaaaac ttgctaggca tcaga                                    25

<210> SEQ ID NO 440
<211> LENGTH: 25
<212> TYPE: DNA
<213> ORGANISM: Homo sapiens

<400> SEQUENCE: 440
gccagcgctt ctggtctggt aaata                                    25

<210> SEQ ID NO 441
<211> LENGTH: 25
<212> TYPE: DNA
<213> ORGANISM: Homo sapiens

```
<400> SEQUENCE: 441
gatttaccag gctttctgaa agatc                                              25

<210> SEQ ID NO 442
<211> LENGTH: 25
<212> TYPE: DNA
<213> ORGANISM: Homo sapiens

<400> SEQUENCE: 442
atccatcctt ccaacatata tttat                                              25

<210> SEQ ID NO 443
<211> LENGTH: 25
<212> TYPE: DNA
<213> ORGANISM: Homo sapiens

<400> SEQUENCE: 443
attcccagaa tagttttcaa tgtat                                              25

<210> SEQ ID NO 444
<211> LENGTH: 25
<212> TYPE: DNA
<213> ORGANISM: Homo sapiens

<400> SEQUENCE: 444
ttgttgttac tcacttaaga ctgga                                              25

<210> SEQ ID NO 445
<211> LENGTH: 25
<212> TYPE: DNA
<213> ORGANISM: Homo sapiens

<400> SEQUENCE: 445
aaattcctgg ggctgatact tctct                                              25

<210> SEQ ID NO 446
<211> LENGTH: 25
<212> TYPE: DNA
<213> ORGANISM: Homo sapiens

<400> SEQUENCE: 446
accccaacca gccgacgaga ttcgg                                              25

<210> SEQ ID NO 447
<211> LENGTH: 25
<212> TYPE: DNA
<213> ORGANISM: Homo sapiens

<400> SEQUENCE: 447
gactgagcgg tgcattgagt ccctg                                              25

<210> SEQ ID NO 448
<211> LENGTH: 25
<212> TYPE: DNA
<213> ORGANISM: Homo sapiens

<400> SEQUENCE: 448
agcaagctgc cgaaccaaaa gaatt                                              25

<210> SEQ ID NO 449
<211> LENGTH: 25
<212> TYPE: DNA
<213> ORGANISM: Homo sapiens
```

<400> SEQUENCE: 449
ggggtagggc tgactagaag ggcca                                    25

<210> SEQ ID NO 450
<211> LENGTH: 25
<212> TYPE: DNA
<213> ORGANISM: Homo sapiens

<400> SEQUENCE: 450
ggtggtgggg caacactgct taatg                                    25

<210> SEQ ID NO 451
<211> LENGTH: 25
<212> TYPE: DNA
<213> ORGANISM: Homo sapiens

<400> SEQUENCE: 451
gccatgaaaa ccttatgacc gtgca                                    25

<210> SEQ ID NO 452
<211> LENGTH: 25
<212> TYPE: DNA
<213> ORGANISM: Homo sapiens

<400> SEQUENCE: 452
tatacacaga catgctcttt tttta                                    25

<210> SEQ ID NO 453
<211> LENGTH: 25
<212> TYPE: DNA
<213> ORGANISM: Homo sapiens

<400> SEQUENCE: 453
caggggaacc ttccaaggtg tctgg                                    25

<210> SEQ ID NO 454
<211> LENGTH: 25
<212> TYPE: DNA
<213> ORGANISM: Homo sapiens

<400> SEQUENCE: 454
ccacagcctc aatcttgtat ttagt                                    25

<210> SEQ ID NO 455
<211> LENGTH: 25
<212> TYPE: DNA
<213> ORGANISM: Homo sapiens

<400> SEQUENCE: 455
gacggctgag tgcacaggtg ccgcc                                    25

<210> SEQ ID NO 456
<211> LENGTH: 25
<212> TYPE: DNA
<213> ORGANISM: Homo sapiens

<400> SEQUENCE: 456
atggctgttt tgttatgcca ccctg                                    25

<210> SEQ ID NO 457
<211> LENGTH: 25
<212> TYPE: DNA

```
<213> ORGANISM: Homo sapiens

<400> SEQUENCE: 457
tggggtgatg ggttgcagac ggagg                                            25

<210> SEQ ID NO 458
<211> LENGTH: 25
<212> TYPE: DNA
<213> ORGANISM: Homo sapiens

<400> SEQUENCE: 458
agccttccgg tcagtgacgt gtgag                                            25

<210> SEQ ID NO 459
<211> LENGTH: 25
<212> TYPE: DNA
<213> ORGANISM: Homo sapiens

<400> SEQUENCE: 459
agtatttaat tcatgttgcc ttgca                                            25

<210> SEQ ID NO 460
<211> LENGTH: 25
<212> TYPE: DNA
<213> ORGANISM: Homo sapiens

<400> SEQUENCE: 460
cccaccctgt aaactaggcg gctgc                                            25

<210> SEQ ID NO 461
<211> LENGTH: 25
<212> TYPE: DNA
<213> ORGANISM: Homo sapiens

<400> SEQUENCE: 461
gaggctcagg ggactggttg ggcca                                            25

<210> SEQ ID NO 462
<211> LENGTH: 25
<212> TYPE: DNA
<213> ORGANISM: Homo sapiens

<400> SEQUENCE: 462
ttcactcagg aaatgcatgt cagga                                            25

<210> SEQ ID NO 463
<211> LENGTH: 25
<212> TYPE: DNA
<213> ORGANISM: Homo sapiens

<400> SEQUENCE: 463
ccagggcaag ttcccagatc ctatg                                            25

<210> SEQ ID NO 464
<211> LENGTH: 25
<212> TYPE: DNA
<213> ORGANISM: Homo sapiens

<400> SEQUENCE: 464
ttctgaattc attatgatcc ccata                                            25

<210> SEQ ID NO 465
<211> LENGTH: 25
```

```
<212> TYPE: DNA
<213> ORGANISM: Homo sapiens

<400> SEQUENCE: 465
ggcgcccttt ccatagagaa tttgc                                          25

<210> SEQ ID NO 466
<211> LENGTH: 25
<212> TYPE: DNA
<213> ORGANISM: Homo sapiens

<400> SEQUENCE: 466
tgctgtggct tcaccaacta tacgg                                          25

<210> SEQ ID NO 467
<211> LENGTH: 25
<212> TYPE: DNA
<213> ORGANISM: Homo sapiens

<400> SEQUENCE: 467
aattgtgtga ggaacacgcc ggcct                                          25

<210> SEQ ID NO 468
<211> LENGTH: 25
<212> TYPE: DNA
<213> ORGANISM: Homo sapiens

<400> SEQUENCE: 468
ctgtagcatg ccgttctgga ttaat                                          25

<210> SEQ ID NO 469
<211> LENGTH: 25
<212> TYPE: DNA
<213> ORGANISM: Homo sapiens

<400> SEQUENCE: 469
atccgatgat agtactgcag ttttc                                          25

<210> SEQ ID NO 470
<211> LENGTH: 25
<212> TYPE: DNA
<213> ORGANISM: Homo sapiens

<400> SEQUENCE: 470
ggttccatca atggtgagca ccagc                                          25

<210> SEQ ID NO 471
<211> LENGTH: 25
<212> TYPE: DNA
<213> ORGANISM: Homo sapiens

<400> SEQUENCE: 471
gagctcagta tttagtcctt tgttt                                          25

<210> SEQ ID NO 472
<211> LENGTH: 25
<212> TYPE: DNA
<213> ORGANISM: Homo sapiens

<400> SEQUENCE: 472
aaattagcct ggacaaccct gacta                                          25

<210> SEQ ID NO 473
```

```
<211> LENGTH: 25
<212> TYPE: DNA
<213> ORGANISM: Homo sapiens

<400> SEQUENCE: 473
gaatggagca gttccttata taata                                              25

<210> SEQ ID NO 474
<211> LENGTH: 25
<212> TYPE: DNA
<213> ORGANISM: Homo sapiens

<400> SEQUENCE: 474
ggacaacttt gatattgctt ggcac                                              25

<210> SEQ ID NO 475
<211> LENGTH: 25
<212> TYPE: DNA
<213> ORGANISM: Homo sapiens

<400> SEQUENCE: 475
tcttgctcca aagggctccg tggag                                              25

<210> SEQ ID NO 476
<211> LENGTH: 25
<212> TYPE: DNA
<213> ORGANISM: Homo sapiens

<400> SEQUENCE: 476
taaaccatcc cgtagtcttc taata                                              25

<210> SEQ ID NO 477
<211> LENGTH: 25
<212> TYPE: DNA
<213> ORGANISM: Homo sapiens

<400> SEQUENCE: 477
gccagcagcc acaacatgca ttgac                                              25

<210> SEQ ID NO 478
<211> LENGTH: 25
<212> TYPE: DNA
<213> ORGANISM: Homo sapiens

<400> SEQUENCE: 478
ggattctagg ttggctgctg tgtca                                              25

<210> SEQ ID NO 479
<211> LENGTH: 25
<212> TYPE: DNA
<213> ORGANISM: Homo sapiens

<400> SEQUENCE: 479
gatgccagaa ggaaagccga aatgc                                              25

<210> SEQ ID NO 480
<211> LENGTH: 25
<212> TYPE: DNA
<213> ORGANISM: Homo sapiens

<400> SEQUENCE: 480
tgtgaccatg tttcctctca ataaa                                              25
```

```
<210> SEQ ID NO 481
<211> LENGTH: 25
<212> TYPE: DNA
<213> ORGANISM: Homo sapiens

<400> SEQUENCE: 481
cgtggcactg gtaggttggg acacc                                          25

<210> SEQ ID NO 482
<211> LENGTH: 25
<212> TYPE: DNA
<213> ORGANISM: Homo sapiens

<400> SEQUENCE: 482
gatgagcacc agttacacaa ggact                                          25

<210> SEQ ID NO 483
<211> LENGTH: 25
<212> TYPE: DNA
<213> ORGANISM: Homo sapiens

<400> SEQUENCE: 483
ctcaatgaag ggtcccaagc ccgtc                                          25

<210> SEQ ID NO 484
<211> LENGTH: 25
<212> TYPE: DNA
<213> ORGANISM: Homo sapiens

<400> SEQUENCE: 484
tcacatgtgt gagtcttacg tgcac                                          25

<210> SEQ ID NO 485
<211> LENGTH: 25
<212> TYPE: DNA
<213> ORGANISM: Homo sapiens

<400> SEQUENCE: 485
aaaagagcat gatcctgtag gtcaa                                          25

<210> SEQ ID NO 486
<211> LENGTH: 25
<212> TYPE: DNA
<213> ORGANISM: Homo sapiens

<400> SEQUENCE: 486
cttttcactg tgttggagtt ttctg                                          25

<210> SEQ ID NO 487
<211> LENGTH: 25
<212> TYPE: DNA
<213> ORGANISM: Homo sapiens

<400> SEQUENCE: 487
tttcctctta tcaacaactt gtgac                                          25

<210> SEQ ID NO 488
<211> LENGTH: 25
<212> TYPE: DNA
<213> ORGANISM: Homo sapiens

<400> SEQUENCE: 488
accaggggca agccatgcac atgca                                          25
```

```
<210> SEQ ID NO 489
<211> LENGTH: 25
<212> TYPE: DNA
<213> ORGANISM: Homo sapiens

<400> SEQUENCE: 489
gcctcgacac acataaacct tttta                                    25

<210> SEQ ID NO 490
<211> LENGTH: 25
<212> TYPE: DNA
<213> ORGANISM: Homo sapiens

<400> SEQUENCE: 490
tggccttatc cgtgcagtgg tggca                                    25

<210> SEQ ID NO 491
<211> LENGTH: 25
<212> TYPE: DNA
<213> ORGANISM: Homo sapiens

<400> SEQUENCE: 491
atgtctgctg ggtgtgacca tgttt                                    25

<210> SEQ ID NO 492
<211> LENGTH: 25
<212> TYPE: DNA
<213> ORGANISM: Homo sapiens

<400> SEQUENCE: 492
tcgccaccta caggaagctg ctgga                                    25

<210> SEQ ID NO 493
<211> LENGTH: 25
<212> TYPE: DNA
<213> ORGANISM: Homo sapiens

<400> SEQUENCE: 493
tcctgctgca ccttgagtca gagct                                    25

<210> SEQ ID NO 494
<211> LENGTH: 25
<212> TYPE: DNA
<213> ORGANISM: Homo sapiens

<400> SEQUENCE: 494
taagatatgt tcttgctctt ttata                                    25

<210> SEQ ID NO 495
<211> LENGTH: 25
<212> TYPE: DNA
<213> ORGANISM: Homo sapiens

<400> SEQUENCE: 495
tgcagtagtg ccaaaaggcc ccttc                                    25

<210> SEQ ID NO 496
<211> LENGTH: 25
<212> TYPE: DNA
<213> ORGANISM: Homo sapiens

<400> SEQUENCE: 496
tgcttagctg ccttgagcta acccc                                    25
```

```
<210> SEQ ID NO 497
<211> LENGTH: 25
<212> TYPE: DNA
<213> ORGANISM: Homo sapiens

<400> SEQUENCE: 497
aacctactag tcttgaacaa actgt                                              25

<210> SEQ ID NO 498
<211> LENGTH: 25
<212> TYPE: DNA
<213> ORGANISM: Homo sapiens

<400> SEQUENCE: 498
gggcagactg tgaacttgac tgggt                                              25

<210> SEQ ID NO 499
<211> LENGTH: 25
<212> TYPE: DNA
<213> ORGANISM: Homo sapiens

<400> SEQUENCE: 499
agacagcaat gacagtccac ctgcc                                              25

<210> SEQ ID NO 500
<211> LENGTH: 25
<212> TYPE: DNA
<213> ORGANISM: Homo sapiens

<400> SEQUENCE: 500
taaatctttt acaactgcct cgaca                                              25

<210> SEQ ID NO 501
<211> LENGTH: 25
<212> TYPE: DNA
<213> ORGANISM: Homo sapiens

<400> SEQUENCE: 501
gtggatgttg cactcaaacg ggctg                                              25

<210> SEQ ID NO 502
<211> LENGTH: 25
<212> TYPE: DNA
<213> ORGANISM: Homo sapiens

<400> SEQUENCE: 502
gttactgtgc catgtgttta tccta                                              25

<210> SEQ ID NO 503
<211> LENGTH: 25
<212> TYPE: DNA
<213> ORGANISM: Homo sapiens

<400> SEQUENCE: 503
tttcccatga tagtgcttcg ttttt                                              25

<210> SEQ ID NO 504
<211> LENGTH: 25
<212> TYPE: DNA
<213> ORGANISM: Homo sapiens

<400> SEQUENCE: 504
```
taagccacct tctactatgc aattt                                              25

<210> SEQ ID NO 505
<211> LENGTH: 25
<212> TYPE: DNA
<213> ORGANISM: Homo sapiens

<400> SEQUENCE: 505
caaggcagac acctactgcg cgtag                                              25

<210> SEQ ID NO 506
<211> LENGTH: 25
<212> TYPE: DNA
<213> ORGANISM: Homo sapiens

<400> SEQUENCE: 506
gcatgtggac agtcgcgagc gttta                                              25

<210> SEQ ID NO 507
<211> LENGTH: 25
<212> TYPE: DNA
<213> ORGANISM: Homo sapiens

<400> SEQUENCE: 507
gccggcttcg tgaaggagtt ctccc                                              25

<210> SEQ ID NO 508
<211> LENGTH: 25
<212> TYPE: DNA
<213> ORGANISM: Homo sapiens

<400> SEQUENCE: 508
aaacaagcta attcctctat gccac                                              25

<210> SEQ ID NO 509
<211> LENGTH: 25
<212> TYPE: DNA
<213> ORGANISM: Homo sapiens

<400> SEQUENCE: 509
ttccacaagt actcctgcca agagg                                              25

<210> SEQ ID NO 510
<211> LENGTH: 25
<212> TYPE: DNA
<213> ORGANISM: Homo sapiens

<400> SEQUENCE: 510
gttgttgtct cattttggtc tgttt                                              25

<210> SEQ ID NO 511
<211> LENGTH: 25
<212> TYPE: DNA
<213> ORGANISM: Homo sapiens

<400> SEQUENCE: 511
ttccactagg gtccaccagg agttc                                              25

<210> SEQ ID NO 512
<211> LENGTH: 25
<212> TYPE: DNA
<213> ORGANISM: Homo sapiens

<400> SEQUENCE: 512
gaggcctggc ggaatggtgg tgccc                                              25

<210> SEQ ID NO 513
<211> LENGTH: 25
<212> TYPE: DNA
<213> ORGANISM: Homo sapiens

<400> SEQUENCE: 513
aagcttcaaa ctaggtattc tggga                                              25

<210> SEQ ID NO 514
<211> LENGTH: 25
<212> TYPE: DNA
<213> ORGANISM: Homo sapiens

<400> SEQUENCE: 514
gttcctttga gtgtcttcta acttt                                              25

<210> SEQ ID NO 515
<211> LENGTH: 25
<212> TYPE: DNA
<213> ORGANISM: Homo sapiens

<400> SEQUENCE: 515
tgtgtctgat cctcattttt caacc                                              25

<210> SEQ ID NO 516
<211> LENGTH: 25
<212> TYPE: DNA
<213> ORGANISM: Homo sapiens

<400> SEQUENCE: 516
aatttggtca agtctactct tccgt                                              25

<210> SEQ ID NO 517
<211> LENGTH: 25
<212> TYPE: DNA
<213> ORGANISM: Homo sapiens

<400> SEQUENCE: 517
accaaggagc tggtcagacg gccct                                              25

<210> SEQ ID NO 518
<211> LENGTH: 25
<212> TYPE: DNA
<213> ORGANISM: Homo sapiens

<400> SEQUENCE: 518
gatactaagg acgttgtttt ggttg                                              25

<210> SEQ ID NO 519
<211> LENGTH: 25
<212> TYPE: DNA
<213> ORGANISM: Homo sapiens

<400> SEQUENCE: 519
gtatcttcat acacgtttgg aaatg                                              25

<210> SEQ ID NO 520
<211> LENGTH: 25
<212> TYPE: DNA
<213> ORGANISM: Homo sapiens

```
<400> SEQUENCE: 520
caggagctgt tcaagcgcat ctccg                                           25

<210> SEQ ID NO 521
<211> LENGTH: 25
<212> TYPE: DNA
<213> ORGANISM: Homo sapiens

<400> SEQUENCE: 521
cccacctttg acttaagatc ccaca                                           25

<210> SEQ ID NO 522
<211> LENGTH: 25
<212> TYPE: DNA
<213> ORGANISM: Homo sapiens

<400> SEQUENCE: 522
agatttctat gcacctttac tcttt                                           25

<210> SEQ ID NO 523
<211> LENGTH: 25
<212> TYPE: DNA
<213> ORGANISM: Homo sapiens

<400> SEQUENCE: 523
agtccaaatc gcaggcatat gctat                                           25

<210> SEQ ID NO 524
<211> LENGTH: 25
<212> TYPE: DNA
<213> ORGANISM: Homo sapiens

<400> SEQUENCE: 524
agcctgctca gctctgcata agtaa                                           25

<210> SEQ ID NO 525
<211> LENGTH: 25
<212> TYPE: DNA
<213> ORGANISM: Homo sapiens

<400> SEQUENCE: 525
agcttcatgt tgctctgcga caatc                                           25

<210> SEQ ID NO 526
<211> LENGTH: 25
<212> TYPE: DNA
<213> ORGANISM: Homo sapiens

<400> SEQUENCE: 526
ggagctcacc tttgaggaga ctgag                                           25

<210> SEQ ID NO 527
<211> LENGTH: 25
<212> TYPE: DNA
<213> ORGANISM: Homo sapiens

<400> SEQUENCE: 527
taacccattt agtcatctca cagaa                                           25

<210> SEQ ID NO 528
<211> LENGTH: 25
<212> TYPE: DNA
<213> ORGANISM: Homo sapiens
```

-continued

```
<400> SEQUENCE: 528
agaacaagcg tcggaggggc tgtcc                                          25
```

UNITED STATES PATENT AND TRADEMARK OFFICE
CERTIFICATE OF CORRECTION

PATENT NO. : 10,900,089 B2
APPLICATION NO. : 15/978655
DATED : January 26, 2021
INVENTOR(S) : Steen Knudsen It is certified that error appears in the above-identified patent and that said Letters Patent is hereby corrected as shown below:

In the Claims

Column 225, Line 41, replace "docetaxel,cabazitaxel" with --docetaxel, cabazitaxel--.
    Line 53, replace "AP0010" with --APO010--.

Column 228, Line 15, replace "AP0010" with --APO010--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*